United States Patent
Chang et al.

(10) Patent No.: US 6,664,241 B2
(45) Date of Patent: Dec. 16, 2003

(54) WATER-SOLUBLE AMIDE DERIVATIVES OF POLYENE MACROLIDES AND PREPARATION AND USES THEREOF

(75) Inventors: Conway C. Chang, Cambridge, MA (US); Binh T. Dang, San Jose, CA (US); Christopher J. Baldwin, Santa Cruz, CA (US); David J. Loury, San Jose, CA (US); Reyna J. Simon, Los Gatos, CA (US); Robert R. Webb, Moss Beach, CA (US)

(73) Assignee: Micrologix Biotech Inc., Vancouver (CA)

( * ) Notice: Subject to any disclaimer, the term of this patent is extended or adjusted under 35 U.S.C. 154(b) by 0 days.

(21) Appl. No.: 09/870,071

(22) Filed: May 29, 2001

(65) Prior Publication Data

US 2003/0040493 A1 Feb. 27, 2003

Related U.S. Application Data

(60) Provisional application No. 60/207,659, filed on May 31, 2000.

(51) Int. Cl.⁷ .......................... A61K 31/70; C07H 17/08
(52) U.S. Cl. ........................................... 514/31; 536/7.1
(58) Field of Search ............................... 536/6.5; 514/31

(56) References Cited

U.S. PATENT DOCUMENTS

| | | | |
|---|---|---|---|
| 4,093,796 A | * 6/1978 | Falkowski et al. | ............ 536/6.5 |
| 4,365,058 A | 12/1982 | Falkowski et al. | |
| 4,783,527 A | 11/1988 | Falkowski et al. | |
| 5,296,597 A | 3/1994 | Bruzzese et al. | |
| 5,298,495 A | 3/1994 | Bruzzese et al. | |

OTHER PUBLICATIONS

Bruzzese et al., "Amide Derivatives of Partricin A with Potent Antifungal Activity", *Euro. J. Med. Chem.*, 31:965–972 (1996).

Chéron et al., "Quantitative Structure–Activity Relationships in Amphotericin B Derivatives", *Biochemical Pharmacology*, 37 (5):827–836 (1988).

Czerwiński et al., "Amphotericin B 2-Morpholinoethylamide Diaspartate, A New Water Soluble Derivative of the Antibiotic Syntheisis and Biological Properties", *J. of Antibiotics*, XLIII(6):680–683 (1990).

Graybill et al., "KY–62, a Polyene Analog of Amphotericin B, for Treatment of Murine Candidiasis", *Antimicrobial Agents and Chemotherapy*, 42(1):147–150 (1998).

Grzybowska and Borowski, "Hydrazides—A Novel Type of Derivatives of Polyne Macrolide Antifungal Antibiotics", *J. of Antibiotics*, XLIII(7):907–908 (1990).

Jarzebski et al., "Synthesis and Structure–Activity Relationships of Amides of Amphotericin B", *J. of Antibiotics*, XXXV(2):220–229 (1982).

Yamashita et al., "Micelle/Monomer Control over the Membrane–Disrupting Properties of an Amphiphilic Antibiotic", *J. Am. Chem. Soc.*, 117:6249–6253 (1995).

\* cited by examiner

*Primary Examiner*—Elli Peselev
(74) *Attorney, Agent, or Firm*—Seed IP Law Group, PLLC

(57) ABSTRACT

The present invention provides two new classes of polyene macrolide amide derivatives useful for treating or preventing fungal infections. The new polyene macrolide amide derivatives exhibit antifungal activity and are more water-soluble than conventional polyene antibiotics, such as amphotericin B and amphotericin B methyl ester.

41 Claims, No Drawings

WATER-SOLUBLE AMIDE DERIVATIVES OF POLYENE MACROLIDES AND PREPARATION AND USES THEREOF

1. CROSS-REFERENCE TO RELATED APPLICATIONS

This application claims priority under 35 U.S.C. §119(e) to U.S. provisional application Serial No. 60/207,659, filed May 31, 2000, the disclosure of which is incorporated herein by reference in its entirety.

2. BACKGROUND OF THE INVENTION

2.1 Field of the Invention

The present invention relates generally to derivatives of polyene macrolides. In particular, the present invention relates to water-soluble amide derivatives of polyene macrolides useful for treating or preventing topical and/or systemic fungal infections in plants, humans and animals.

2.2 Description of Related Art

Many polyene macrolides are known that have antifungal properties useful for treating topical and/or systemic fungal infections. Examples of these polyene macrolides include amphotericin B, aureofacin, candicidin, candidin, levorin, mycoheptin, nystatin, partricin A, partricin B, perimycin, pimaricin, polyfungin, rimocidin and trichomycin. However, due to their amphoteric character, these compounds generally have limited solubility in aqueous solutions, which in turn limits their usefulness in the treatment of systemic fungal infections. In prior attempts to modify these compounds, some of the derivatives exhibited undesirable toxic properties when used systemically. For example, while amphotericin B methyl ester (AME) exhibited lower acute, nephro- and hepato-toxicity than amphotericin B in rats and dogs, in the only clinical trial conducted with AME in patients with systemic fungal infections, many patients developed progressive neurological dysfunction associated with white matter degeneration, see Ellis et al., 1988, Tox. Path. 16(1):1; Parmegiani et al., 1987, Antimicrob. Agents Chemo. 31(11):1756–1760; Hoeprich et al., 1985, Diag. Microbiol. Infect. Dis. 3:47–58; Massa et al., 1985, Fund. App. Tox. 5:737–753; Keim Jr., et al., 1976, Antimicrob. Agents Chemo. 10(4):687–690; and Keim Jr., et al., 1973, Science 179:584–586. The incidence and severity of these complications increased with the amount of AME administered (Id.). In fact, the toxicity of AME was so severe that the clinical trial was canceled and the product was never brought to market.

Many derivatives of polyene macrolides have been developed, in part to address these limitations. One class of derivatives include certain polyene macrolides substituted at the amino group of the amino sugar residue. For example, U.S. Pat. No. 4,093,796 to Falkowski et al. teaches polyene macrolides substituted at the sugar amino group with a saccharide. U.S. Pat. No. 4,195,172 to Falkowski et al. teaches N-methylglucamine salts of N-glycosyl derivatives of polyene macrolides in which the amino group of the polyene macrolide is substituted with an aldose or ketose mono- or oligosaccharide. U.S. Pat. No. 4,294,958 to Falkowski et al. teaches trimethylammonium salts of polyene macrolides, including the methyl esters. U.S. Pat. No. 4,365,058 to Falkowski et al. teaches esters of polyene macrolides that are substituted at the sugar amino group with non-sugar substituents. U.S. Pat. No. 5,314,999 to Seman et al. teaches polyene macrolides substituted at the N position with a 1-amino-1-deoxyketose group, which itself may be further substituted. U.S. Pat. No. 5,942,495 to Borowski et al. teaches N-alkyl-N-glycosyl derivatives of polyene macrolides that are reported to have antifungal activity, form water-soluble salts with acids, and have lower toxicity than other N-alkyl polyene macrolide derivatives.

Other derivatives reported in the literature include amides of certain polyene macrolides derivatives. For example, U.S. Pat. No. 4,783,527 to Falkowski et al. teaches alkyl, isoalkyl and heterocyclic amide derivatives of polyene macrolides. Jarzbeslo et al., 1982, J. Antibiot. 35(2):220–229 teach aliphatic amides of amphotericin B. Czerwinski et al., 1990, J. Antibiot. 43(6):980–683 teach amphotericin B 2-morpholinoethylamide. Grzybowska & Borowski, 1990, J. Antibiot. 43(7):907–908 teach hydrazides of amphotericin B, candidin, aureofacin and nystatin. Graybill et al., 1998, Antimicrobial Agents and Chemother. 42(1)147–150 and Yamashita et al., 1995, J. Am. Chem. Soc. 117(23):6249–6253 teach oligo(ethlene glycol) amides of ampotericin B. Chéron et al., 1988, Biochem. Pharmacol. 37(5):827–836 teach certain alkyl amides of amphotericin B that are further amidated at the polyene amino sugar residue. Lastly, Bruzzese et al., 1996, Eur. J. Med. Chem. 31:965–972, U.S. Pat. No. 5,296,597 to Bruzzese et al. and U.S. Pat. No. 5,298,495 to Bruzzese et al. teach certain amide derivatives of partricins A and B.

None of the foregoing derivatives provide an optimum combination of water solubility, low toxicity, and potency as an antifungal agent. Since AmB is still the drug of choice for many indications, there is a need for polyene macrolide derivatives that exhibit antifungal activity and that have improved water solubility and/or toxicity properties.

3. SUMMARY OF THE INVENTION

In one aspect, the present invention provides new polyene macrolide amide derivatives that have antifungal activity and that have increased water solubility as compared with amphotericin B (AmB) and amphotericin B methyl ester (AME). The polyene macrolide amide derivatives generally comprise a "core" polyene macrolide backbone derived from any of a variety of parent polyene macrolides having two features: an exocyclic carboxyl group and an amino sugar residue. The exocyclic carboxyl group of the parent polyene macrolide is amidated with substituents that increase the water-solubility of the resultant polyene as compared with AmB and AME. In one class of polyene macrolide amide derivatives of the invention, the nitrogen atom of the primary amino group of the amino sugar residue ("amino nitrogen") is substituted with a carbohydrate residue, which may be a mono-, di-, oligo- or polysaccharide. In all of the compounds of the invention, the amino nitrogen may be optionally alkylated. In embodiments in which the amino nitrogen is dialkylated, the alkyl groups may be the same or different.

While not intending to be bound by any particular theory of operation, the increased water-solubility of the amide derivatives of the invention is believed to be due to the presence of one or more of the same or different water solubility-increasing substituents attached to and/or including the nitrogen atom of the amide group ("amide nitrogen"). The water-solubility increasing substituents are generally polar in character, typically by virtue of including one or more of the same or different substituted or unsubstituted heteroatoms (e.g., S, O, N, NH, etc.).

In one embodiment, the water-solubility increasing substituents are hydrocarbons such as, by way of example and not limitation, linear and branched alkyls, cycloalkyls, aryls and arylalkyls that are substituted with one or more of the same or different polar substituents. Typical polar substituents include, but are not limited to, —OH, —SH, =O (oxo), =S (thioxo), —NH$_2$, =NH (imino), —C(=NH)—NH$_2$ (amidino), —NH—C(=NH)—NH$_2$ (guanidino), —C(O)H, —C(O)OH, —C(O)O$^-$M$^+$, —C(O)NH$_2$, —N$_3$, —CN, —X, —CX$_3$, etc., where each X is independently a halogen, preferably F, Cl or Br and M$^+$ represents a monovalent counter ion such as Na$^+$, K$^+$, etc. The polar-substituted alkyls, cycloalkyls, aryls and arylalkyls may also be optionally substituted with one or more of the same or different non-polar substituents, e.g., alkyls, cycloalkyls, aryls and arylalkyls, etc.

In another embodiment, the water-solubility increasing substituents are hydrocarbons in which one or more of the carbon atoms are replaced with the same or different heteroatoms to form, by way of example and not limitation, linear and branched heteroalkyls, cycloheteroalkyls, heteroaryls and heteroarylalkyls. One or more of the carbon atoms and/or heteroatoms (e.g., N) of these heteroalkyl, cycloheteroalkyl, heteroaryl and heteroarylalkyl groups may be further substituted with one or more of the same or different polar or non-polar substituents, as described above.

In still another embodiment, the water solubility-increasing substituents, taken together with the amide nitrogen to which they are bonded, form a saturated or unsaturated nitrogen-containing ring. The ring may optionally include one or more of the same or different additional ring heteroatoms, and/or may be optionally substituted at one or more ring carbon or heteroatoms with the same or different polar or non-polar substituents, as previously described.

In one embodiment of the invention, the water solubility-increasing substituents are selected from the group consisting of polyhydroxylated alkyls, mono-, di-, oligo- and polysaccharides, polyalkylene glycols (e.g., polyethylene glycol, polypropylene glycol, etc.) and polyalkylene oxides.

In embodiments of the invention in which the amide nitrogen includes only a single water-solubility increasing substituent, the other amide nitrogen substituent may be a hydrogen or a non-polar substituent, as described above.

In embodiments of the invention which include a carbohydrate residue at the amino nitrogen, the carbohydrate residue is generally added via an Amadori rearrangement with a reducing carbohydrate.

In one illustrative embodiment, the present invention provides polyene macrolide amide derivatives according to structural formula (I):

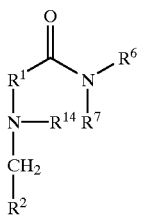

(I)

including the pharmaceutically acceptable salts thereof, wherein:
N—$R^1$—C(O) is a polyene macrolide backbone;
$CH_2$—$R^2$ is a carbohydrate residue, where the illustrated $CH_2$ is derived from the anomeric carbon of a terminal carbohydrate saccharide and $R^2$ represents the remainder of the carbohydrate;
either: (i) $R^6$ and $R^7$ are each, independently of one another, selected from the group consisting of hydrogen, non-polar substituent and water-solubility increasing substituent, with the proviso that at least one of $R^6$ or $R^7$ is a water-solubility increasing substituent; or (ii) $R^6$ and $R^7$, taken together with the amide nitrogen to which they are bonded, form a saturated or unsaturated ring which optionally includes one or more of the same or different additional ring heteroatoms and which is optionally further substituted with one or more of the same or different polar or non-polar substituent or combinations thereof; and
$R^{14}$ is hydrogen or alkyl.

In another illustrative embodiment, the present invention provides polyene macrolide amide derivatives according to structural formula (II):

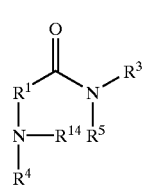

(II)

including the pharmaceutically acceptable salts thereof, wherein:
N—$R^1$—C(O) and $R^{14}$ are as previously defined for structural formula (I);
$R^3$ is hydrogen, a non-polar substituent or a water-solubility increasing substituent;
$R^4$ is hydrogen or alkyl; and
$R^5$ is a water-solubility increasing substituent selected from the group consisting of polyhydroxylated alkyl, monosaccharide, disaccharide and oligosaccharide.

In certain embodiments of the polyene macrolide amide derivatives according to structural formula (I), $R^6$ is hydrogen and/or $R^{14}$ is hydrogen. In certain embodiments of the polyene macrolide amide derivatives according to structural formula (II), $R^3$ is hydrogen and/or one or both of $R^4$ and $R^{14}$ are hydrogen.

In another aspect, the present invention provides methods of making the polyene macrolide amide derivatives of the invention. To obtain an amide derivative according to structural formula (II) in which $R^4$ and $R^{14}$ are each hydrogen, a parent polyene macrolide is reacted with an appropriate amine according to known methods or the methods described below. Derivatives according to structural formula (II) in which $R^4$ and/or $R^{14}$ is alkyl may be obtained from the above product using standard alkylation methods. Alternatively, the parent polyene macrolide may be first alkylated according to standard methods and the alkylated intermediate amidated according to known methods or the methods described below.

To obtain a polyene macrolide amide derivative according to structural formula (I) in which $R^{14}$ is hydrogen, a parent polyene macrolide is first reacted with an appropriate reducing carbohydrate under Amadori rearrangement conditions to yield an Amadori product that is substituted at the amino nitrogen with a carbohydrate residue. This Amadori product is then reacted with an appropriate amine according to known methods or the methods described below to yield a polyene amide derivative according to structural formula (I). Derivatives according to structural formula (I) in which $R^{14}$ is alkyl may be obtained from the above product using standard alkylation methods. Alternatively, the parent polyene macrolide may be first monoalkylated prior to the Amadori rearrangement reaction, or the Amadori product may be alkylated prior to the amidation reaction.

Alternatively, the amide derivatives according to structural formula (I) may be prepared by reacting an amide derivative according to structural formula (II) in which at least one of $R^4$ or $R^{14}$ is hydrogen with an appropriate reducing carbohydrate under Amadori rearrangement conditions. If this alternative route is used, any substituents on the amide moiety that are capable of reacting with the reducing carbohydrate should be protected prior to reaction with the reducing carbohydrate. If $R^4$ and $R^{14}$ of the starting material were each hydrogen, derivatives according to structural formula (I) in which $R^{14}$ is alkyl may be obtained from the above product using standard alkylation methods.

In a specific embodiment of the invention, the amidation step of the synthesis is carried out using a uronium salt or phosphonium salt coupling reagent. The reaction is typically carried out in the presence of an organic amine-containing base.

In another embodiment, the polyene macrolide amide derivatives of formula (I) are synthesized in a one-pot reaction. According to this embodiment, a parent polyene macrolide is first reacted with a reducing carbohydrate under Amadori rearrangement conditions. Without any isolation or purification, the Amadori product is then amidated utilizing a uronium salt or phosphonium salt coupling reagent, as described above. If an alkylated derivative is desired, the parent polyene macrolide should be alkylated first and then used as a starting reagent in the one-pot reaction.

In all of the described synthetic routes, where applicable, the intermediates and/or reaction products may be isolated using standard techniques, such as precipitation and/or chromatography.

In another aspect, the present invention provides pharmaceutical compositions including the new polyene macrolide amide derivatives. The pharmaceutical compositions generally comprise one or more polyene macrolide amide derivatives of the invention (which may be in the form of the pharmaceutically acceptable salts thereof) and a pharmaceutically acceptable carrier, excipient or diluent. The choice of carrier, excipient or diluent will depend upon, among other factors, the desired mode of administration.

In still another aspect the present invention provides methods of inhibiting the growth of fungi, such as *C. albicans* and other Candida species (e.g., *C. glabrata*), *Crytococcus neoformans, Blastomyces dermatitidis, Histoplasma capsulatum, Torulopsis glabrata, Coccidioides immitus, Paracoccidioides braziliensis,* Aspergillus species and the agents of mucormycosis. The method generally involves contacting a fungus with an amount of a polyene macrolides amine derivative of the invention, or a pharmaceutically-acceptable salt thereof, effective to inhibit the growth of the fungus. The method may be practiced to achieve a fungistatic effect, where the growth of the fungus is inhibited, or to achieve a fungicidal effect, where the fungus is killed.

In a final aspect, the present invention provides methods for treating and/or preventing fungal infections in humans, animals and/or plants. The methods generally involve administering to a human, animal or plant one or more of the polyene macrolide amide derivatives or pharmaceutical compositions of the invention in an amount effective to treat or prevent a fungal infection in the human, animal or plant. The polyene macrolide amide derivatives or pharmaceutical compositions may be administered systemically or applied topically, depending on the nature of the fungal infection.

4. DETAILED DESCRIPTION OF THE PREFERRED EMBODIMENTS

4.1 Definitions

As used herein, the following terms are intended to have the following meanings.

"Alkyl" refers to a saturated or unsaturated, branched, straight-chain or cyclic monovalent hydrocarbon group derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" is specifically intended to include groups having any degree or level of saturation, i.e., groups having exclusively carbon-carbon single bonds, groups having one or more carbon-carbon double bonds, groups having one or more carbon-carbon triple bonds and groups having mixtures of single, double and triple carbon-carbon bonds. Where a specific level of saturation is intended, the expressions "alkanyl," "alkenyl," and "alkynyl" are used. The expression "lower alkyl" refers to alkyl groups comprising from 1 to 8 carbon atoms.

The number of carbon atoms comprising a particular alkyl may vary widely, and is limited only by the properties of the resultant molecule. For example, if an alkyl is included as a non-polar substituent group on a water-solubility increasing substituent, it should have a number of carbon atoms that does not cause the water-solubility increasing substituent to become net hydrophobic in character. In this instance, the alkyl will generally comprise from 1 to 20 carbon atoms, typically from 1 to 10 carbon atoms, usually from 1 to 8 carbon atoms and most frequently from 1 to 4 carbon atoms. For amide derivatives on the invention that are alkylated at the amino nitrogen, the alkyl will generally comprise from 1 to 20 carbon atoms, typically from 1 to 10 carbon atoms, usually from 1 to 8 carbon atoms and most frequently from 1 to 4 carbon atoms, although it may comprise greater numbers of carbon atoms provided that the resultant molecule is active as described herein.

"Alkanyl" refers to a saturated branched, straight-chain or cyclic alkyl group derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butyanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl" refers to an unsaturated branched, straight-chain or cyclic alkyl group having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" refers to an unsaturated branched, straight-chain or cyclic alkyl group having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Cycloalkyl" refers to a saturated or unsaturated cyclic alkyl group. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. In a preferred embodiment, the cycloalkyl group is ($C_3$–$C_6$) cycloalkyl, more preferably ($C_3$–$C_6$) cycloalkanyl.

"Alkyldiyl" refers to a saturated or unsaturated, branched, straight-chain or cyclic divalent hydrocarbon group derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. In preferred embodiments, the alkyldiyl group is ($C_1$–$C_6$) alkyldiyl. Also preferred are saturated acyclic alkanyldiyl groups in which the radical centers are at the terminal carbons, e.g., methandiyl (methano); ethan-1,2-diyl (ethano); propan-1,3-diyl (propano); butan-1,4-diyl (butano); and the like (also referred to as alkylenos, defined infra).

"Alkyleno" refers to a straight-chain alkyldiyl group having two terminal monovalent radical centers derived by the removal of one hydrogen atom from each of the two terminal carbon atoms of straight-chain parent alkane, alkene or alkyne. Typical alkyleno groups include, but are not limited to, methano; ethylenos such as ethano, etheno, ethyno; propylenos such as propano, prop[1]eno, propa[1,2]dieno, prop[1]yno, etc.; butylenos such as butano, but[1]eno, but[2]eno, buta[1,3]dieno, but[1]yno, but[2]yno, but[1,3]diyno, etc.; and the like. Where specific levels of saturation are intended, the nomenclature alkano, alkeno and/or alkyno is used. In preferred embodiments, the alkyleno group is ($C_1$–$C_6$) or ($C_1$–$C_4$) alkyleno. Also preferred are straight-chain saturated alkano groups, e.g., methano, ethano, propano, butano, and the like.

"Heteroalkyl, Heteroalkanyl, Heteroalkenyl, Heteroalkanyl Heteroalkyldiyl and Heteroalkyleno" refer to alkyl, alkanyl, alkenyl, alkynyl, alkyldiyl and alkyleno groups, respectively, in which one or more of the carbon atoms (and any associated hydrogen atoms) are each independently replaced with the same or different heteroatoms or heteroatomic groups. Typical heteroatoms or heteroatomic groups which can be included in these groups include, but are not limited to, —O—, —S—, —Se—, —O—O—, —S—S—, —O—S—, —O—S—O—, —O—NR'—, —NR'—, —NR'—NR'—, =N—N=, —N=N—, —N=N—NR'—, —PH—, —P(O)$_2$—, —O—P(O)$_2$—, —SH$_2$—, —S(O)$_2$—, —SnH$_2$— and the like, and combinations thereof, including, for example, —NR'—S(O)$_2$—, where each R' is independently selected from the group consisting of hydrogen, alkyl, alkanyl, alkenyl, alkynyl, aryl, arylalkyl, heteroaryl and heteroarylalkyl, as defined herein.

"Cycloheteroalkyl" refers to a saturated or unsaturated cyclic alkyl group in which one or more carbon atoms (and any associated hydrogen atoms) are independently replaced with the same or different heteroatom or heteroatomic group. Typical heteroatoms to replace the carbon atom(s) include, but are not limited to, N, P, O, S, Si, etc. (including any associated hydrogen atoms, e.g., NH). Where a specific level of saturation is intended, the nomenclature "cycloheteroalkanyl" or "cycloheteroalkenyl" is used. Typical cycloheteroalkyl groups include, but are not limited to, groups derived from epoxides, imidazolidine, morpholine, piperazine, piperidine, pyrazolidine, pyrrolidine, quinuclidine, and the like. In preferred embodiments, the cycloheteroalkyl is a 3–6 membered cycloheteroalkyl. Particularly preferred cycloheteralkyls are morpholino, pyrrolidino, pipyridino, tetrahydrothiopheno, tetrahydrofuranyl and tetrahydropyranyl.

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In preferred embodiments, the aryl group is ($C_5$–$C_{14}$) aryl, with ($C_5$–$C_{10}$) being even more preferred. Particularly preferred aryls are cyclopentadienyl, phenyl and naphthyl.

"Arylalkyl" refers to an acyclic alkyl group in which one of the hydrogen atoms bonded to a carbon atom, typically a terminal or sp$^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylakenyl and/or arylalkynyl is used. In preferred embodiments, the arylalkyl group is ($C_6$–$C_{20}$) arylalkyl, e.g., the alkanyl, alkenyl or alkynyl moiety of the arylalkyl group is ($C_1$–$C_6$) and the aryl moiety is ($C_1$–$C_{14}$). In particularly preferred embodiments the arylalkyl group is ($C_6$–$C_{13}$), e.g., the alkanyl, alkenyl or alkynyl moiety of the arylalkyl group is ($C_1$–$C_3$) and the aryl moiety is ($C_5$–$C_{10}$).

"Parent Heteroaromatic Ring System" refers to a parent aromatic ring system in which one or more carbon atoms (and any associated hydrogen atoms) are each independently replaced with the same or different heteroatoms. Typical heteratoms to replace the carbon atoms include, but are not limited to, N, P, O, S, Si, etc. (including any associated hydrogen atoms, e.g., NH). Specifically included within the definition of "parent heteroaromatic ring systems" are fused ring systems in which one or more of the rings are aromatic and one or more of the rings are saturated or unsaturated, such as, for example, arsindole, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Heteroaryl" refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In preferred embodiments, the heteroaryl group is a 5–14 membered heteroaryl, with 5–10 membered heteroaryl being particularly preferred. The most preferred heteroaryl groups are those derived from thiophene, pyrrole, benzothiophene, benzofuran, indole, pyridine, quinoline, imidazole, oxazole and pyrazine.

"Heteroarylalkyl" refers to an acyclic alkyl group in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylakenyl and/or heterorylalkynyl is used. In preferred embodiments, the heteroarylalkyl group is a 6–20 membered heteroarylalkyl, e.g., the alkanyl, alkenyl or alkynyl moiety of the heteroarylalkyl is 1–6 membered and the heteroaryl moiety is a 5–14-membered heteroaryl. In particularly preferred embodiments, the heteroarylalkyl is a 6–13 membered heteroarylalkyl, e.g., the alkanyl, alkenyl or alkynyl moiety is 1–3 membered and the heteroaryl moiety is a 5–10 membered heteroaryl.

4.2 The Compounds

The present invention provides two new classes of polyene macrolide amide derivatives (and/or pharmaceutically acceptable salts thereof), pharmaceutical compositions comprising the new polyene macrolide amide derivatives, methods of making the new polyene macrolide amide derivatives, and methods of using the new polyene macrolide amide derivatives and/or pharmaceutical compositions to inhibit the growth of fungi and/or to treat and/or prevent fungal infections in both plants and animals, including humans.

The polyene macrolide amide derivatives of the invention provide significant advantages over traditional polyene macrolide antifungals. For example, the polyene macrolide amide derivatives of the present invention are more water soluble, and many exhibit lower acute toxicity, than traditional polyene macrolide antifungals such as amphotericin B (AmB) and amphotericin B methyl ester (AME). Owing in part to their water-solubility, the polyene macrolide amide derivatives of the invention do not require extensive formulation, making them extremely easy for use. Most dissolve readily in water in their free base forms, and all are readily soluble in water when prepared as pharmaceutically acceptable salts, such as aspartate salts. Thus, the amide derivatives of the invention may be stored dry and dissolved in water or other aqueous vehicles just prior to use. This is in stark contrast to AmB, which is typically sold as a lipid formulation (e.g., FUNGIZONE, Briston-Meyers Squibb Co.).

One class of polyene macrolide amide derivatives according to the invention includes compounds according to structural formula (I):

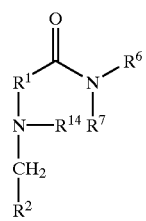

(I)

including the pharmaceutically acceptable salts thereof, wherein:

N—$R^1$—C(O) is a polyene macrolide backbone;

$CH_2$—$R^2$ is a carbohydrate residue, where the illustrated $CH_2$ is derived from the anomeric carbon of a terminal carbohydrate saccharide and $R^2$ represents the remainder of the carbohydrate;

either: (i) $R^6$ is selected from the group consisting of hydrogen, non-polar substituent and water-solubility increasing substituent and $R^7$ is a water-solubility increasing substituent; or (ii) $R^6$ and $R^7$, taken together with the amide nitrogen to which they are bonded, form a saturated or unsaturated ring which optionally includes one or more of the same or different additional ring heteroatoms and which is optionally further substituted with one or more of the same or different polar or non-polar substituent or combinations thereof; and $R^{14}$ is hydrogen or alkyl.

Another class of polyene macrolide amide derivatives according to the invention includes compounds according to structural formula (II):

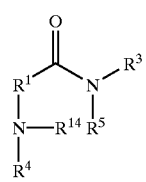

(II)

including the pharmaceutically acceptable salts thereof, wherein:

N—$R^1$—C(O) and $R^{14}$ are as previously defined for structural formula (I);

$R^3$ is hydrogen, a non-polar substituent or a water-solubility increasing substituent;

$R^4$ is hydrogen or alkyl; and $R^5$ is a water-solubility increasing substituent selected from the group consisting of polyhydroxylated alkyl, monosaccharide, disaccharide and oligosaccharide.

The compounds of the invention are amide derivatives of "parent" polyene macrolides of a particular type. Specifically, the parent polyene macrolides are of a type that have an exocyclic carboxyl group and an amino sugar residue, as exemplified by, for example, AmB and nystatin. In the compounds according to structural formulae (I) and (II), the exocyclic carboxyl group of the parent polyene macrolide is converted to an amide group. The nitrogen atom of this exocyclic amide group ("amide nitrogen") is substituted with one or more of the same or different substituents that increase the water-solubility of the resultant compound as compared with AmB and AME, as will be described in more detail, below.

In the compounds according to structural formula (I), the primary amino group of the amino sugar residue of the parent polyene macrolide is substituted with a carbohydrate residue. This carbohydrate residue, which is described in more detail below, is attached to the nitrogen atom of this primary amino group ("amino nitrogen") via the anomeric carbon of a terminal saccharide unit. The compounds of structural formulae (I) and (II) may also be alkylated at this amino nitrogen. In embodiments of the compounds of formula (II) which are dialkylated, the alkyl groups may be the same or different.

In the polyene macrolide amide derivatives of formulae (I) and (II), polyene backbone N—$R^1$—C(O) may be derived from any known or later discovered parent polyene macrolide having the features discussed above. Preferably, the parent polyene macrolide from which backbone N—$R^1$—C(O) is derived will have antifungal activity. Non-limiting examples of parent polyene macrolides having the required features from which polyene backbone N—$R^1$—C(O) may be derived include, but are not limited to, amphotericin A (AmA), amphotericin B (AmB), aureofacin, candicidin, candidin, levorin, mycoheptin, nystatin (including $A_1$), partricin (including A and B), pentamycin, perimycin, pimaricin, polyfungin, rimocidin, and trichomycin. Preferred classes of polyene backbones N—$R^1$—C(O) are those derived from AmB and nystatin. The structures of nystatin and AmB are as illustrated below, including citations referencing methods for obtaining these parent polyene macrolides (for each parent polyene macrolide, the required exocyclic carboxyl group and the amino primary group of the required amino sugar residue are illustrated in bold and indicated with arrows):

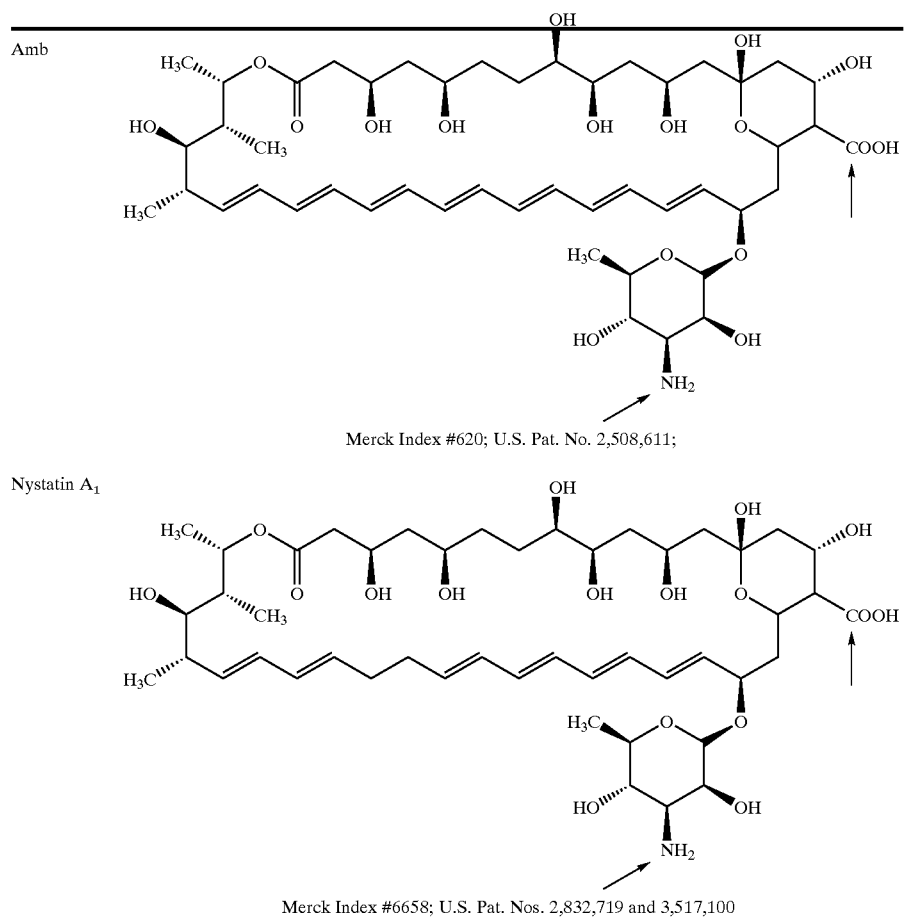

In the compounds according to structural formulae (I) and (II), the illustrated N—$R^1$—C(O) portion of the molecule is contributed by the parent polyene macrolide. Those of skill in the art will recognize that when $R^4$ and/or $R^{14}$ are hydrogen, these hydrogens are also contributed by the parent polyene macrolide. It will further be appreciated that polyene backbone N—$R^1$—C(O) includes the amino sugar moiety that is attached to the macrocyclic portion of parent polyene macrolide (e.g., the 3-amino-3,6-dideoxymannose of AmB and nystatin). This amino sugar, which is an inherent part of the parent polyene macrolide, is to be distinguished from the carbohydrate residue $CH_2$—$R^2$ of formula (I), which is not contributed by the parent polyene macrolide and constitutes one of the inventive features of certain amide derivatives of the invention.

As a specific example to clarify the nomenclature and compounds described herein, the polyene backbone N—$R^1$—C(O) derived from AmB is illustrated below, wherein the bold dashed lines indicate the atoms which are bonded to the $CH_2$—$R^2$, $NR^6R^7$ and $R^{14}$ substituents in the amide derivatives of formula (I) and the $NR^3R^5$, $R^4$ and $R^{14}$ substituents in the amide derivatives of formula (II):

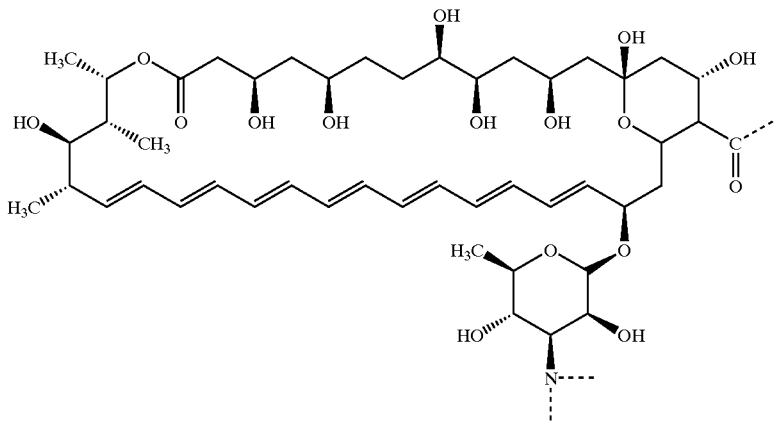

The structures of polyene backbones N—R¹—C(O) derived from other parent polyene macrolides will be apparent to those of skill in the art.

To further illustrate the compounds of the invention, the amide derivatives of structural formulae (I) and (II) in which N—R$^1$—C(O) is a polyene macrolide backbone derived from AmB are provided below as structures (Ia) and (IIa), respectively:

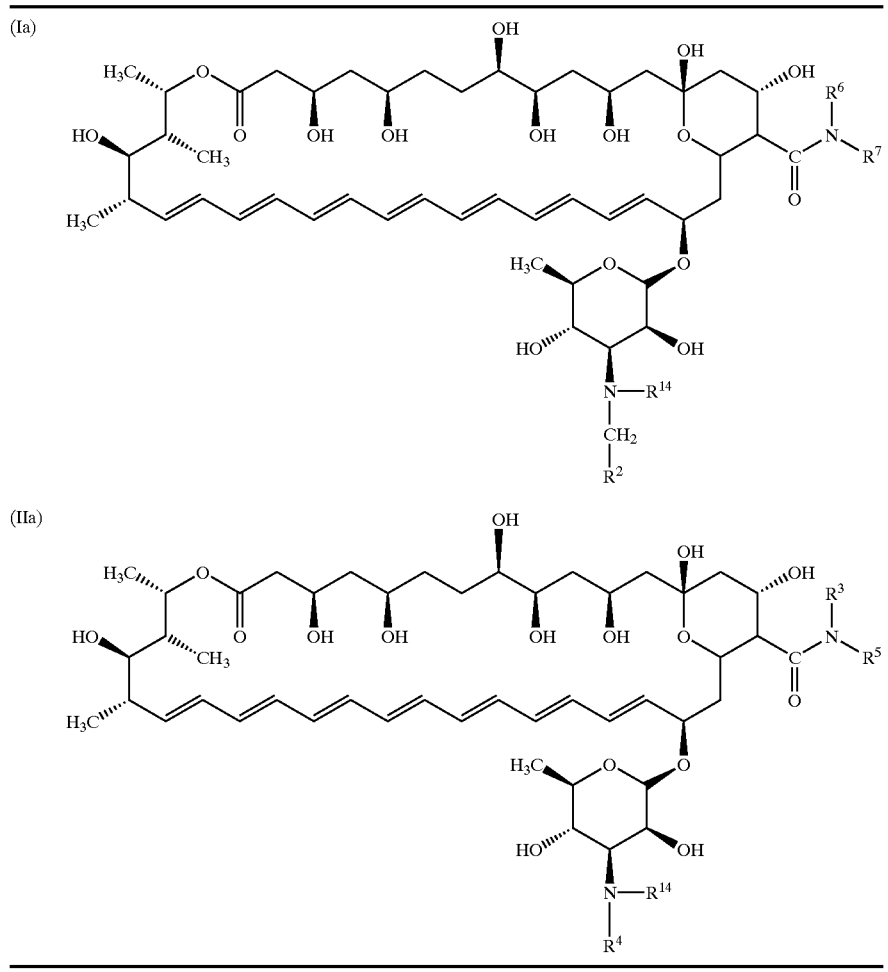

In the amide derivatives of structural formula (I), the carbohydrate residue CH$_2$—R$^2$ may be any number of saccharide units in length, and typically ranges from 1 to about 100 saccharide units. Thus, the carbohydrate residue can be a monosaccharide, a disaccharide, an oligosaccharide comprising from three to tens of saccharide units or a polysaccharide comprising from tens to 30, 40, 50, 60, 100, several hundred, several thousand or even more, saccharide units. In most instances, the carbohydrate residue will be a mono-, di- or oligosachharide. However, as it has been discovered that substituting the amino sugar residue of AmB with large polymers does not deleteriously affect the antifungal activity of the compound, carbohydrate residue CH$_2$—R$^2$ may be a large, water-insoluble polysaccharide and still retain antifungal activity. Polyene macrolide amide derivatives including large polysaccharides that have low water-solubility for carbohydrate residue CH$_2$—R$^2$ may be used topically or as antifungals in non-aqueous environments. Alternatively, the water-solubility characteristics of the compound may be improved by selecting a substituent R$^3$ that has a high water-solubility, such as a substituent that is highly polar, as will be discussed in more detail below. As the amide derivatives of formula (I) comprise water-solubility increasing substituents at the amide nitrogen, a significant advantage of the compounds of the invention is the ability to selectively tune their water-solubility through the choice of amide nitrogen substituents.

The carbohydrate residue CH$_2$—R$^2$ may be a homopolymer, in which all saccharide units are the same, or it may be a heteropolymer comprising mixtures of different saccharide units. The carbohydrate residue may be branched or linear, and, as will be discussed in more detail below, the saccharide units may be, independently of one another, in a cyclic conformation, a linear conformation or in a mixture of cyclic and linear conformations. Moreover, subject only to the constraints of the Amadori rearrangement reaction used to synthesize the polyene macrolide amide derivatives of formula (I), the saccharide units of carbohydrate residue CH$_2$—R$^2$ may be substituted with a variety of different substituents. These substituents may be used to impart the derivatives of the invention with desirable properties, such as, for example, improved water-solubility, lower toxicity, etc., and will be apparent to those of skill in the art.

As will be discussed in more detail in connection with the methods of synthesizing the amide derivatives of formula (I), it will be appreciated that carbohydrate residue CH$_2$—R$^2$ is produced via an Amadori rearrangement of an appropriate reducing carbohydrate, typically a reducing sugar. Therefore, the carbohydrate residue CH$_2$—R$^2$ of the derivatives of formula (I) has a structure that is different from the reducing carbohydrate used as a reactant in the Amadori rearrangement reaction that yields the polyene macrolide amide derivatives of formula (I). The principles of the Amadori rearrangement reaction and the requirements of reducing carbohydrates that can undergo an Amadori rearrangement are well-known and well understood. Briefly, the rearrangement and the requirements of the reducing carbohydrates, exemplified with a monosaccharide, are illustrated below:

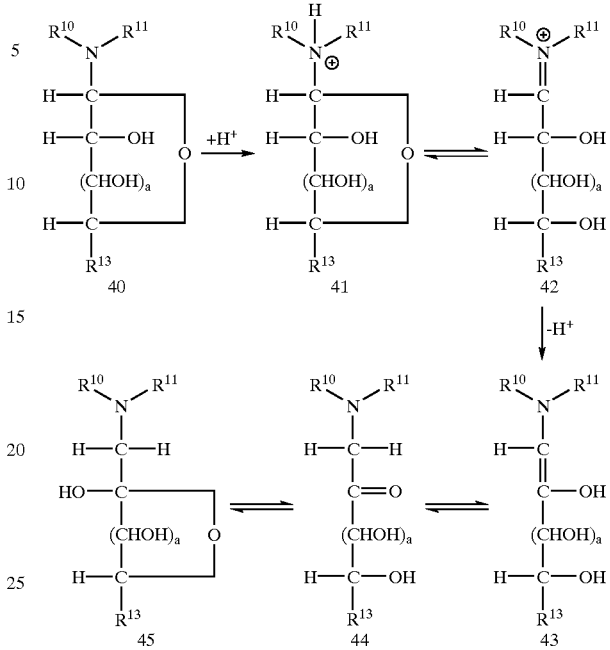

Amadori Rearrangement

The requirements of reducing carbohydrates which can undergo the rearrangement are defined by the various R groups. Generally, the carbohydrate reactant is an aldose, and the hydroxy group at the 2-position must be present and unblocked. In compounds 40, 41, 42, 43, 44 and 45, a is an integer from 0 up to virtually any number, where a is 0 only in open chain conformers; R$^{10}$ is hydrogen, alkyl, alkylidene, cycloalkyl, arylalkyl, aryl, glycosyl or polymer, but not acyl or a strongly electron-withdrawing radical; R$^{11}$ is hydrogen, alkyl, alkylidene, arylalkyl, but not aryl when R$^{10}$ is aryl and, in addition, the combination of (R$^{10}$+R$^{11}$) in the reacting amine should not sterically hinder the nitrogen atom; and R$^{13}$ is hydrogen, —CH$_2$OH, —CH$_3$, —COOH, —CONHR, —COO$^-$M$^+$, and the like, where R is, for example, hydrogen or alkyl and M$^+$ represents a metal ion, such as Na$^+$, K$^+$, etc. Any reducing carbohydrate having these attributes can undergo an Amadori rearrangement to yield the polyene macrolide amide derivatives of formula (I). For additional guidance regarding the requirements of the Amadori rearrangement, see Hodge & Fisher, "Amadori Rearrangement Products," In: *Methods in Carbohydrate Chemistry, Volume II, Reactions of Carbohydrates*, Whistler & Wolfram, Eds., pp. 99–107, Academic Press, Inc., New York (1963). Skilled artisans will be able to select an appropriate reducing carbohydrate reactant to obtain an amide derivative according to formula (I) that has the desired carbohydrate residue CH$_2$—R$^2$. TABLE 1 presents an exemplary list of reducing carbohydrates that are capable of undergoing an Amadori rearrangement that may be used to produce polyene macrolide amide derivatives of structural formula (I). Other carbohydrates having appropriate properties will be apparent to those of skill in the art.

Those of skill in the art will appreciate that the above-illustrated Amadori rearrangement illustrates only the carbohydrate. For the reactions and polyene macrolide amide derivatives described herein, in Compounds 40, 41, 42, 43, 44 and 45, $R^{10}$ corresponds to $R^1$—C(O) and $R^{11}$ corresponds to $R^{14}$ of structural formula (I).

TABLE 1

Exemplary Reducing Carbohydrates for Amadori Reaction allose
altrose
arabinose
cellobiose
fucose
galactose
glucose
3-O-methyl-glucose
4-fluoro-4-deoxy-glucose
gulose
idose
lactose
lyxose
maltopentose
maltose
mannose
N-(2,3,5-trihydroxy-6-hydroxymethyl-tetrahydro-pyran-4-yl)-acetamide
ribose
talose
xylose The absolute stereochemistry of the carbohydrate residue $CH_2$—$R^2$ in the amide derivatives of structural formula (I) is not critical to success. Thus, the reducing carbohydrates used as reactants, e.g., the reducing carbohydrates of TABLE 1, may be D-isomers, L-isomers or mixtures of D- and L-isomers, depending upon the desired stereochemistry of the resultant product. If optically pure compounds are desired, reducing carbohydrates that are pure optical isomers should be selected as reactants for the Amadori rearrangement reaction.

The reducing carbohydrates, e.g., the reducing carbohydrates of TABLE 1, may also be either α- or β-conformers, or mixtures of α- and β-conformers. Owing to the mechanism of action of the Amadori rearrangement reaction, corresponding α- and β-conformer reducing carbohydrate reactants will yield the same Amadori product.

As illustrated in the above rearrangement, it will be appreciated that the resultant carbohydrate residue produced by an Amadori rearrangement reaction may be in either a cyclic or linear conformation, or may be a mixture of cyclic and linear conformers. In the specific polyene macrolide amide derivatives of formula (I) illustrated herein, the various carbohydrate residues added via the Amadori rearrangement are shown in their cyclic conformations. However, it will be appreciated that these illustrations are not intended in any way to limit the carbohydrate residue of the illustrated derivatives, or of any polyene macrolide amide derivatives according to structural formula (I), to the cyclic forms. When the carbohydrate residue is a monosaccharide, it may be linear, cyclic or a mixture of linear and cyclic conformers. When the carbohydrate residue is a di-, oligo- or polysaccharide, each monosaccharide unit may be cyclic or linear, or a mixture of cyclic and linear conformers. Thus, the polyene macrolide amide derivatives according to structural formula (I) may be in the form of pure compounds or in the form of mixtures of two or more different conformers. The only requirement is that the polyene macrolide amide derivative, whether a single compound or mixture of different conformers, have antifungal activity as described herein. If desired, pure conformers may be isolated using techniques that are well-known in the art.

In some embodiments, the polyene macrolide derivatives of formula (I) are Amadori rearrangement products in which the reducing carbohydrate reactant is selected from the group consisting of glucose, maltose, cellobiose, lactose, allose, and galactose, in either the α-, β-, D- or L-configurations, or mixtures thereof.

In the polyene macrolide amide derivatives of formula (I), the amide nitrogen has attached thereto and/or includes one or more of the same or different water-solubility increasing substituents, designated as $R^6$ and/or $R^7$. Water-solubility increasing substituents generally comprise groups that have polar characteristics by virtue of including one or more of the same or different heteroatoms. Such heteroatoms are typically selected from the group consisting of O, N, NH and S, although other heteroatoms may be used.

In one embodiment, the water-solubility increasing substituents are hydrocarbons such as linear and branched alkyls, cycloalkyls, aryls and arylalkyls that are substituted with one or more of the same or different polar substituents. Typical polar substituents include, but are not limited to, —OH, —SH, =O (oxo), =S (thioxo), —$NH_2$, =NH (imino), —C(=NH)—$NH_2$ (amidino), —NH—C(=NH)—$NH_2$ (guanidino), —C(O)H, —C(O)OH, —C(O)O$^-M^+$, —C(O)$NH_2$, —$N_3$, —CN, —X, —$CX_3$, etc., where each X is independently a halogen, preferably F, Cl or Br and $M^+$ represents a monovalent counter ion such as $Na^+$, $K^+$, etc. The polar substituted alkyls, cycloalkyls, aryls and arylalkyls may be further optionally substituted with one or more of the same or different non-polar substituents, e.g., alkyls, cycloalkyls, aryls and arylalkyls, etc.; however care should be taken when selecting combinations of polar and non-polar substituents to insure that the overall net character of the water solubility increasing substituent is polar. Preferred polar substituted hydrocarbon water solubility increasing substituents are those that include a plurality of polar substituents, such as, for example ($C_1$–$C_{10}$) alkyls and ($C_3$–$C_{10}$) cycloalkyls that are substituted with a plurality of the same or different polar substituents. In one embodiment, the plurality of polar substituents are, independently of one another, selected from the group consisting of lower alkoxy, methoxy, hydroxy, amino, imino, amidino and guanidino groups.

In another embodiment, the heteroatom(s) is included in the chain of a hydrocarbon such that the water solubility-increasing substituents are linear and branched heteroalkyls (e.g., ethers, thioethers, sulfonamides, alkylamines, etc.), cycloheteroalkyls (e.g., imidazolidine, morpholine, piperazine, piperidine, pyrazolidine, pyrrolidine, quinuclidine, etc.), heteroaryls (e.g., chromane, chromene, furan, imidazole, indazole, indole, indoline, indolizine, isobenzofuran, isochromene, isoindole, isoindoline, isoquinoline, isothiazole, isoxazole, naphythyridine, phenanthroline, phthalazine, pteridine, purine, pyran, pyrazine, pyrazole, pyridazine, pyridine, pyrimidine, pyrrole, pyrrolizine, quinazoline, quinoline, quinoxaline, thiophene, xanthene, etc.) and heteroarylalkyls (including, for example, compounds of the formula —$(CH_2)_m$—$R^{22}$, where m is an integer from 1 to 6 and $R^{22}$ is a heteroaryl). One or more of the carbon atoms and/or heteroatoms (e.g., N, NH, etc.) of these heteroalkyl, cycloheteroalkyl, heteroaryl and heteroarylalkyl groups may be further substituted with one or more of the same or different polar or non-polar substituents, as described above. Again, the various polar and non-polar substituents should be selected such that the overall net character of the resultant water-solubility increasing substituent will be polar. Preferred water-solubility increasing substituents of this type are those which include one or two of the same or different heteroatoms, and which are optionally substituted at one or more of the carbon atoms or heteroatoms, as previously described. In one embodiment, the water solubility increasing substituents are saturated or unsaturated 5–6 membered rings that include one or two of the same or different heteroatoms, preferably heteroatoms selected from the group consisting of O, N, NH and S. These heteroatom-containing rings may be optionally substituted with one or more of the same or different polar or non-polar substituents, as previously described. When such 5- or 6-membered rings are substituted with non-polar substituents, the rings are usually mono-substituted and the substituent is typically selected from the group consisting of $(C_1-C_6)$ alkyl, $(C_1-C_{3-4})$ alkanyl, $(C_5-C_6)$ aryl, phenyl, 6- to 9-membered arylalkyl and benzyl. The substituted or unsubstituted heteroatom-containing ring may be attached directly to the amide nitrogen or may be spaced away from the amide nitrogen via an amine, alkylamine or alkyldiyl spacer moiety, preferably a —NH—, $(C_1-C_{10})$ alkyldiyl,$(C_1-C_{10})$ alkyleno or $(C_1-C_6)$ alkano spacer moiety.

In still another embodiment, $R^6$ and $R^7$ are taken together such that the amide nitrogen to which they are bonded is included as a member of a saturated or unsaturated ring which may optionally include one or more of the same or different additional heteroatoms and/or which is optionally further substituted at one or more of the ring carbon or heteroatoms with the same or different polar or non-polar substituents, as previously described. In one embodiment, such rings are 5 or 6-membered rings. When such 5- or 6-membered rings are substituted with non-polar substitutents, the rings are usually mono-substituted and the substituent is typically selected from the group consisting of $(C_1-C_6)$ alkyl, $(C_1-C_{3-4})$ alkanyl, $(C_1-C_6)$ aryl, phenyl, 6- to 9-membered arlyalkyl and benzyl.

In embodiments of the compounds of structural formulae (I) and (II) which include only a single water-solubility increasing substituent at the amide nitrogen, the other amide nitrogen substituent may be hydrogen or a non-polar substituent, as previously described. In one embodiment, the non-polar substituent is a lower alkyl, $(C_1-C_{3-4})$ alkyl, lower alkanyl or $(C_1-C_{3-4})$ alkanyl As will be appreciated from the above discussion, the composition of the water-solubility increasing substituents is not critical to success. Further non-limiting examples of water-solubility increasing substituents that are useful include polyhydroxylated alkyls, mono-, di-, oligo- and polysaccharides, polyalkylene glycols (e.g., polyethylene glycol, polypropylene glycol, etc.) and polyalkylene oxides.

In one specific embodiment, the polyene macrolide amide derivatives are compounds according to structural formula (I) in which:

N—$R^1$—C(O), $CH_2$—$R^2$ and $R^{14}$ are as previously described for structural formula (I);

either: (i) $R^6$ is selected from the group consisting of hydrogen, $(C_1-C_6)$ alkyl, $(C_1-C_6)$ alkyl substituted with one or more of the same or different $R^{10}$ groups, —$[(CH_2)_n$—$NH]_p$—$(CH_2)_n$—$NR^{15}R^{16}$, —NH—$[(CH_2)_n$—$NH]_p$—$(CH_2)_p$—$NR^{15}R^{16}$, —$[(CH_2)_n$—$NH]_p$—$(CH_2)_n$—$R^{17}$ and —NH—$[(CH_2)_n$—$NH]_p$—$(CH_2)_p$—$R^{17}$ and $R^7$ is selected from the group consisting of $(C_1-C_6)$ alkyl substituted with one or more of the same or different $R^{10}$ groups, —$[(CH_2)_n$—$NH]_p$—$(CH_2)_n$—$NR^{15}R^{16}$, —NH—$[(CH_2)_n$—$NH]_p$—$(CH_2)_p$—$NR^{15}R^{16}$, —$[(CH_2)_n$—$NH]_p$—$(CH_2)_n$—$R^{17}$ and —NH—$[(CH_2)_n$—$NH]_p$—$(CH_2)_p$—$R^{17}$; or (ii) $R^6$ and $R^7$, taken together with the amide nitrogen atom to which they are bonded, form a 5- or 6-membered saturated or unsaturated ring which optionally includes one or more of the same or different additional heteroatoms selected from the group consisting of O, N, NH and S and/or which is optionally substituted at one or more ring carbon or heteroatoms with the same or different substituents selected from the group consisting of $R^{10}$, $(C_1-C_6)$ alkyl, $(C_1-C_6)$ alkoxy, —$(CH_2)_n$—$R^{10}$, $(C_5-C_6)$ aryl, phenyl, 6- to 9-membered arylalkyl and benzyl;

each $R^{10}$ is independently selected from the group consisting of —OH, =O (oxo), —$NH_2$ (amino), =NH (imino), —C(=NH)—$NH_2$ (amidino) and —NH—C(=NH)—$NH_2$ (guanidino);

either: (i) $R^{15}$ and $R^{16}$ are each independently selected from the group consisting of hydrogen, $(C_1-C_6)$ alkyl and $(C_1-C_6)$ alkyl independently substituted with one or more of the same or different $R^{10}$ groups; or (ii) $R^{15}$ and $R^{16}$, taken together with the nitrogen atom to which they are bonded, form a 5- or 6-membered saturated or unsaturated ring which optionally includes one or more of the same or different additional heteroatoms selected from the group consisting of O, N, NH and S and/or which is optionally substituted at one or more ring carbon or heteroatoms with the same or different substituents selected from the group consisting of $R^{10}$, $(C_1-C_6)$ alkyl, $(C_1-C_6)$ alkoxy, —$(CH_2)_n$—$R^{10}$, $(C_5-C_6)$ aryl, phenyl, 6- to 9-membered arylalkyl and benzyl;

$R^{17}$ is a 5- or 6-membered saturated or unsaturated ring which optionally includes one or more of the same or different additional heteroatoms selected from the group consisting of O, N, NH and S and/or which is optionally substituted at one or more ring carbon or heteroatoms with the same or different substituents selected from the group consisting of $R^{10}$, $(C_1-C_6)$ alkyl, $(C_1-C_6)$ alkoxy, —$(CH_2)_n$—$R^{10}$, $(C_5-C_6)$ aryl, phenyl, 6- to 9-membered arylalkyl and benzyl;

each n is independently an integer from 1 to 6; and each p is independently an integer from 0 to 6.

In one specific embodiment of the above-described compounds, $R^{15}$ and $R^{16}$ are defined according to alternative (ii) and form a saturated ring which optionally includes additional heteroatoms and which is optionally substituted, as described above. In another specific embodiment, $R^{17}$ is a 5- to 6- membered heteroaryl ring, optionally substituted as described above.

In another embodiment, the polyene amide derivatives of structural formula (I) and/or any of the above-described specific embodiments thereof, where applicable, have one or more features selected from the group consisting of:

N—$R^1$—C(O) is a polyene backbone derived from AmB or nystatin;

$CH_2$—$R^1$ is a mono-, di- or oligosaccharide;

$R^6$ is hydrogen; and/or $R^{14}$ is hydrogen.

In still another embodiment, the polyene macrolide derivatives of the invention are compounds according to structural formula (I) in which:

$R^6$ is hydrogen;

$R^7$ is selected from the group consisting of —NH—$NR^{15}R^{16}$, —$(CH_2)_n$—$NR^{15}R^{16}$, —$(CH_2)_n$—$R^{17}$ and ($C_1$-$C_6$) alkyl substituted with one or more amino or hydroxyl groups;

$R^{15}$ and $R^{16}$, taken together with the nitrogen atom to which they are bonded, form a 5- or 6-membered saturated or unsaturated ring which optionally includes one or more additional heteroatoms selected from the group consisting of O, S, N and NH and/or which is optionally substituted at one or more ring carbon or heteroatoms with the same or different $R^{10}$, ($C_1$-$C_6$) alkyl, ($C_1$-$C_6$) alkoxy, ($C_5$-$C_6$) aryl, phenyl, 6- to 9-membered arylalkyl or benzyl groups;

$R^{17}$ is a 5- or 6-membered heteroaryl which is optionally substituted with one or more of the same or different ($C_1$-$C_6$) alkyl, ($C_1$-$C_6$) alkoxy, ($C_5$-$C_6$) aryl, phenyl, 6- to 9-membered arylalkyl or benzyl groups; and all other variables are as defined for structural formula (I).

In still another embodiment, the polyene macrolide amide derivatives of the invention are compounds according to structural formula (I) in which:

$R^6$ and $R^7$, taken together with the nitrogen atom to which they are bonded, form a 5- to 6-membered cycloheteroalkyl ring optionally substituted with one or more, preferably one, substituent selected from the group consisting of ($C_1$-$C_6$) alkyl, ($C_1$-$C_6$) alkoxy, —$(CH_2)_n$—$R^{10}$, ($C_1$-$C_6$) aryl, phenyl, 6- to 9-membered arylalkyl and benzyl;

$R^{10}$ is amino or hydroxy; and all other variables are as defined for structural formula (I).

In one embodiment, the cycloheteroalkyl ring is a morpholine or a piperazine ring. When substituted, the piperazine ring is preferably substituted at the N-position.

Exemplary water-solubility increasing substituents useful in the context of the polyene macrolide amide derivatives according to structural formula (I) are illustrated with reference to compounds (100)–(122) and (127)–(147), infra. Additional exemplary water solubility increasing substituents are described in U.S. Pat. No. 5,296,597 to Bruzzese et al. (see especially Cols. 6–10 and Table 1), U.S. Pat. No. 5,298,495 to Bruzzese et al. (see especially Tables 1 and 2) and Bruzzese et al., 1996, Eur. J. Med. Chem. 31:965–972 (see especially Table 1), the disclosures of which are incorporated herein by reference.

Exemplary polyene macrolide amide derivatives according to structural formula (I) in which carbohydrate $CH_2$—$R^2$ is an Amadori rearrangement product using α-D-glucose as the reducing carbohydrate include the following compounds:

(100)

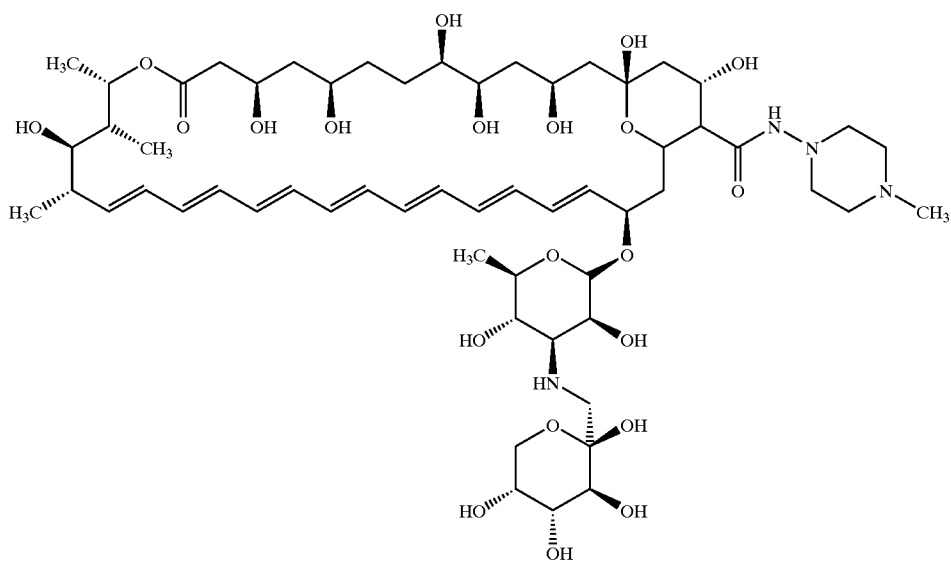

(101)
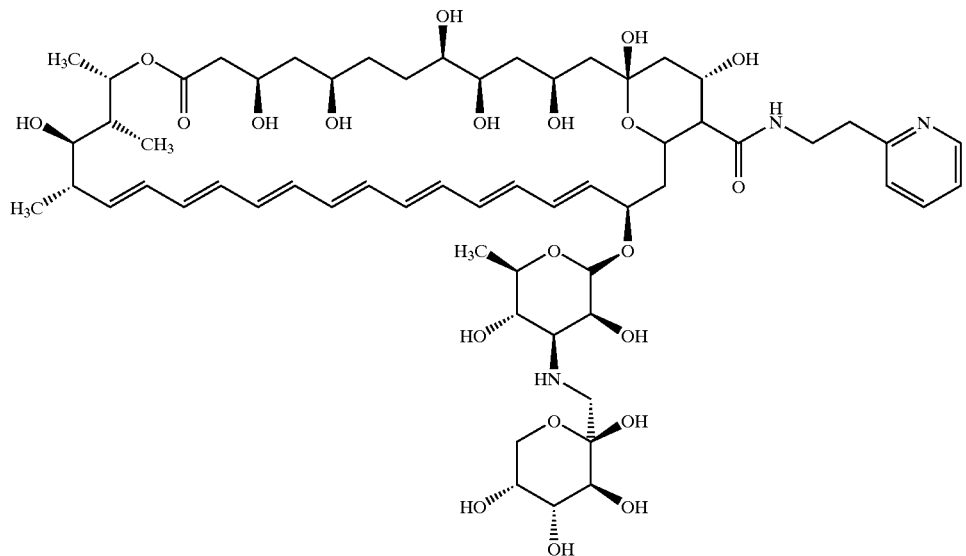
(102)
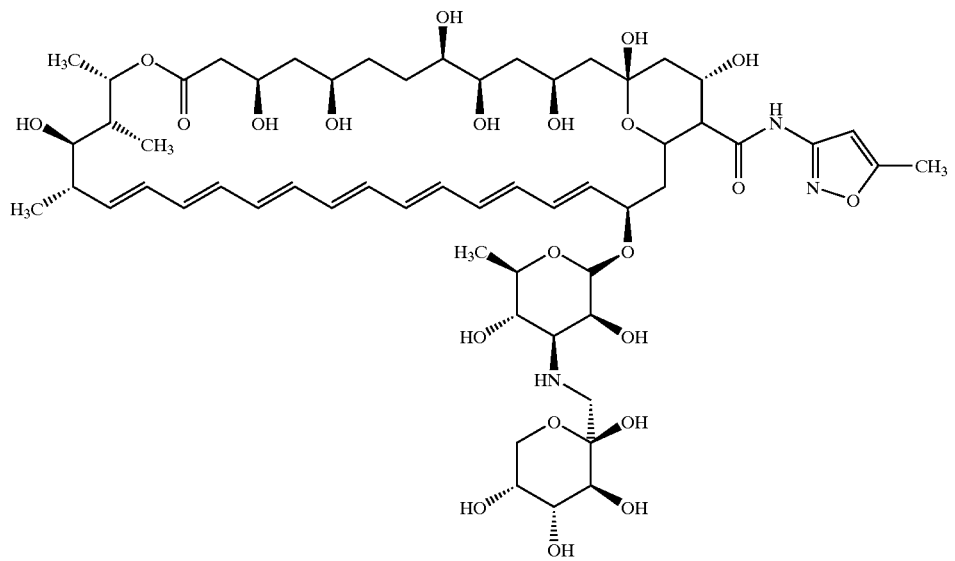

(103)
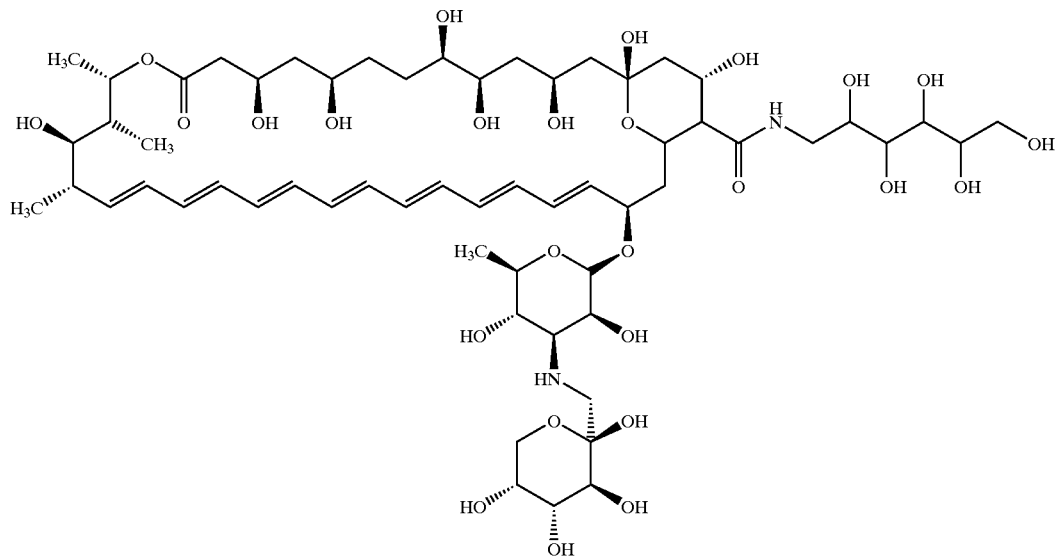
(104)
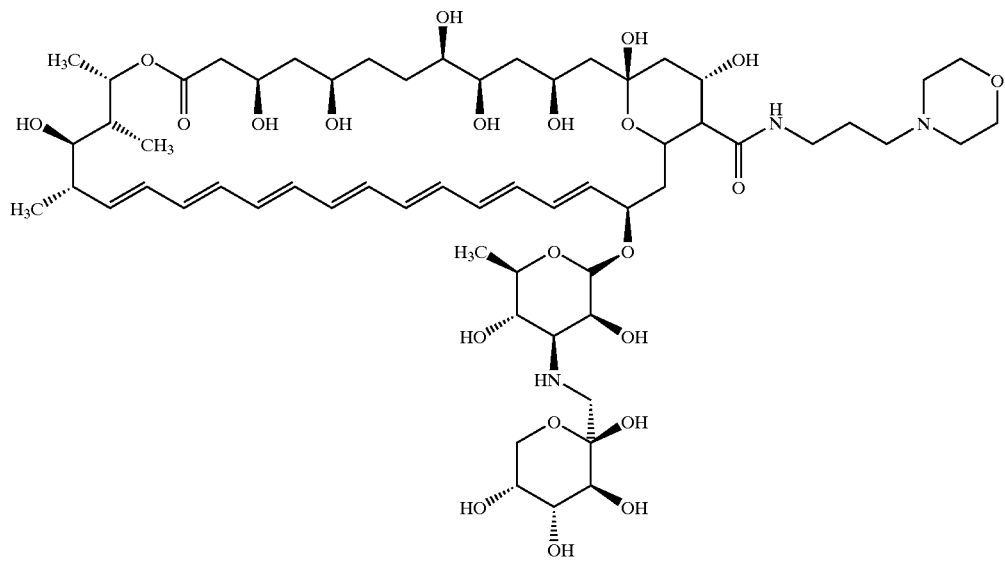

(105)
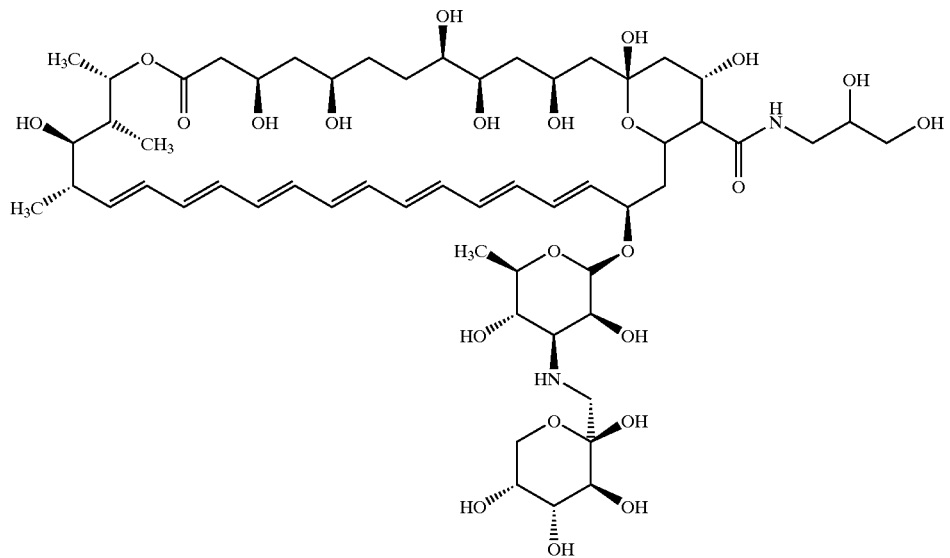
(106)
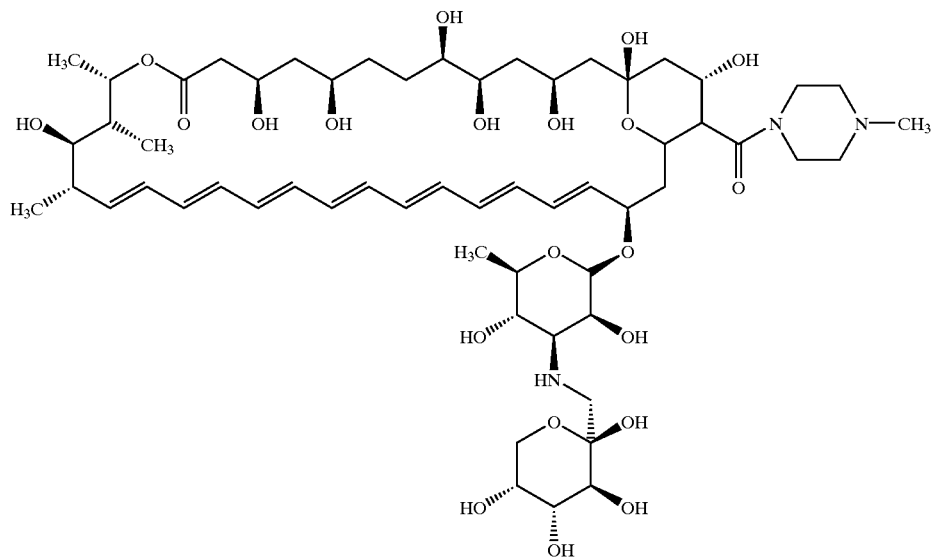

(107)
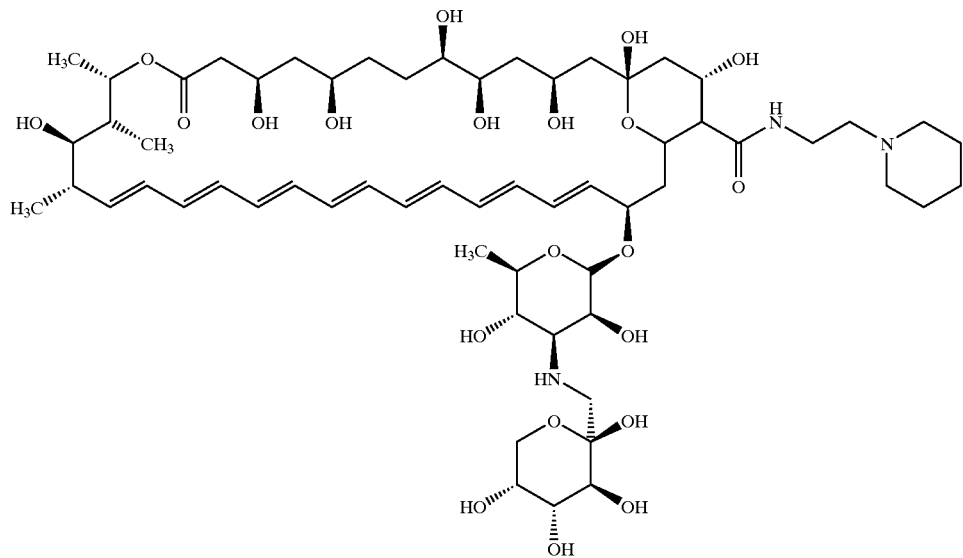
(127)
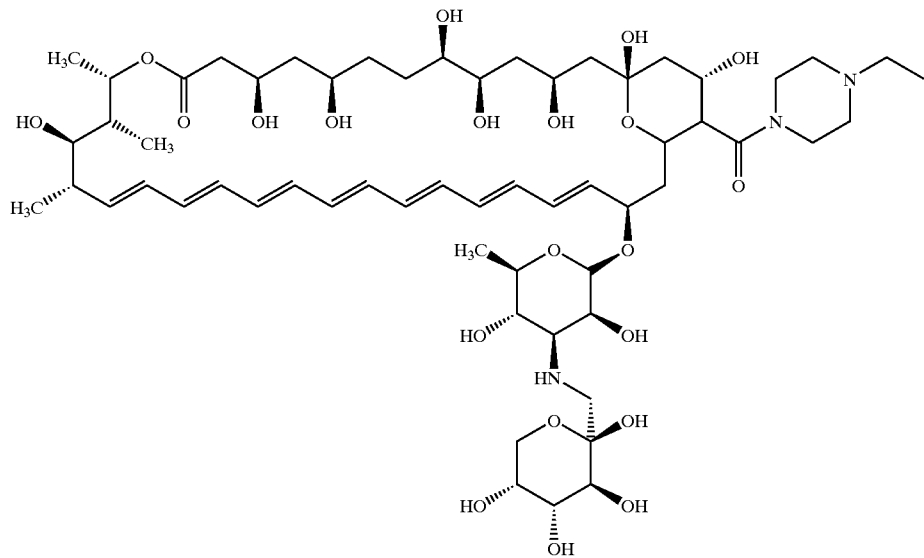

(128)
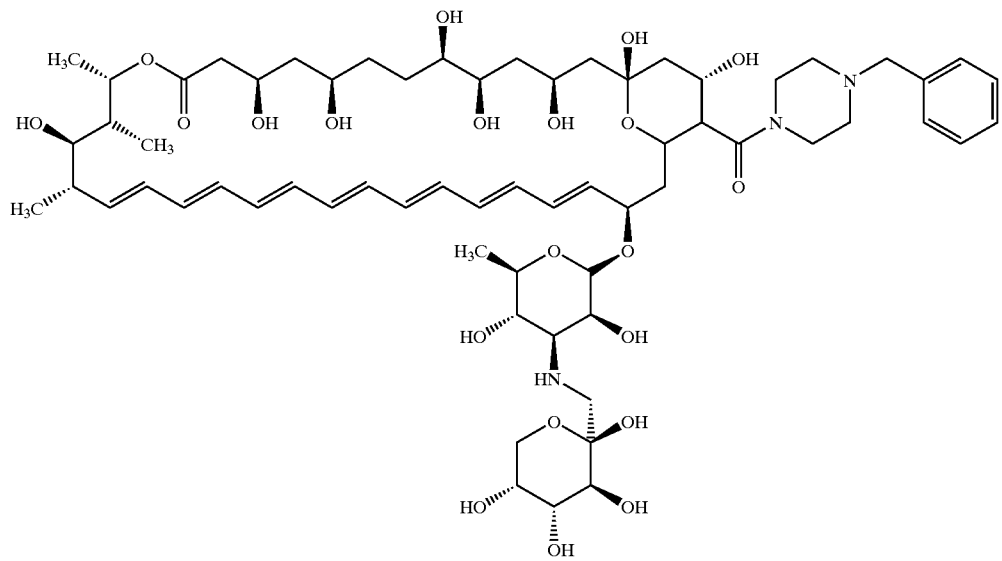
(129)
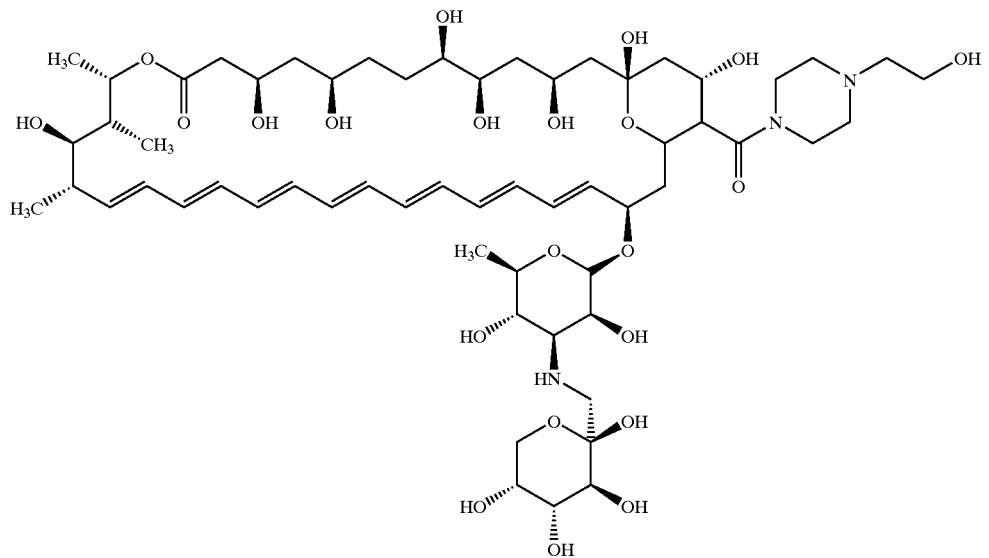

(130)
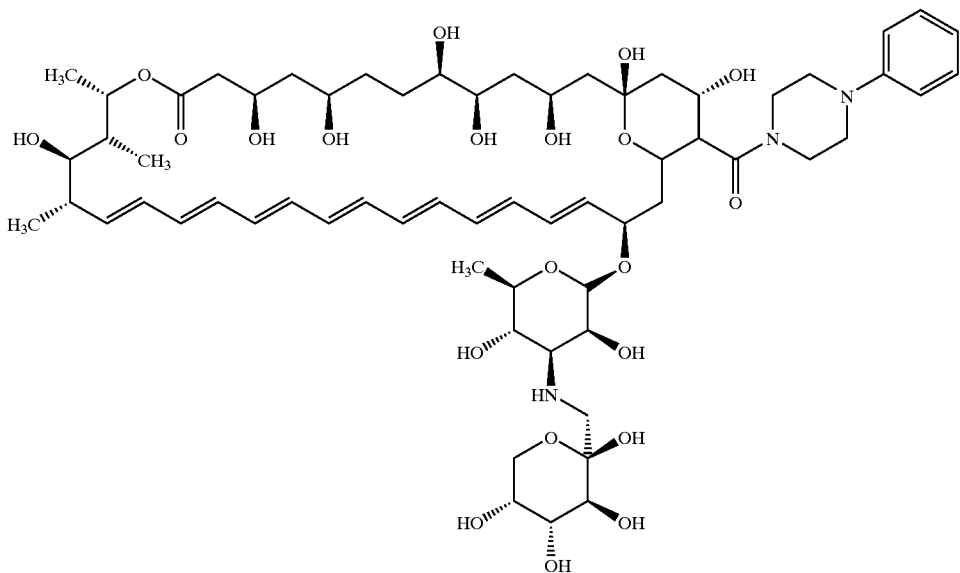
(131)
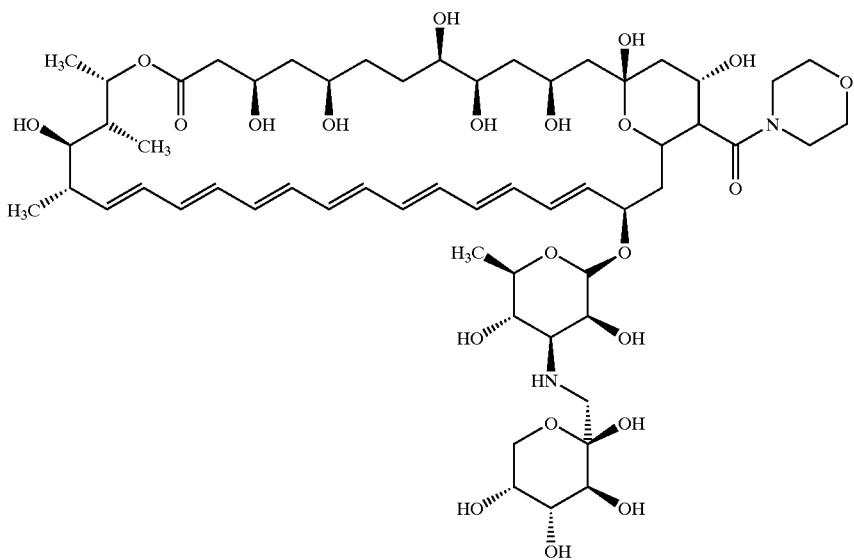
Also exemplified are the corresponding nystatin derivatives of Compounds (100) through (107) and (127) through (131).
Exemplary polyene macrolide amide derivatives according to structural formula (I) in which carbohydrate $CH_2$—$R^2$ is an Amadori rearrangement product using D-galactose as the reducing carbohydrate include the following compounds:

(108)
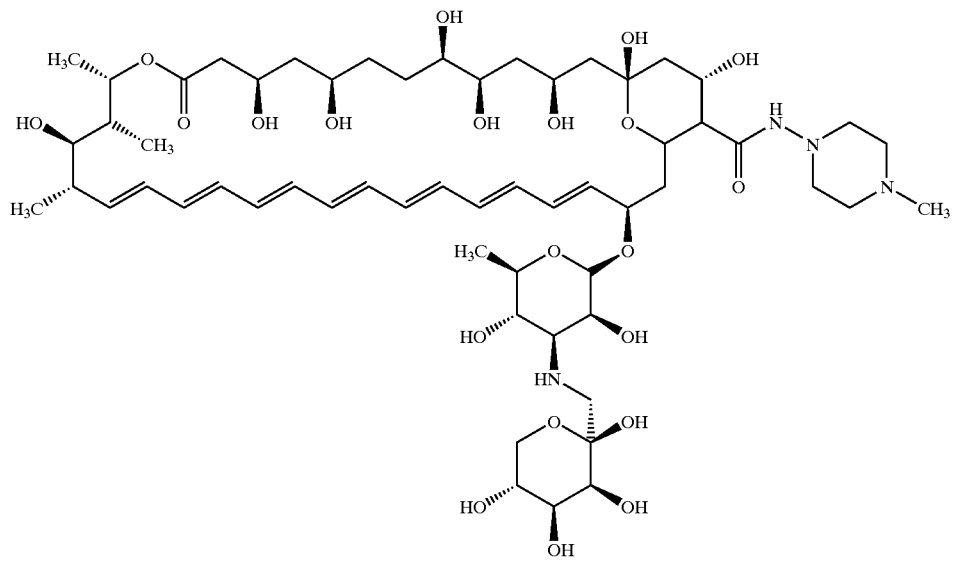
(109)
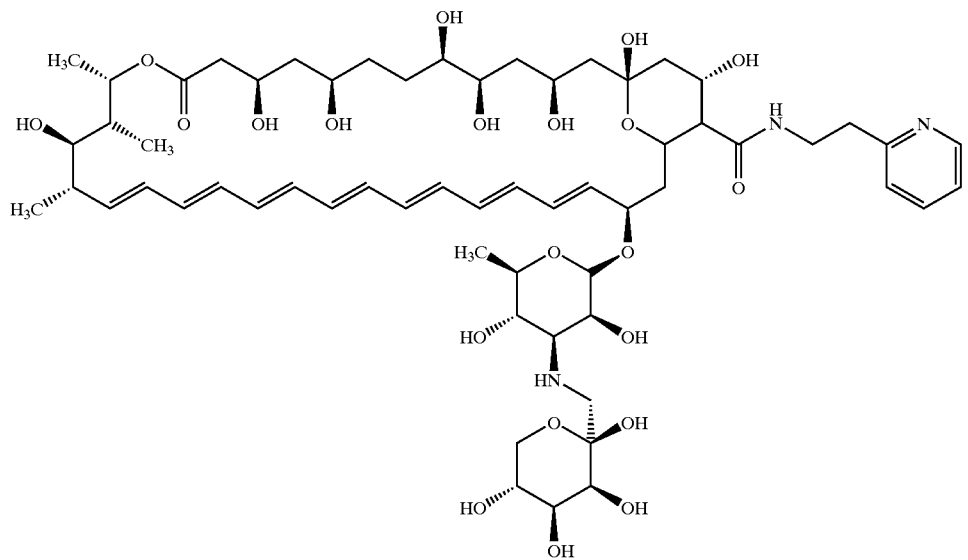

(110)
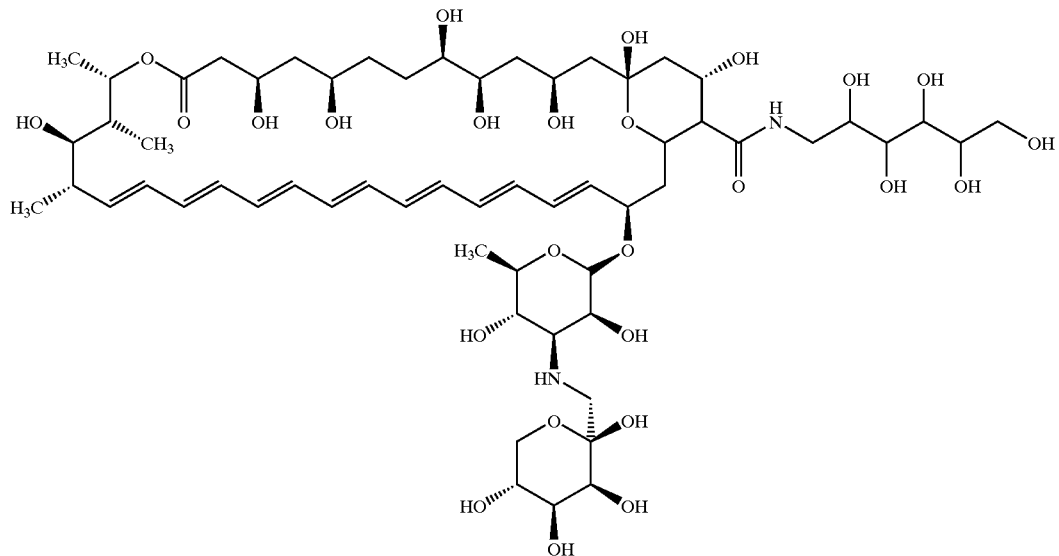
(111)
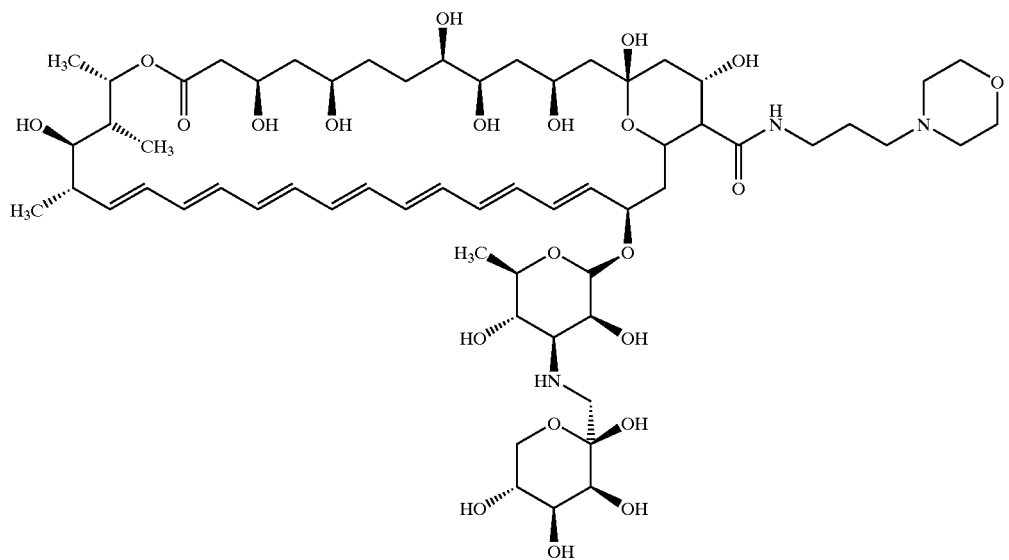

(112)
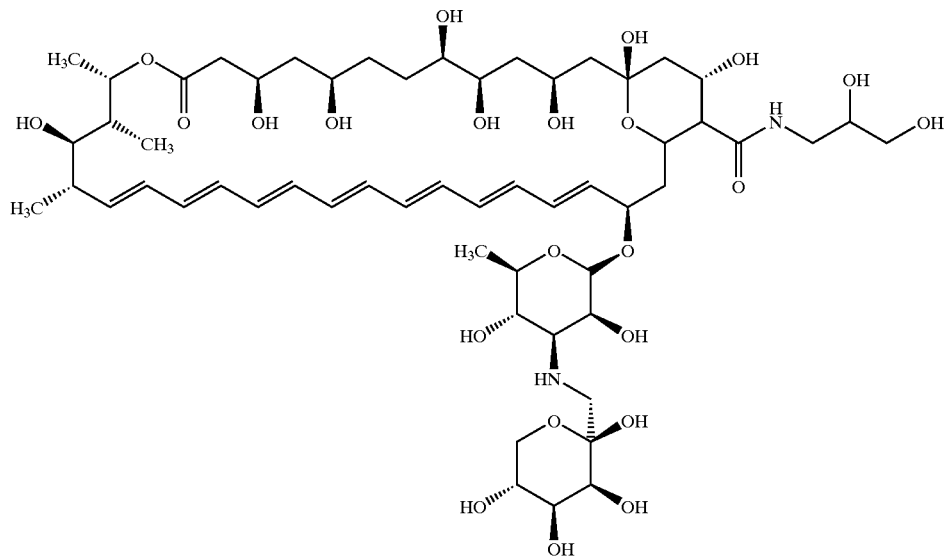
(113)
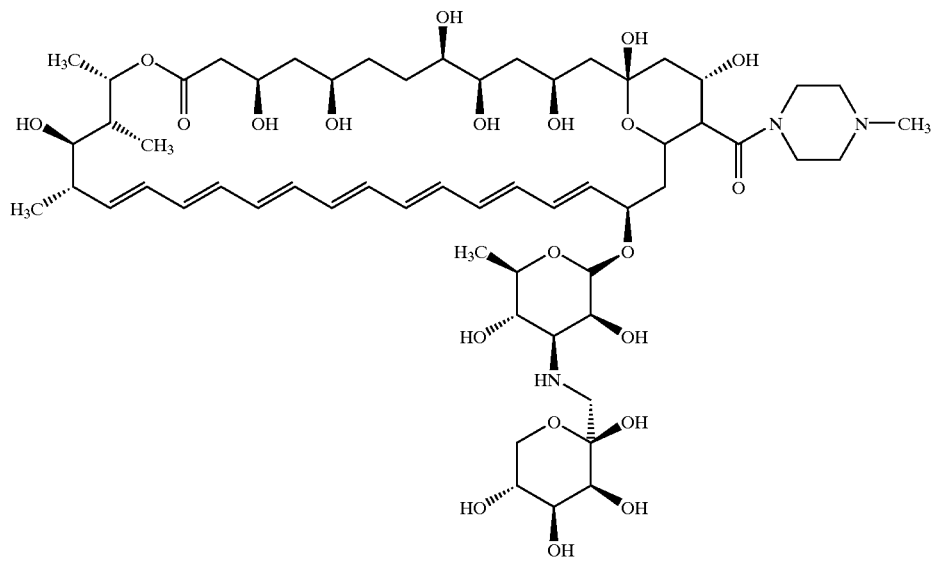

(114)
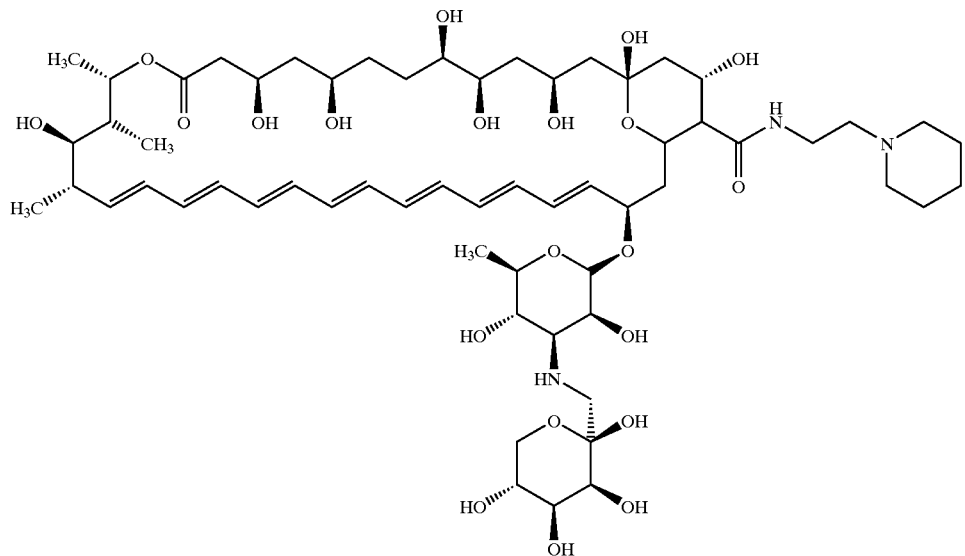
(115)
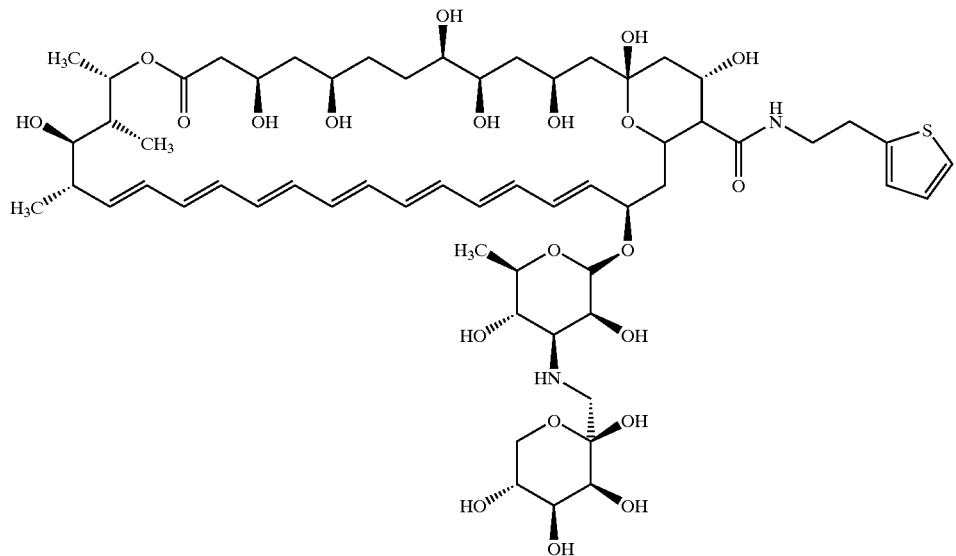

(132)
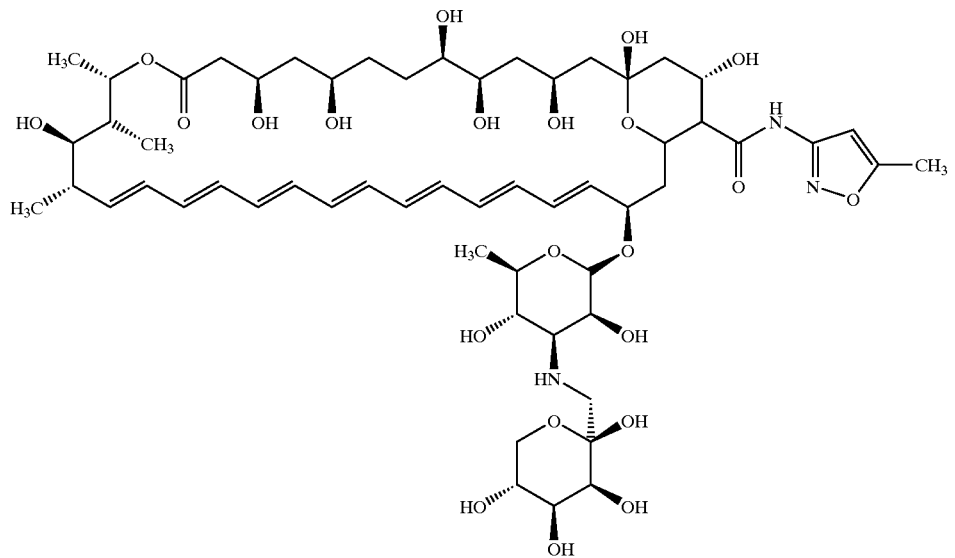
(133)
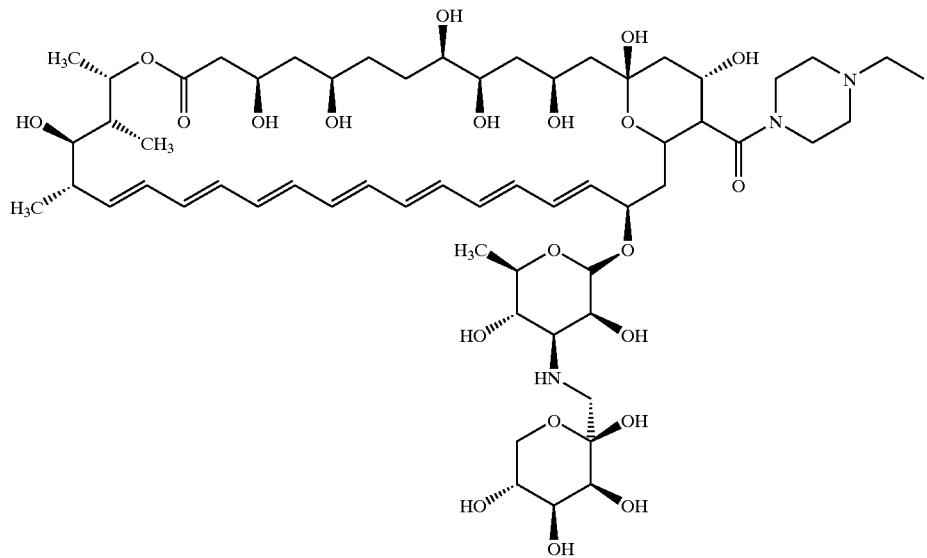

(143)
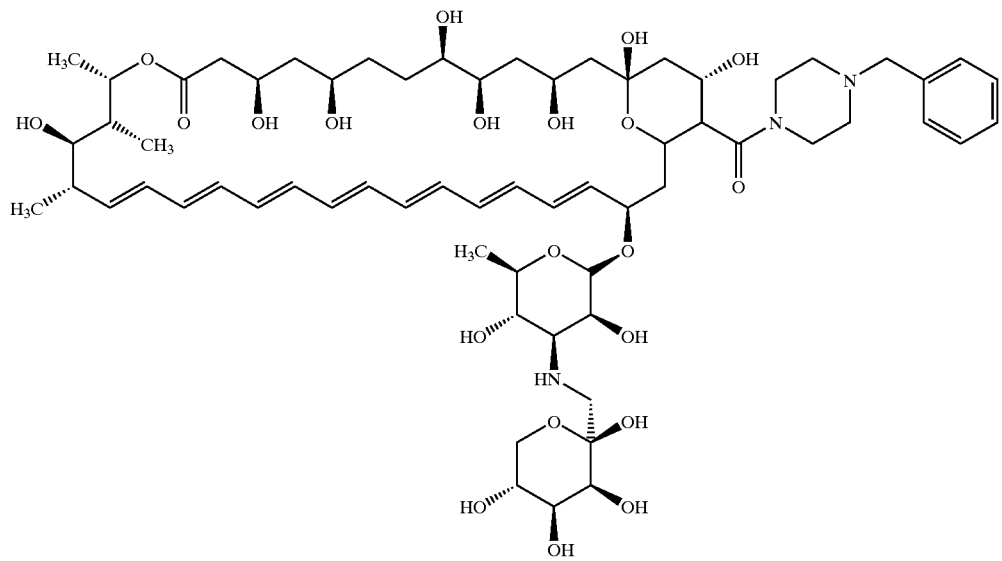
(135)
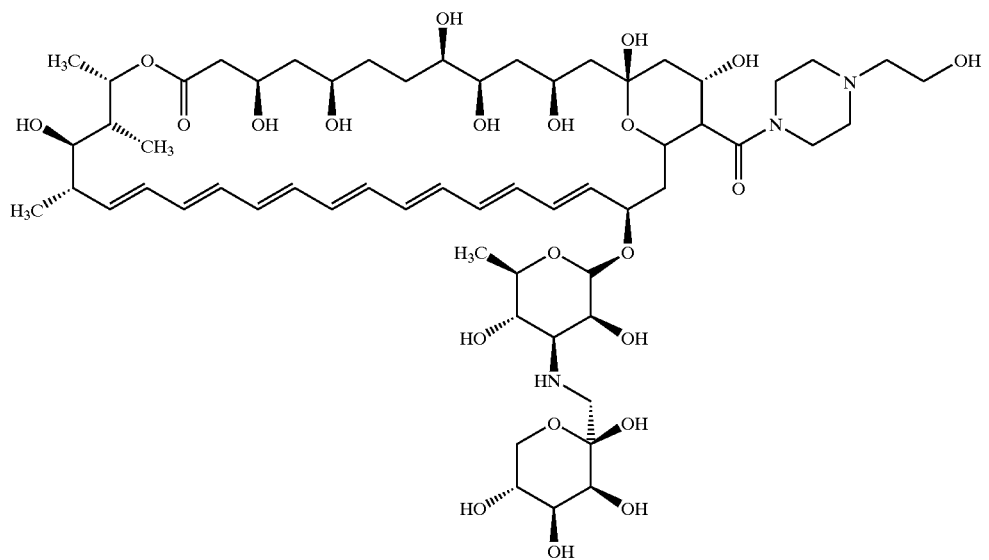

(136)
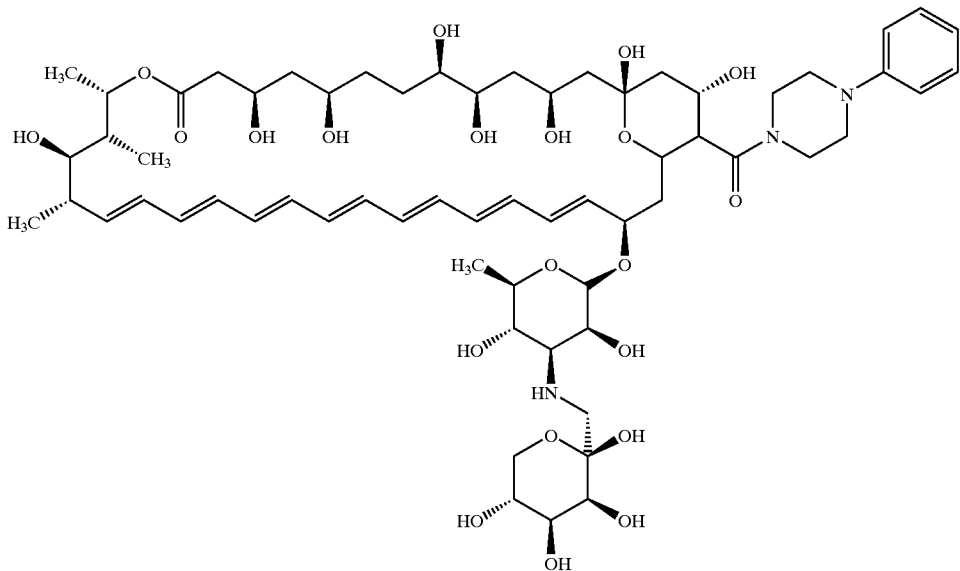
(137)
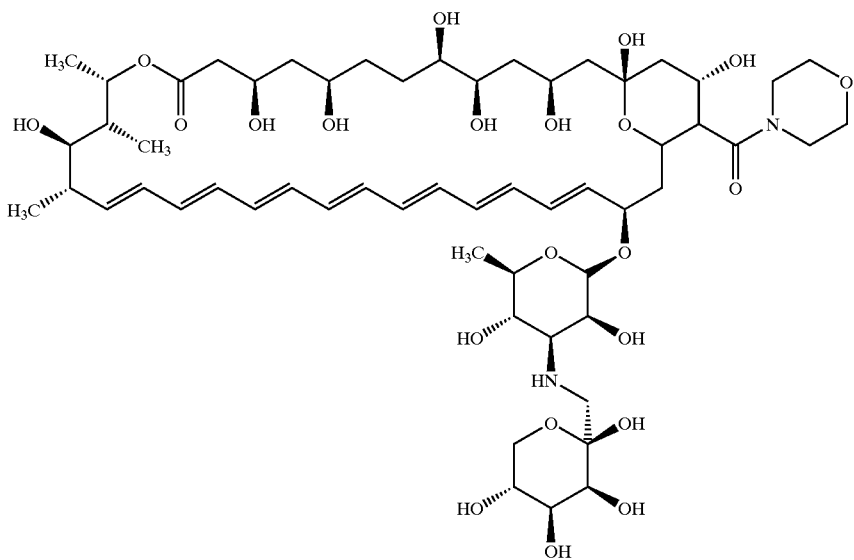
Also exemplified are the corresponding nystatin derivatives of Compounds (108) through (115) and (132) through (137).
Exemplary polyene macrolide amide derivatives according to structural formula (I) in which carbohydrate $CH_2$—$R^2$ is an Amadori rearrangement product using D-maltose as the reducing carbohydrate include the following compounds:

(116)
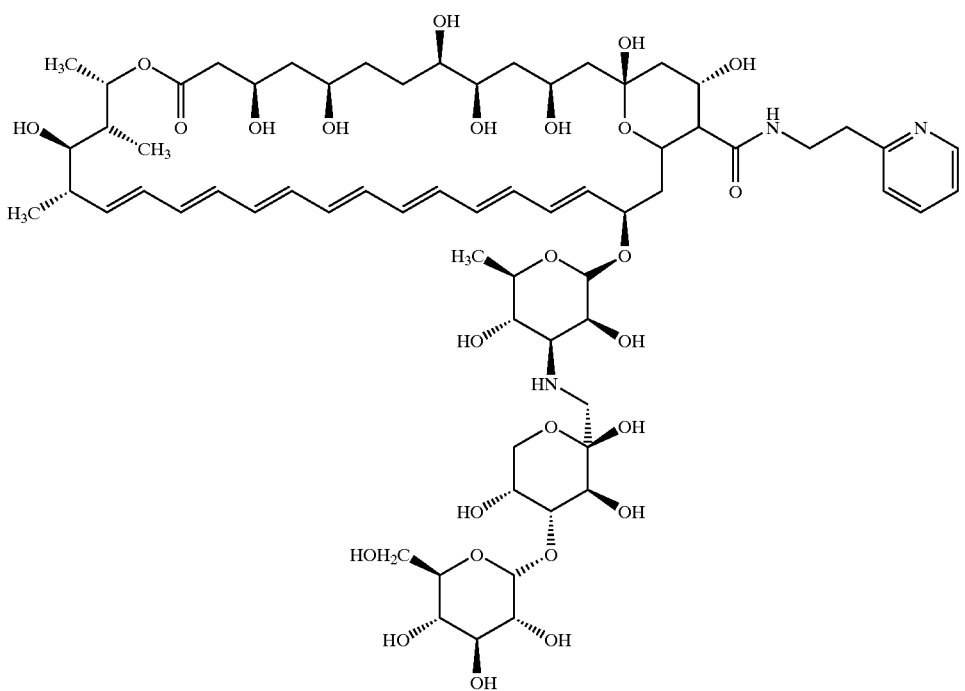
(117)
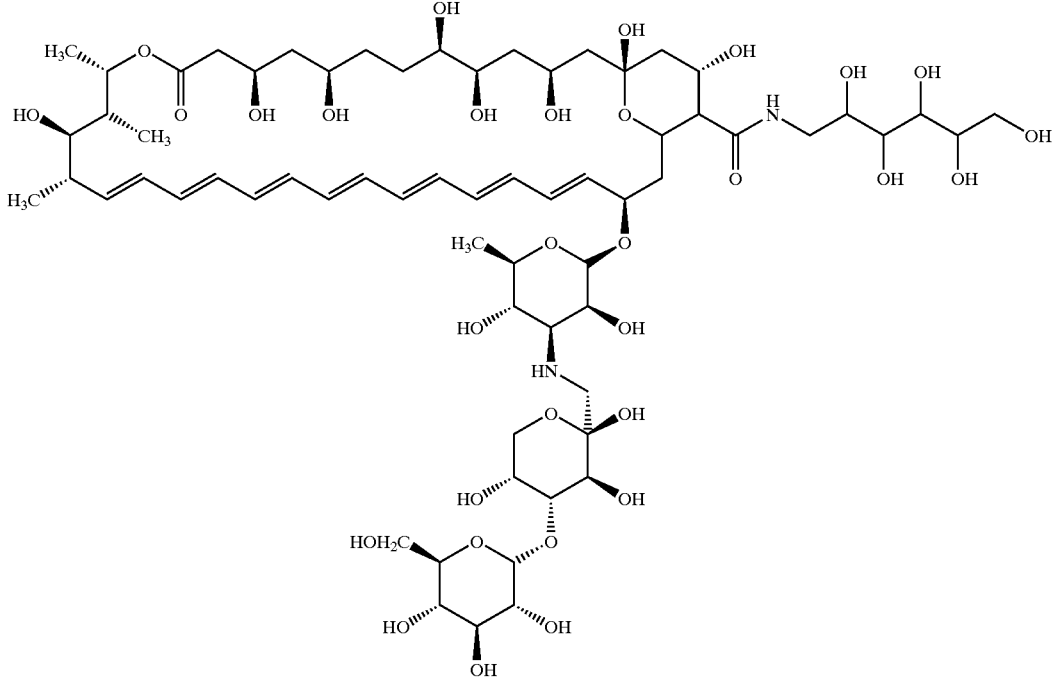

(118)
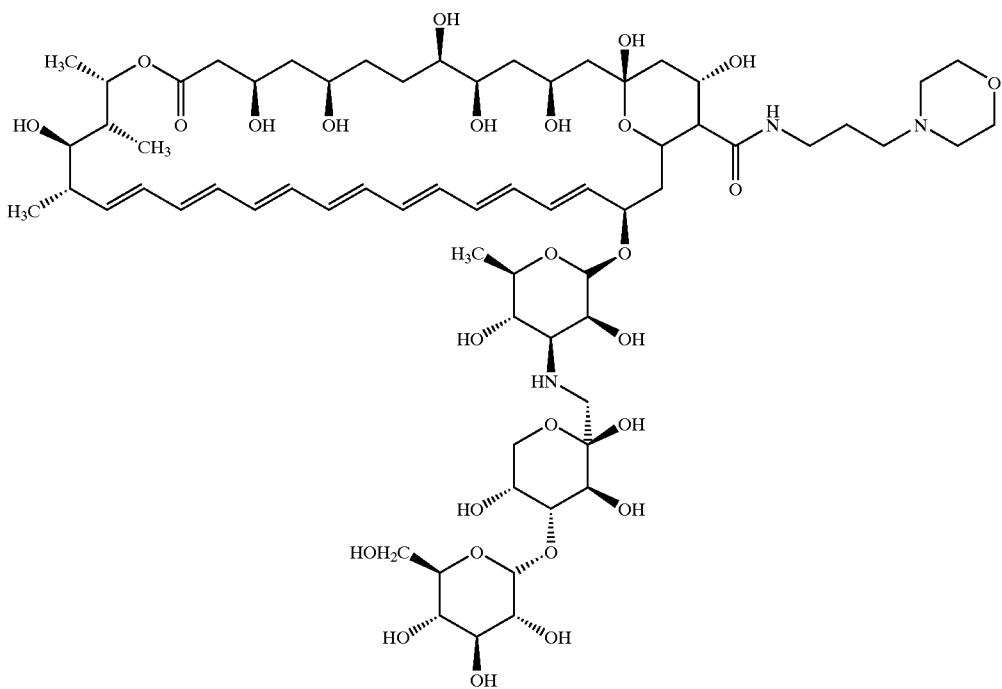
(119)
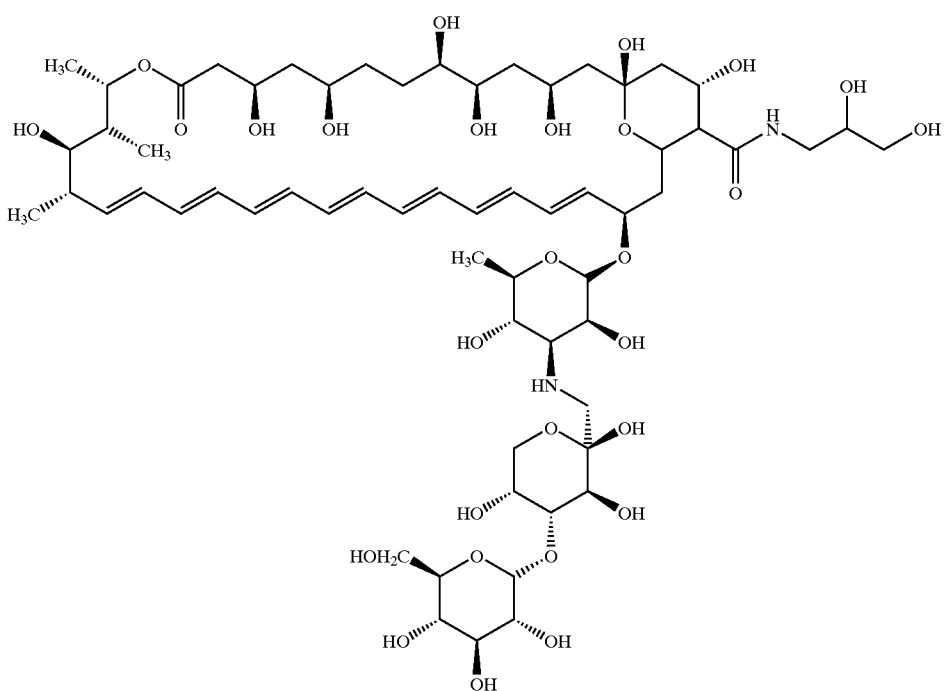

(120)
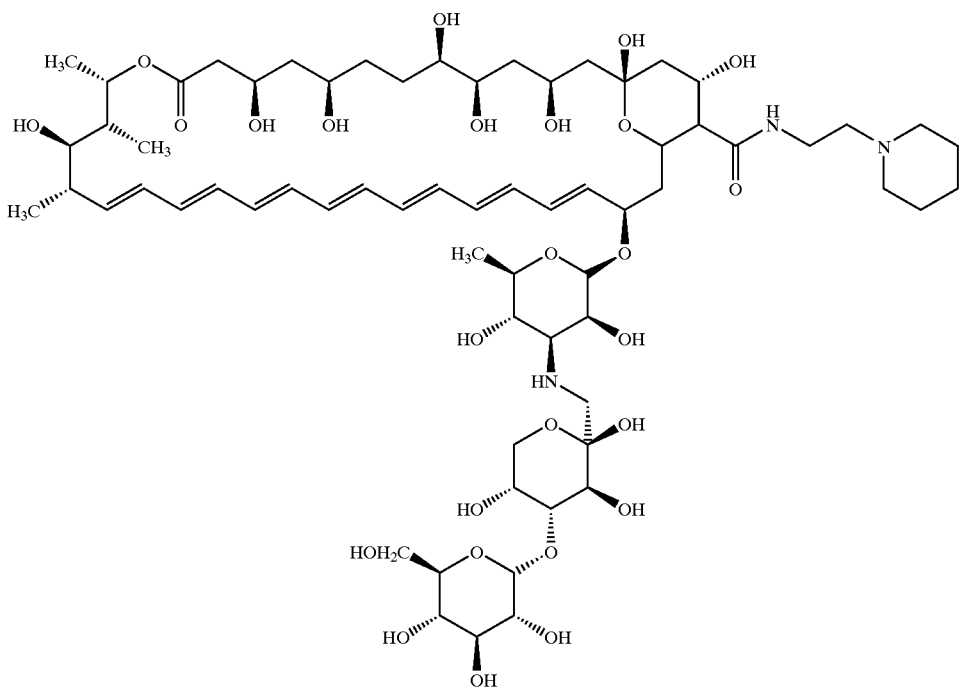
(121)
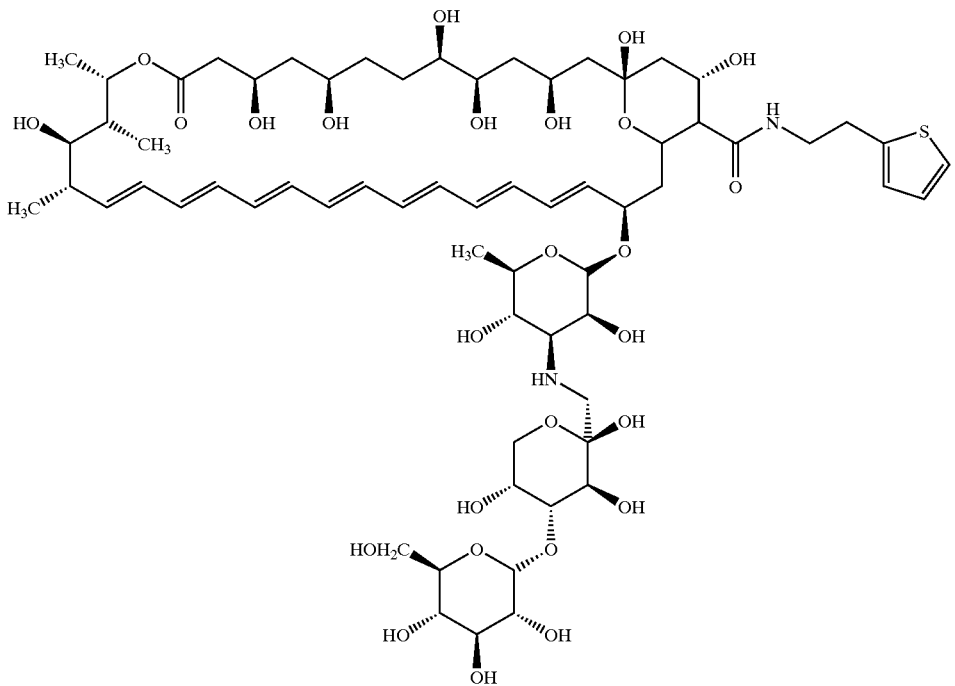

(122)
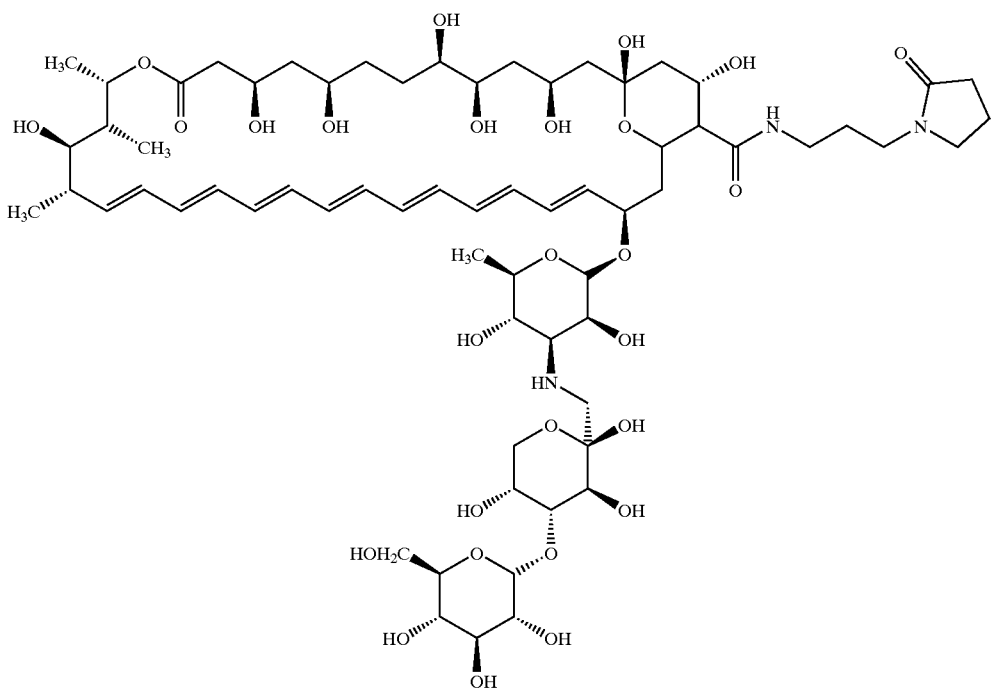
(138)
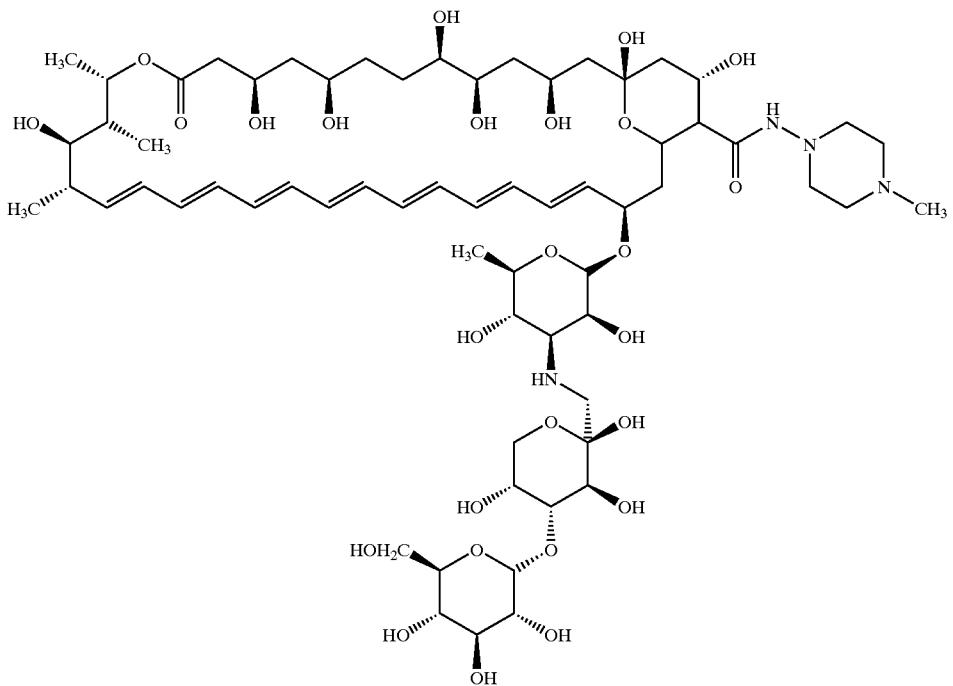

(139)
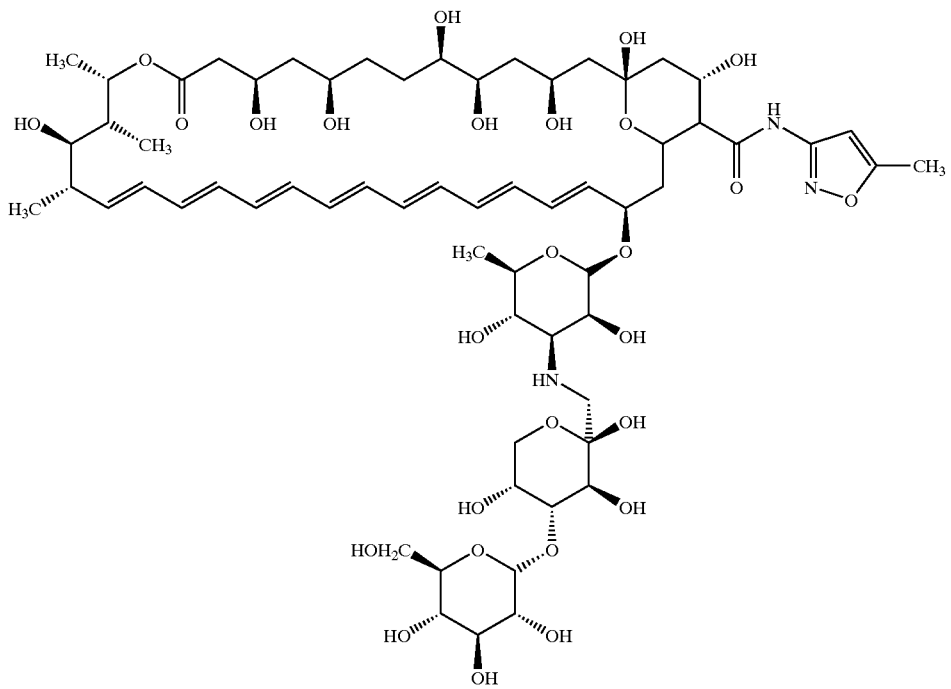
(140)
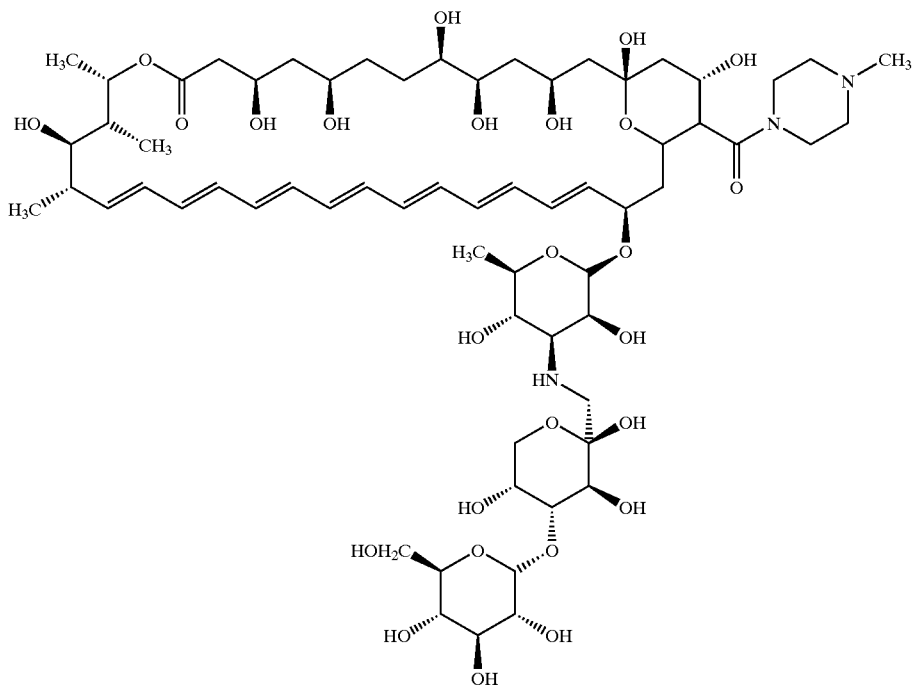
Also exemplified are the corresponding nystatin derivatives of Compounds (116) through (122) and (138) through (140).
Exemplary polyene macrolide amide derivatives according to structural formula (I) in which carbohydrate $CH_2$—$R^2$ is an Amadori rearrangement product using D-cellobiose as the reducing carbohydrate include the following compounds:

(141)
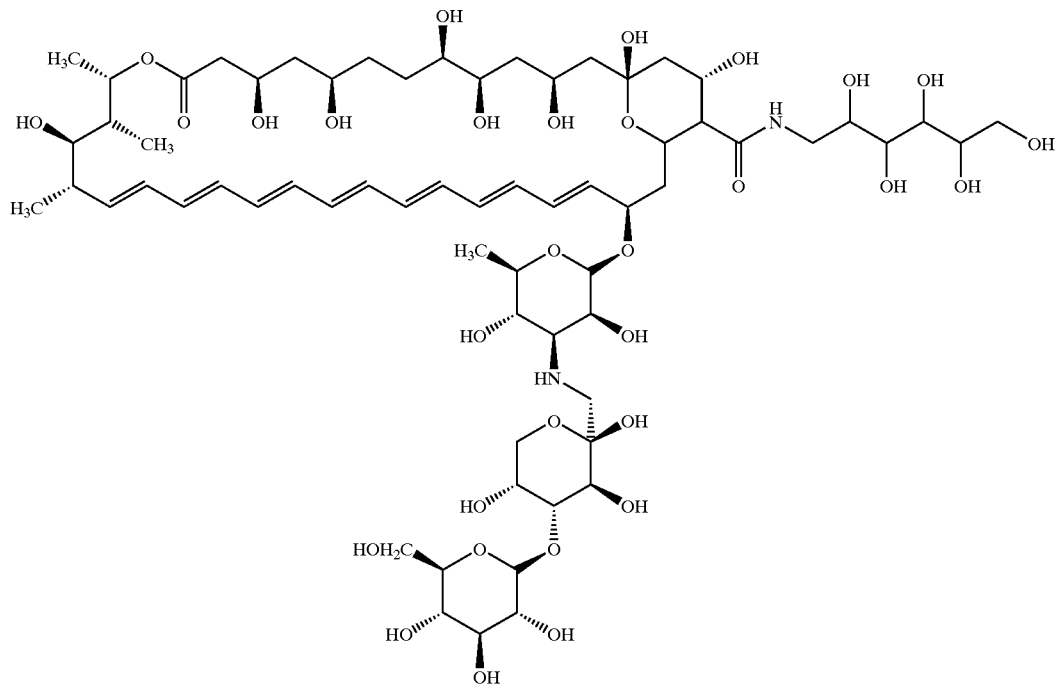
(142)
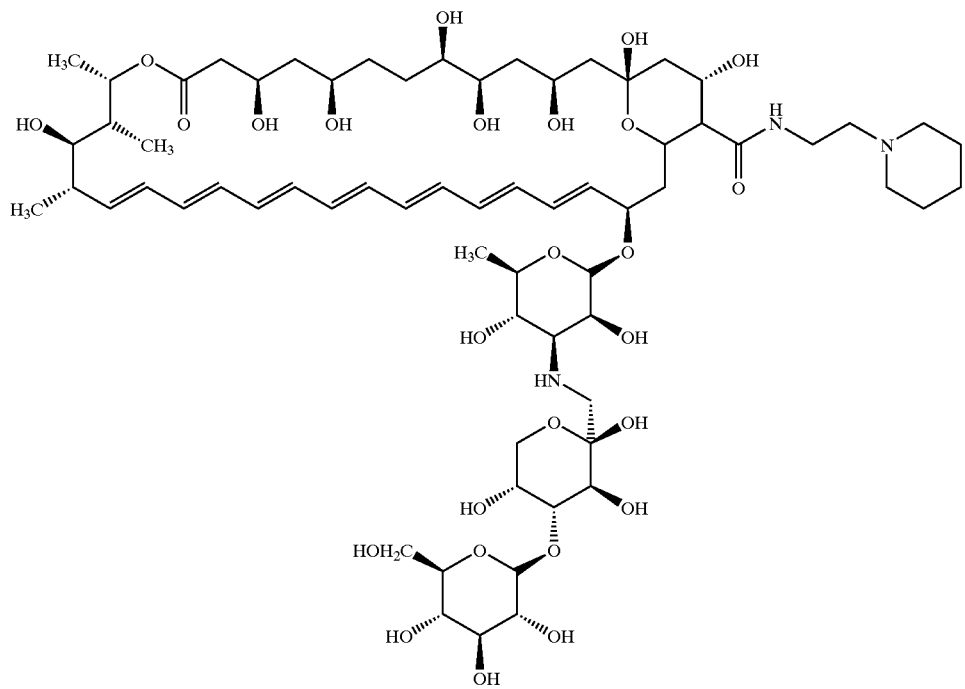

(143)
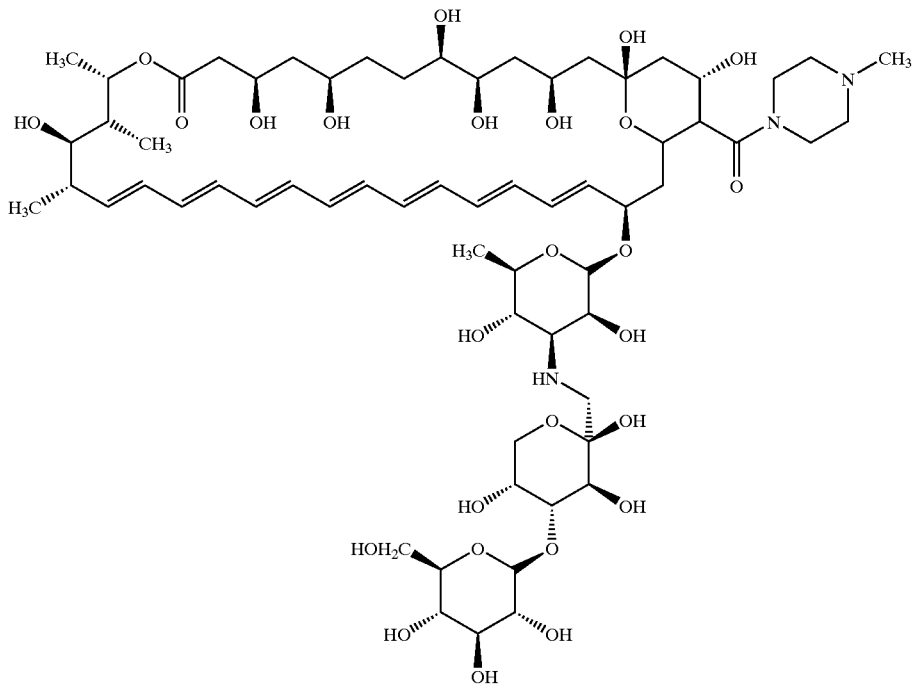
(144)
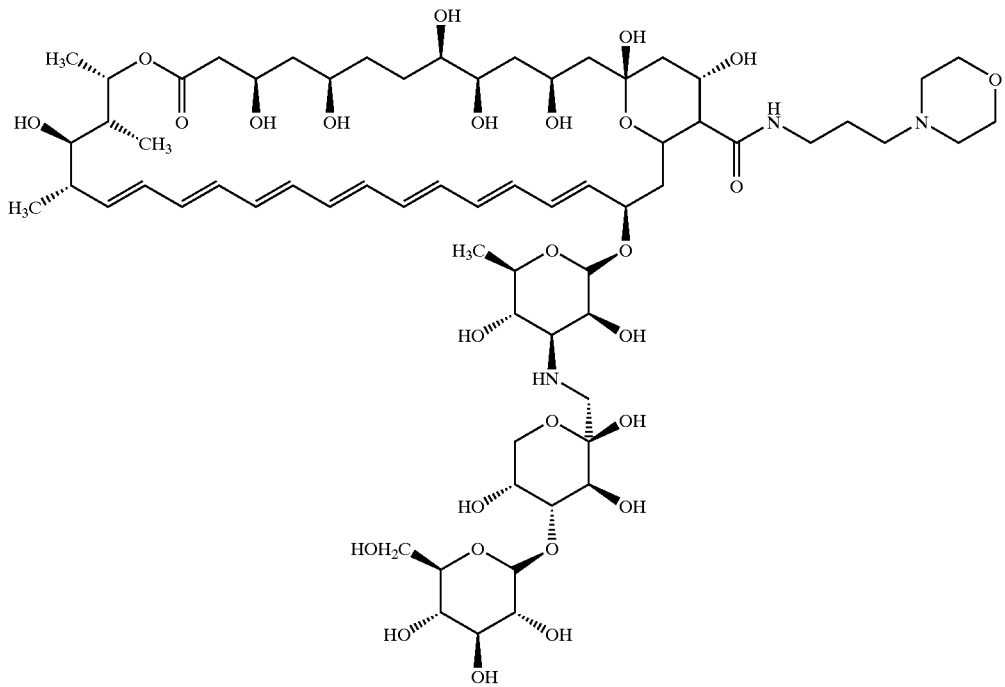
Also exemplified are the corresponding nystatin derivatives of Compounds (141) through (144).
Exemplary polyene macrolide amide derivatives according to structural formula (I) in which carbohydrate $CH_2$—$R^2$ is an Amadori rearrangement product using α-D-lactose as the reducing carbohydrate include the following compounds:

(145)
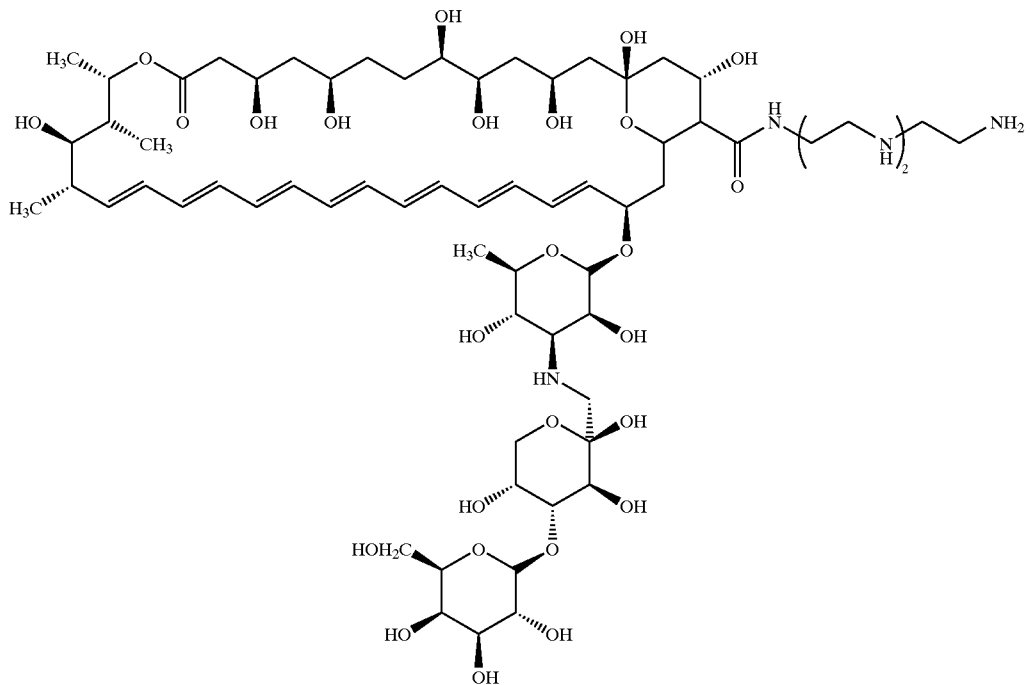
(146)
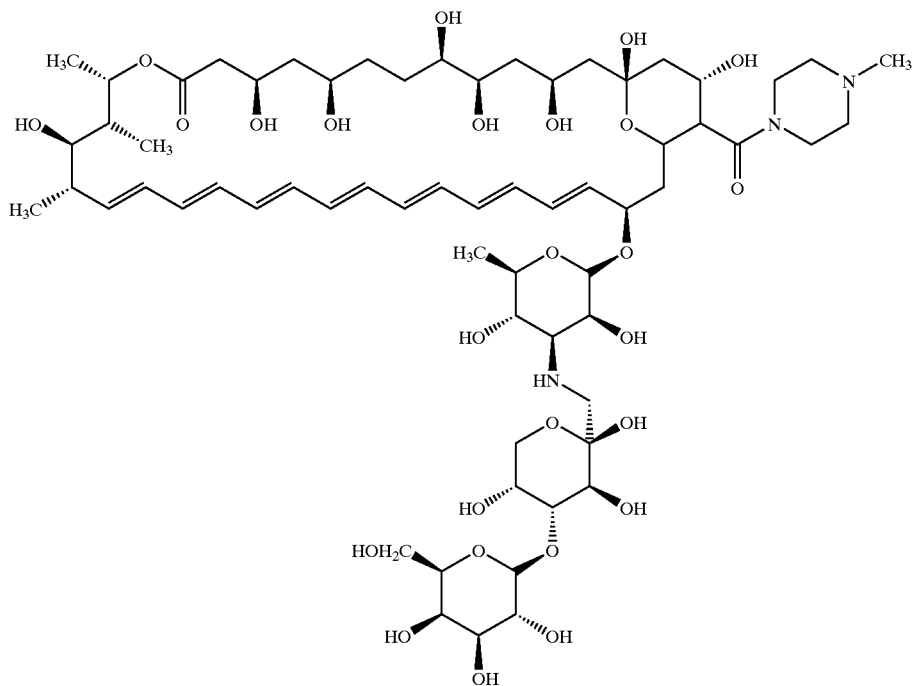

(147)

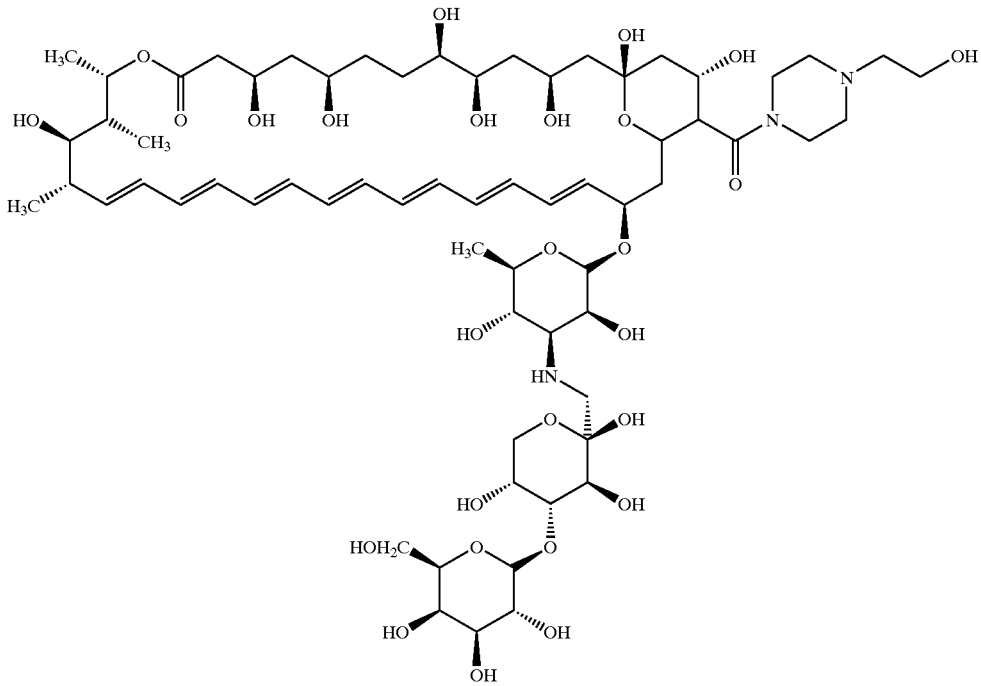

Also exemplified are the corresponding nystatin derivatives of Compounds (144) through (147).

In polyene macrolide amide derivatives according to structural formula (II), $R^4$ and $R^{14}$ are both preferably hydrogen or one is hydrogen and the other is ($C_1$–$C_3$) alkanyl, $R^3$ is hydrogen and/or $R^5$ is a monosaccharide.

Exemplary polyene macrolide amide derivatives according to structural formula (II) include the following compounds:

(123)

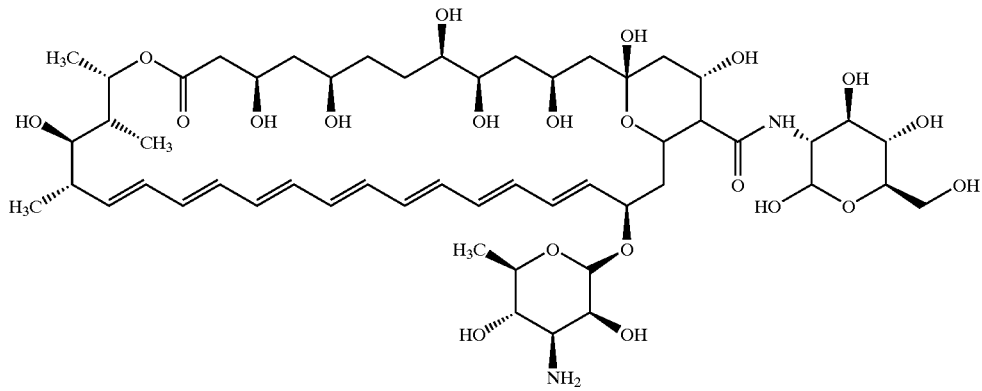

-continued (124)

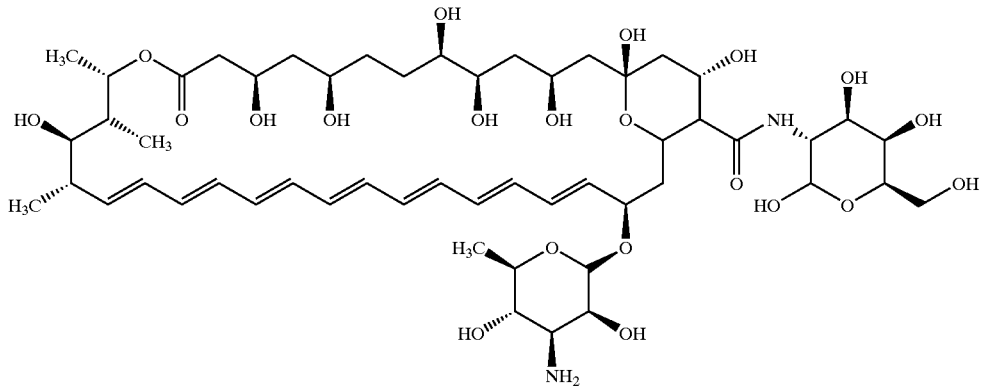

(125)

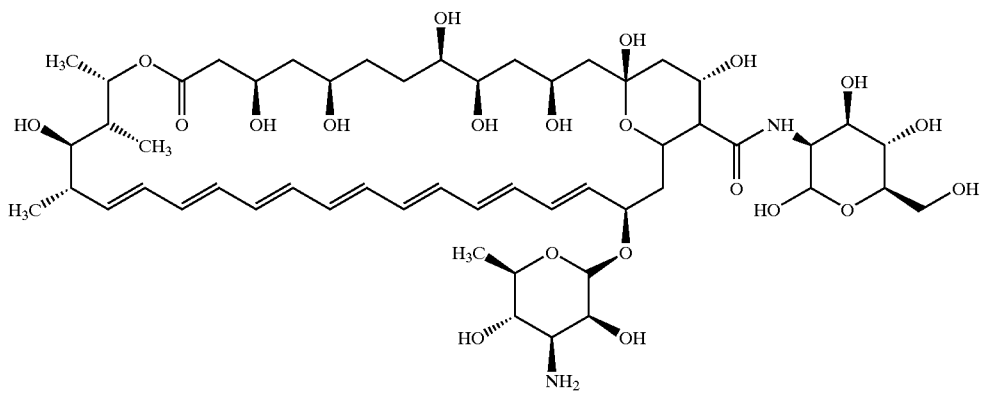

(126)

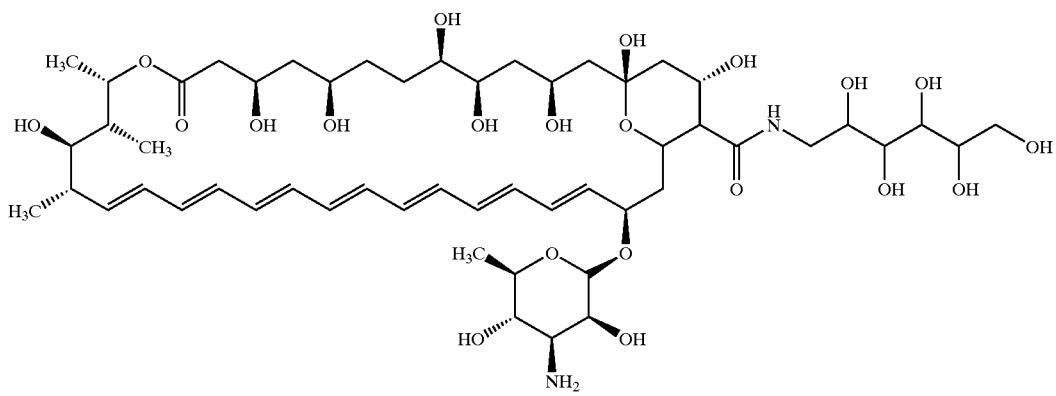

Also exemplified are the corresponding nystatin derivatives of Compounds (123) through (126).

Those of skill in the art will appreciate that many of the compounds encompassed by formulae (I) and (II), as well as the compound species specifically described herein, may exhibit the phenomena of tautomerism, conformational isomerism, geometric isomerism and/or stereo isomerism. As the formula drawings within the specification and claims can represent only one of the possible tautomeric, conformational isomeric, enantiomeric or geometric isomeric forms, it should be understood that the invention encompasses any tautomeric, conformational isomeric, enantiomeric and/or geometric isomeric forms of the compounds having one or more of the utilities described herein, as well as mixtures of these various different forms.

Moreover, in many of the compounds, the polyene backbone N—$R^1$—C(O) is illustrated with the stereochemistry of many of the chiral centers specified. The specific structures depicted are those that have been reported in the literature for the involved polyene backbones, and are not intended as limiting. Thus, it will be understood that the illustrated structures are intended merely as a short-hand way of representing the actual compounds, and to the extent it may be found at a later date that these structural representations are incorrect, they are not intended to be limiting in any way.

The polyene macrolide amide derivatives of formulae (I) and (II) may be synthesized according to well-known methods using well-known chemistries. In one embodiment, the polyene macrolide amide derivatives of formula (I) may be synthesized according to Scheme (I), illustrated below in which $R^6$ and $R^{14}$ are each hydrogen:

Scheme (I)

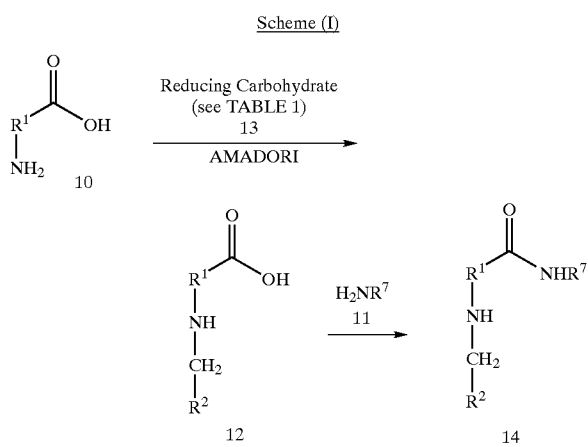

In Scheme (I), N—R¹—C(O), —CH₂—R² and R⁷ are as previously defined for structural formula (I). According to Scheme (I), a parent polyene macrolide 10 having an exocyclic carboxyl group and an amino functionality is reacted with a reducing carbohydrate 13, for example one of the reducing carbohydrates listed in TABLE 1, supra, under Amadori rearrangement conditions to yield glycosylated Amadori product 12. The Amadori rearrangement reaction is described in detail in Amadori, 1955, Adv. Carbohydr. Chem. 10:169 and Hodge & Fisher, supra, both of which are incorporated herein by reference. Amadori product 12 is then converted to the corresponding amide 14 by reaction with amine 11 (preferably in the free base form) using standard methods that are well known in the art (see, e.g., Bruzzese, 1996, Eur. J. Med. Chem. 31:965–992) or the methods described below. Compounds according to structural formula (I) having different water solubility increasing substituents at the amide nitrogen may be synthesized in an analogous manner by reacting Amadori product 12 with an appropriate amine 11. If necessary, any reactive substituents on amine 11 and/or carbohydrate CH₂—R² may be protected using well-known protecting groups and chemistries. The actual protecting group selected will depend upon, among other factors, the identity of the reactive substituent, and will be apparent to those of skill in the art. Non-limiting examples of protecting groups suitable for a wide variety of reactive groups, as well as conditions for their attachment and removal, can be found in Greene & Wats, *Protective Groups in Organic Synthesis*, 3rd Edition, John Wiley & Sons, Inc., NY (1999), which is incorporated by reference.

Alternatively, polyene macrolide amide derivatives of formula (I) may be synthesized according to Scheme (II) below, in which R⁶ and R¹⁴ are each hydrogen:

Scheme (II)

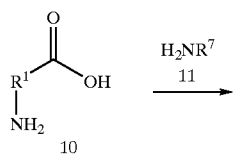

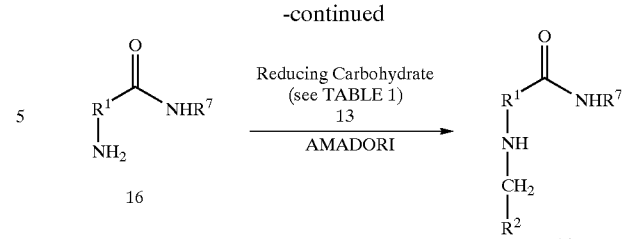

In Scheme (II), N—R¹—C(O), CH—R² and R⁷ areas previously defined for structural formula (I). According to Scheme (II), parent polyene macrolide 10 is reacted with amine 11 (preferably in the free base form) under standard conditions to yield amidated intermediate 16. Amidated intermediate 16 is then reacted with reducing carbohydrate 13 under Amadori rearrangement conditions to yield polyene amide derivative 14. If necessary, any reactive substituents on amine 11 and/or reducing carbohydrate 13 may be protected, as previously described for Scheme (I). Compounds according to structural formula (I) including two water solubility increasing substituents at the amide nitrogen, e.g. compounds of formula (I) in which R⁶ and R⁷ are each other than hydrogen, may be synthesized by routine modification of the illustrated methods by selecting the appropriate amine 11. Compounds according to structural formula (I) in which the amide nitrogen is included in a ring (e.g., compound 106) may be synthesized by routine modification of the illustrated methods by selecting the appropriate amine 11.

It has been discovered that the amidation steps illustrated in Schemes (I) and (II) may be advantageously carried out using chemistries and reagents commonly employed in peptide chemistry for the formation of amide bonds. In one embodiment, the amidation steps may be carried out using an uronium salt, such as, for example, O-(benzotriazol-1-yl)-N,N,N',N'-tetramethyluronium hexafluorophosphate ("HBTU"); O-(7-azabenzotriazol-1-yl)-N,N,N',N'-tetramethyluronium hexafluorophosphate("HATU"); O-(7-azabenzotriazol-1-yl)-N,N,N',N'-bis(tetramethyl ene) uronium hexafluorophosphate ("HAPyU"); O-(benzotriazol-1-yl)-N,N,N',N'-bis(pentamethylene) uronium hexafluorophosphate ("HBPipU"); O-(benzotriazol-1-yl)-N,N,N',N'-bis(tetramethylene) uronium hexafluorophosphate ("HBPyU"); O-(benzotriazol-1-yl)-N,N,N',N'-tetramethyluronium tetrafluoroborate ("TBTU"); O-(benzotriazol-1-yl)-N,N,N',N'-bis(pentamethylene)uronium tetrafluoroborate; O-[4-oxo01,2,3-benzotriazin-3(4H)-yl]-N,N,N',N'-tetramethyluronium tetrafluoroborate ("TDBTU"); O-(1,2-dihydro-2-oxo-1-puridyl)-N,N,N',N'-tetramethyluronium tetrafluoroborate ("TPTU"); O-(N-succinimidyl)-N,N,N',N'-tetramethyluronium tetrafluoroborate ("TSTU"); and O-(5-norborene-2,3-dicarboximido)-N,N,N',N'-tetramethyluronium tetrafluoroborate ("TNTU"). The reactions may be carried out as described, for example, in Dourtuglou, Synthesis, 572 (1984), the disclosure of which is incorporated herein by reference. Briefly, the reactions are typically carried out in the presence of a base, which is most usually an unhindered or hindered amine base such as, for example, diisopropylethyl amine ("DIEA"), N-methylmorpholine or triethylamine, and the desired amine 11 in a polar organic solvent, usually a dipolar organic solvents such as, for example, dimethyl sulfoxide ("DMSO"), dimethylacetamide ("DMA") or dimethylformamide ("DMF"), at a temperature in the range of about −10° C. to 30° C. The ratios of carboxylic acid 10 or 12, uronium salt, base and amine 11 are typically in the range of 1:1:1–3:excess or 1:1.5:1.5–5:1.5, although other ratios may be used.

In another embodiment, the amidation steps may be carried out using a phosphonium salt, such as, for example, benzotriazole-1-yloxy-tris(dimethylamino) phosphonium hexafluorophosphate ("BOP"); bromo-tris-pyrrolidino-phosphonium hexalfluorophosphate ("PyBroP"); and benzotriazole-1-yloxy-tripyrrolodino phosphonium hexafluorophosphate("PyBOP"). The reactions may be carried out as described above for the uronium salts.

It has also been discovered that polyene amide derivatives of formula (I) may be synthesized in a one-pot reaction with high yield. The one-pot reaction is illustrated in Scheme (III) below, in which $R^6$ and $R^{14}$ are each hydrogen:

Scheme (III)

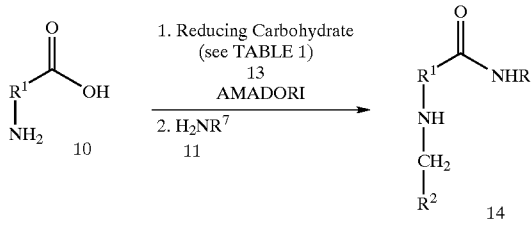

Substituents N—$R^1$—C(O), $CH_2$—$R^2$ and $R^7$ are as defined for structural formula (I). According to Scheme (III), parent polyene macrolide 10 (1 equiv) and reducing carbohydrate 13 (about 1.2 to about 1.5 equiv.) are dissolved in a suitable organic solvent, typically a dipolar solvent such as DMF, and stirred at a temperature in the range of about 30° C. to about 55° C. for about 5 to 72 hr. The reaction may be followed by TLC, HPLC or other routing methods to insure that the first step of the reaction (Amadori rearrangement) has gone to a satisfactory level of completion. The reaction mixture is then cooled, typically to a temperature in the range of about −10° C. to about 5° C. In one embodiment, once cooled, a uronium salt (about 1.5 to about 3 equiv.) or phosphonium salt (about 1.5 to about 3 equiv.) coupling reagent and an appropriate base, for example, DIEA (about _____ to about _____ equiv.) is added, stirred for a few minutes (e.g., from about 5 to about 30 min.), and amine 11 (about 1.5 to about 5 equiv.) is added. In other embodiments, the amidation reagents are added in other orders. For example, the amidation reagents may be added simultaneously, or the amine 11 may be added first followed by the coupling reagent and DIEA, etc. The order of reagent addition for the amidation step is not critical to success. The reaction mixture is then warmed, typically to a temperature in the range of about 20° C. to about 30° C., and the reaction allowed to proceed to completion, which generally takes about 0.5 to about 18 hr. The polyene macrolide amide derivative may be recovered from the reaction mixture using standard techniques, such as precipitation or chromatography.

Polyene macrolide amide derivatives of formula (I) in which substituent $R^{14}$ is an alkyl may be synthesized in a variety of different ways, illustrated in Scheme (IV), infra:

Scheme (IV)

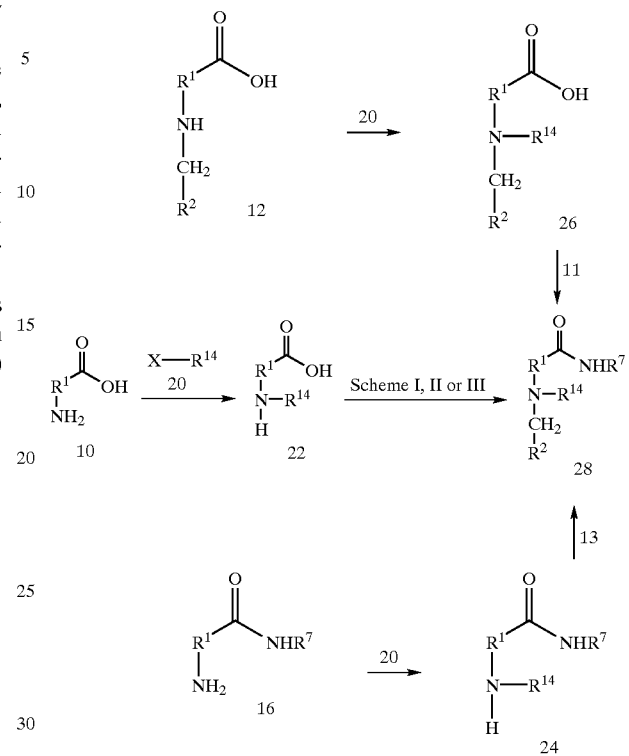

In Scheme IV, substituents N—$R^1$—C(O), $CH_2$—$R^2$, $R^7$ are as defined for structural formula (I), $R^6$ is hydrogen, $R^{14}$ is alkyl and X is a halogen, such as Cl, Br or I. According to Scheme IV, in one method, parent polyene macrolide 10 is first mono-alkylated with alkylating reagent 20 according to standard techniques to yield alkylated parent polyene macrolide 22. Although alkylating reagents 20 is illustrated as a halogenated alkyl, skilled artisans will recognize that virtually any standard alkylating reagents may be used. Alkylated parent macrolide 22 may then be converted to alkylated polyene macrolide amide derivative 28 according to the methods described in Schemes I, I or III.

In another method, glycosylated Amadori product 12 is alkylated using standard alkylation techniques to yield alkylated Amadori product 26, which is then amidated according to any of the previously described methods to yield alkylated polyene macrolide amide derivative 28. In still another method, amidated polyene macrolide 16 is alkylated using standard alkylation techniques to yield alkylated amidated polyene macrolide 24, which is then reacted with carbohydrate 13 under Amadori rearrangement conditions to yield alkylated polyene macrolide amide derivative 28.

Polyene macrolide amide derivatives of formula (II) may be synthesized by routine modification of the above-described methods. Mono- and dialkylated derivatives may be synthesized by first alkylating the parent polyene macrolide 10, followed by amidation, or, alternatively, by first amidating parent polyene macrolide 10, followed by mono- or dialkylation according to standard techniques.

Parent polyene macrolide 10 may be obtained commercially or may be isolated or synthesized according to well-known methods. Methods of synthesizing a variety of parent polyene macrolides 10 are described in Beau, "Polyene Macrolides: Stereostructural Elucidation and Synthetic Studies of a Few Members," In: *Recent Progress in the*

*Chemical Synthesis of Antibiotics*, pp. 135–182, Springer-Verlag, Berlin (1990), as well as the references cited therein. These methods may be routinely adapted to synthesize a wide variety of parent polyene macrolides 10. Methods of isolating parent polyene macrolides 10 as natural products are well-known in the art.

In addition to the above-described methods, methods for converting parent polyene macrolide 10 or glycosylated Amadori product 12 to amides are well-known in the art. Exemplary methods are described in U.S. Pat. No. 4,783,527. Specific methods of synthesizing amides of AmB are described in Czerwinski et al., 1990, J. Antibiot. 43(6):680–683 and Jarzebski et al., 1982, J. Antibiot. 35(2):220–229. Specific methods of synthesizing amides of patricins are described in U.S. Pat. No. 5,298,495, U.S. Pat. No. 5,296,597 and Bruzzese et al., 1996, J. Med. Chem. 31:965–972. Any of these methods may be routinely adapted to synthesize the full range of mono- and di-substituted polyene macrolide amide derivatives of the invention. All of the above-listed patents and references, as well as the various patents and references cited therein, are incorporated herein by reference.

In all of the illustrated schemes, the Amadori rearrangement reaction proceeds in two steps. Referring to Scheme (I), the formation of glycosylated Amadori product 12 proceeds in two steps. In the first step, a glycosylamine (not shown) is formed by condensation of the primary amino group of 10 with the anomeric carbon of reducing carbohydrate 13. In the second step, the glycosylamine is rearranged in an acidic medium to form the glycosylated Amadori product 12. Thus, a reducing carbohydrate 13 reactant should be selected that, after the Amadori rearrangement, will yield the desired carbohydrate residue $CH_2-R^2$.

The principles of the Amadori rearrangement are well-known and have been briefly illustrated supra. Thus, choosing an appropriate reducing carbohydrate 13 will be apparent to those of skill in the art. Specific exemplary reducing carbohydrates 13 are provided in TABLE 1. Additional guidance can be found in Amadori, 1955, Adv. Carbohydr. Chem. 10: 169, Hodge & Fisher, supra, (and the references cited therein) and U.S. Pat. No. 5,314,999, all of which are incorporated herein by reference.

The Amadori rearrangement is acid-catalyzed. Since many of the described rearrangement reactions involve polyene macrolides having an acidic carboxyl substituent, these carboxyl-containing polyene macrolides can "self-catalyze" the rearrangement. Such "self-catalyzed" Amadori rearrangement reactions (e.g., the reactions of Scheme I) may be carried out in virtually any solvent system known in the art to be useful for performing Amadori rearrangement reactions in which the parent polyene macrolide is stable, including the anhydrous solvent systems described in the literature (see, e.g. Hodge & Fischer, supra). For AmB, which is not ver stable in acids and bases, overly acidic and basic solvent systems, such as, for example, glacial acetic acid, should be avoided.

Unlike Scheme (I) and many of the Amadori rearrangements reported in the literature, in the method of Scheme (II), derivatives 16 do not have a free carboxyl group. Rather, the exocyclic carboxyl of parent polyene macrolide 10 has been amidated. Thus, derivatives 16 may not efficiently "self-catalyze" the Amadori rearrangement. As a consequence, it has been discovered that it is preferable to conduct the Amadori rearrangement reaction between amidated derivative 16 and reducing carbohydrate 13 in the presence of water. While the reaction will proceed under anhydrous conditions, significantly better yields are obtained under non-anhydrous conditions. A variety of non-anhydrous solvent systems may be used for Scheme (II). Typically, the solvent system should comprise about 1% (v/v) to 5% (v/v) water. The proton donor may be the solvent system or it may be an added compound, as described in Hodge & Fisher, supra. Any of the solvent systems described in the literature may be adapted for use as described herein. Exemplary solvent systems that may be readily adapted to the principles taught herein are described in Hodge & Fisher, 1963, supra. Specific solvent systems are provided in the Examples section, infra.

When synthesizing polyene macrolide amide derivatives according to Scheme (I), it has been discovered that using N,N'-dimethylpropylene urea ("DMPU") as the solvent for the Amadori rearrangement step yields better results as compared with other solvents, such as DMF. For example, when DMF is used as the solvent, a small but measurable quantity of a side product is produced. By comparison, less of this side product is produced when the reaction is carried out in DMPU.

Moreover, the literature reports that the Amadori rearrangement may be successfully performed with a 1:1 molar ratio of polyene macrolide:reducing carbohydrate, e.g., compounds 10 and 13 in Scheme (I). However, it has been discovered that using a molar ratio in the range of about 1:1.1 yields better results. It has also been discovered that adding the reducing carbohydrate in three equal aliquots at equal intervals of about 1.25 hr to about 1.5 hr, yields better results. Thus, while the Amadori rearrangement reactions illustrated in the above schemes may be performed with 1 equivalent of reducing carbohydrate 13, using about 1.1 total equivalents of reducing carbohydrate 13, added in three equal aliquots of about 0.367 equiv, added at intervals of about 1.25 hr to about 1.5 hr, is preferred.

The polyene macrolide amide derivatives of the invention exhibit significant antifungal activity, typically having minimum inhibitory concentrations (MICs) of about 8 µg/mL or less against *C. albicans* in standard in vitro assays. Generally, active polyene macrolide amide derivatives of the invention are identified using in vitro screening assays that are well-known in the art. Specific in vitro screening assays that can be used to assess activity are provided in the Examples section.

Alternatively, the polyene macrolide amide derivatives of the invention may be assessed for antifungal activity using in vivo models. Again, such models are well-known in the art. Other assays as are well known in the art, or that will become apparent to those having skill in the art upon review of this disclosure, may also be used to identify active polyene macrolide amide derivatives of the invention.

Generally, active polyene macrolide amide derivatives of the invention will exhibit minimum inhibitory concentrations (MICs) of less than about 64 µg/mL, usually less than about 32 µg/mL, preferably less than about 16 µg/mL and most preferably less than about 8 µg/mL against *Candida albicans* using standard methods. Of course, compounds having MICs on the low end of these ranges, or even lower, are preferred.

All of the derivatives of the invention may be used topically or systemically, as will be described in more detail, below. For in vivo applications, such as for systemic administration and/or for use in treating or preventing systemic infections, derivatives that exhibit significant antifungal activity (i.e., less than 4 µg/mL), higher water-solubility than AmB (at approx. neutral pH) and low toxicity are preferred. Generally, derivatives which exhibit an $ED_{50}$ of $\leq 20$ in standard mouse kidney bioburden assays, such as the 5 day and 7 day mouse bioburden assays described in the Examples section, are suitable for in vivo applications. Toxicity is less of a concern for topical administration and applications, as is water solubility.

The polyene macrolide amide derivatives of the present invention have significant advantages over currently available polyene macrolide antifungals. Specifically, the polyene macrolide amide derivatives of the present invention show excellent water solubility, low toxicity, and effective therapeutic potency. Moreover, both classes of derivatives, i.e., compounds according to formulae (I) and (II), exhibit antifungal activity comparable to AmB in both in vitro and in vivo assays, with lower acute toxicity.

The polyene macrolide amide derivatives according to the invention can be used in a wide variety of applications to inhibit the growth of or kill fungi. For example, the polyene macrolide amide derivatives can be used as disinfectants or as preservatives for materials such as foodstuffs, cosmetics, medicaments and other nutrient-containing materials.

For use as a disinfectant or preservative, the polyene macrolide amide derivatives can be added to the desired material singly, as mixtures of several polyene macrolide amide derivatives, or in combination with other antifungal and/or antimicrobial agents. The polyene macrolide amide derivatives may be supplied as the compound per se or may be in admixture with a variety of carriers, diluents or excipients as are well known in the art.

When used to treat or prevent fungal infections the polyene macrolide amide derivatives of the invention can be administered or applied singly, as mixtures of two or more polyene macrolide amide derivatives, in combination with other antifungal, antibiotic or antimicrobial agents or in combination with other pharmaceutically active agents. The polyene macrolide amide derivatives can be administered or applied per se or as pharmaceutical compositions. The specific pharmaceutical formulation will depend upon the desired mode of administration, and will be apparent to those having skill in the art. Numerous compositions for the topical or systemic administration of polyene macrolides are described in the literature. Any of these compositions may be formulated with the polyene macrolide amide derivatives of the invention.

Pharmaceutical compositions comprising the polyene macrolide amide derivatives of the invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the active polyene macrolide amide derivatives into preparations which can be used pharmaceutically. Proper formulation is dependent upon the route of administration chosen.

For topical administration the polyene macrolide amide derivatives of the invention may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration.

For injection, the polyene macrolide amide derivatives of the invention may be formulated in aqueous solutions, preferably in physiologically compatible buffers such as Hanks's solution, Ringer's solution, or physiological saline buffer. The solution may contain formulatory agents such as suspending, stabilizing and/or dispersing agents.

Alternatively, the polyene macrolide amide derivatives may be in powder form for constitution with a suitable vehicle, e.g., sterile pyrogen-free water, before use.

For transmucosal administration, penetrants appropriate to the barrier to be permeated are used in the formulation. Such penetrants are generally known in the art.

For oral administration, the polyene macrolide amide derivatives can be readily formulated by combining them with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate.

If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. Additionally, flavoring agents, preservatives, coloring agents and the like may be added.

For buccal administration, the compositions may take the form of tablets, lozenges, etc. formulated in conventional manner.

For administration by inhalation, the compounds for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may also be formulated in rectal or vaginal compositions such as suppositories or retention enemas, e.g., containing conventional suppository bases such as cocoa butter or other glycerides.

In addition to the formulations described previously, the polyene macrolide amide derivatives may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems may be employed. Liposomes and emulsions are well known examples of delivery vehicles that may be used to deliver the polyene macrolide amide derivatives of the invention. Certain organic solvents such as dimethylsulfoxide also may be employed, although usually at the cost of greater toxicity. Additionally, the polyene macrolide amide derivatives may be delivered using a sustained-release system, such as semipermeable matrices of solid polymers containing the therapeutic agent. Various of sustained-release materials have been established and are well known by those skilled in the art. Sustained-release capsules may, depending on their chemical nature, release the compounds for a few weeks up to over 100 days.

As certain substituents on the polyene macrolide amide derivatives of the invention may be acidic or basic, the derivatives may be included in any of the above-described formulations as the free acids, the free bases or as pharmaceutically acceptable salts. Pharmaceutically acceptable salts are those salts which retain substantially the antifungal activity of the free acids or bases and which are prepared by reaction with bases or acids, respectively. Pharmaceutical salts tend to be more soluble in aqueous and other protic solvents than are the corresponding free base or acid forms. Some examples of pharmaceutically acceptable salts include: (1) acid addition salts, formed with inorganic acids such as hydrochloric acid, hydrobromic acid, sulfuric acid, nitric acid, phosphoric acid, and the like; or formed with organic acids such as amino acids (e.g., aspartic acid, glutamic acid, asparagine, glutamine, lysine, ornithine) acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the amide derivative is either replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. In one embodiment, pharmaceutically acceptable salts are formed with aspartic acid, glutamic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid and mandelic acid. In another embodiment, pharmaceutically acceptable salts are formed with aspartic acid, glutamic acid, and fumaric acid.

The polyene macrolide amide derivatives of the invention, or compositions thereof, will generally be used in an amount effective to achieve the intended purpose. Of course, it is to be understood that the amount used will depend on the particular application.

For example, for use as a disinfectant or preservative, an antifungally effective amount of a polyene macrolide derivative, or composition thereof, is applied or added to the material to be disinfected or preserved. By antifungally effective amount is meant an amount of polyene macrolide derivative or composition that inhibits the growth of, or is lethal to, a target fungi. While the actual amount will depend on a particular target fungi and application, for use as a disinfectant or preservative the polyene macrolide amide derivatives, or compositions thereof, are usually added or applied to the material to be disinfected or preserved in relatively low amounts. Typically, the polyene macrolide derivative comprises less than about 5% by weight of the disinfectant solution or material to be preserved, preferably less than about 1% by weight and more preferably less than about 0.1% by weight. An ordinarily skilled artisan will be able to determine antifungally effective amounts of particular polyene macrolide amide derivatives for particular applications without undue experimentation using, for example, the in vitro assays provided in the examples.

For use to treat or prevent fungal infections, the polyene macrolide amide derivatives of the invention, or compositions thereof, are administered or applied in a therapeutically effective amount. By therapeutically effective amount is meant an amount effective ameliorate the symptoms of, or ameliorate, treat or prevent fungal infections. Determination of a therapeutically effective amount is well within the capabilities of those skilled in the art, especially in light of the detailed disclosure provided herein.

As in the case of disinfectants and preservatives, for topical administration to treat or prevent fungal infections, a therapeutically effective dose can be determined using, for example, the in vitro assays provided in the examples. The treatment may be applied while the infection is visible, or even when it is not visible. An ordinarily skilled artisan will be able to determine therapeutically effective amounts to treat topical infections without undue experimentation.

For systemic administration, a therapeutically effective dose can be estimated initially from in vitro assays. For example, a dose can be formulated in animal models to achieve a circulating polyene macrolide derivative concentration range that includes the MIC as determined in cell culture. Such information can be used to more accurately determine useful doses in humans.

Initial dosages can also be estimated from in vivo data, e.g., animal models, using techniques that are well known in the art. One having ordinary skill in the art can readily optimize administration to humans based on animal data.

Alternatively, initial dosages can be determined from the dosages administered of known polyene macrolides (e.g., AmB) by comparing the MIC of the specific polyene macrolide derivative with that of a known polyene macrolide, and adjusting the initial dosages accordingly. The optimal dosage may be obtained from these initial values by routine optimization.

Dosage amount and interval may be adjusted individually to provide plasma levels of the active polyene macrolide derivative which are sufficient to maintain therapeutic effect. Usual patient dosages for administration by injection range from about 0.1 to 5 mg/kg/day, preferably from about 0.5 to 1 mg/kg/day. Therapeutically effective serum levels may be achieved by administering a single daily dose or multiple doses each day.

As the polyene macrolide amide derivatives of the invention exhibit lower toxicity than AmB they can be administered in a manner similar to AmB. Typical dosages and routes of administration used for AmB are well-known (see, e.g., *Goodman and Gilman's The Pharmacological Basis of Therapeutics*, $8^{th}$ Edition, 1990, Pergamon Press Inc., pp. 1165–1168, incorporated herein by reference).

For example, a small test dose (1 mg compound dissolved in 20 ml of 5% dextrose solution) may be administered intravenously over 20–30 min. The temperature, pulse, respiratory rate and blood pressure of the patient may be recorded every 30 min. for 4 hrs. A patient with a severe, rapidly progressing fungal infection, good cardiopulmonary function and a mild reaction to the test dose can immediately receive 0.3 mg/kg compound intravenously over a period of 2 to 4 hrs (see, e.g., Beunet, 1990 "Antifungal Agents," In: *Principles and Practice of Infectious Diseases,* 3$^{rd}$ Ed., Churchill Livingstone, Inc., New York, pp. 361–370). If the patient has a severe reaction to the test dose or cardiopulmonary impairment, a smaller dose may be recommended, for example, 0.1 mg/kg or 5–10 mg. This dose may be increased by 5–10 mg per day. In severe or fulminant infections, dosage should be escalated rapidly until the patient is receiving 0.5 to 1.0 mg/kg daily.

Incremental doses can be given every 6 to 8 hrs if reactions in a fragile patient make immediate advancement to full dosage inadvisable. For example, a severe reaction to a 1 mg test dose could be followed by 5, 15 and 25 mg given at 8 hr intervals, followed by 40 mg 24 hrs later. The recommended maintenance dose for most deep mycoses is 0.4 to 0.6 mg/kg/day, infused over 2–4 hrs.

In cases of local administration or selective uptake, the effective local concentration of polyene macrolide derivative may not be related to plasma concentration. One having skill in the art will be able to optimize therapeutically effective local dosages without undue experimentation.

The amount of polyene macrolide amide derivative administered will, of course, be dependent on, among other factors, the subject being treated, the subject's weight, the severity of the affliction, the manner of administration and the judgment of the prescribing physician.

The antifungal therapy may be repeated intermittently while infections are detectable, or even when they are not detectable. The therapy may be provided alone or in combination with other drugs, such as for example other antifungals, antibiotics or antimicrobials, or other polyene macrolide amide derivatives of the invention.

Preferably, a therapeutically effective dose of the polyene macrolide amide derivatives described herein will provide therapeutic benefit without causing substantial toxicity. Toxicity of the polyene macrolide amide derivatives can be determined using standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Polyene macrolide amide derivatives which exhibit high therapeutic indices are preferred. The data obtained from these cell culture assays and animal studies can be used in formulating a dosage range that is not toxic for use in human. The dosage of the polyene macrolide amide derivatives described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition. See, e.g., Fingl et al., 1975, In: *The Pharmacological Basis of Therapeutics,* Ch.1, p.1.

The invention having been described, the following examples are presented to illustrate, rather than to limit, the scope of the invention.

5. EXAMPLE

Preparation of Amide Derivatives of Amphotericin B

This example demonstrates the preparation of various amide derivatives of amphotericin B ("AmB"). AmB was purchased from Biosource Pharm, Spring Valley, N.Y. Amines were purchased from Aldrich (Milwaukee, Wis.) or Fluka (Milwaukee, Wis.). All of the compounds synthesized are illustrated in TABLE 2, which is presented at the end of the example. In TABLE 2, the amine reducing carbohydrate used in the amidation and Amadori rearrangement, respectively, are listed. All of the compounds described in TABLE 2, including those that were not specifically synthesized (as demonstrated by the absence of a compound number in the particular table cell) are expected to be active and can be synthesized according to the methods described in this section.

The polyene macrolide amide derivatives are sensitive to light, and should therefore be protected from light during preparation and storage. Storage in amber vials is recommended.

5.1 LCMS and HPLC Analyses

The various reactions described in this example were monitored via LCMS and HPLC as described in this section. Reaction products were characterized using the same conditions.

LCMS was performed on a Finnigan LCQ-Classic mass spectrometer with a Waters Alliance HPLC used as the inlet device or on a Thermoquest LCQ-Duo mass spectrometer with a Thermoquest Surveyor HPLC as the inlet device. The columns used were either a Waters Symmetry C18 (4.6×50 mm) or a Vydac C4 (4.6×50 mm). A flow rate of 0.75 mL/min was used with a linear gradient between Buffer A (0.5% acetic acid in water) and Buffer B (0.5% acetic acid in acetonitrile).

HPLC was performed on an HP 1090 photo diode array HPLC or on an Agilent 1100 photo diode array HPLC. The columns used were the same as for the LCMS analysis. A flow rate of 1.0 mL/min was used with a linear gradient between Buffer A (60 mM Et$_3$N-HOAc pH 6.0) and Buffer B (90% acetonitrile and 10% Buffer A).

5.2 Preparation of Amide AmB Derivatives of Formula (II)

5.2.1 Preparation of Sugar Amine Free Bases

Glucosamine, galactosamine and mannosamine were purchased as hydrochloride salts. For use in the preparation of amides as described in Section 5.2.2 (infra), the free base form of the amines are required. The free base amines were prepared using ion exchange chromatography as described below, illustrated with glucosamine hydrochloride as a specific example. The other sugar amine free bases were prepared by identical methods.

Anion exchange resin (Bio-Rad AG 3-X4, 100–200 mesh) was loaded into a column (25 g) and washed with methanol. Sodium hydroxide solution (1M, 50 mL) was added and the resin was washed with water until the eluant attained pH 7. A solution of glucosamine hydrochloride (5.0 g) dissolved in 50 mL water was added to the resin followed by elution with 300 mL water. The water was lyophilized to give the amino sugar free base.

5.2.2 Preparation of Amides

Compounds 123, 124, 125 and 126 were synthesized as illustrated in Scheme (II), supra. Briefly, AmB (100 mg, 0.11 mmol) was dissolved in 19.65 mL dimethylformamide in a round bottom flask. Triethylamine (100 mL, 1.1 mmol) was added and the solution was stirred at room temperature for 10 min. The appropriate amine in free base form (see Section 5.2.1, supra; see also TABLE 2; 1.1 mmol) was then added, thoroughly mixed, and sonicated for 1 min, followed by the addition of diphenylphosphorylazide (250 mL, 1.1 mmol).

The reaction was allowed to stand at room temperature for 6 hrs. The formation of the glycosylamide AmB product was determined by analytical HPLC (Waters Symmetry C-18, 3.5 mm, 4.6×50 mm) using a linear gradient of 30% to 45% of solvent B over 10 min at a flow rate of 1.1 mL/min, UV=365 nm, and 410 nm (solvent A: 100 mM triethylammonium acetate pH 7/water; solvent B: 90% Acetonitrile/ 100 mM triethylammonium acetate pH 7). The reaction mixture was then diluted by a factor of ten with 100 mM triethylammonium acetate pH 6 and the desired product was purified by preparative reverse-phase HPLC using linear gradient of 25% to 45% of solvent B over 60 min at a flow rate of 6 mL/min, UV=340 nm (solvent A: 100 mM triethylammonium acetate pH 6/water; solvent B: 90% acetonitrile/ 100 mM triethylammonium acetate pH 6). Fractions containing the amide product were pooled and the resultant aqueous solution was lyophilized several times to dry the product and remove excess triethylammonium salts. The structures were confirmed by mass spectra, and the purity was confirmed by HPLC analysis.

The major mass spec peak (MH+) for each compound synthesized is as follows: Compound 123, MH+=1086; Compound 124, MH+=1086; Compound 125, MH+=1086; Compound 126, MH+=1087.

5.3 Two-Pot Synthesis of AmB Amide Derivatives of Formula (I)

Certain amide derivatives according to formula (I) were synthesized according to the "two-pot" method illustrated in Scheme (I), supra. Briefly, AmB was first reacted with a reducing sugar under Amadori rearrangement conditions using the procedure described in Falkowski et al., 1975, "N-Glycosyl Derivatives of Polyene Macrolide Antibiotics," J. Antibiot. 28:244. The resultant glycosylated intermediate was then amidated using standard methods. The specific procedures used for each step of the two-pot synthesis are provided below (the Amadori rearrangement is illustrated with reference to α-D-Glucose). Compounds 100–122, 127–130, 132–136 and 140–144 were synthesized according to this method.

5.3.1 Amadori Rearrangement

AmB (800 mg, 0.86 mmol) was dissolved in 16 mL anhydrous dimethylformamide (DMF) and stirred for 5 min. α-D-Glucose (316 mg, 1.72 mmol) was added. The resulting solution was sealed to the atmosphere and placed in a water bath equilibrated to 37° C. for 6 hr. The reaction was followed by LCMS until judged complete. The reaction product was used directly in the amidation reaction, described infra, without purification. The corresponding D-galactose, D-maltose, D-cellobiose and α-D-galactose glycosylated rearrangement products were obtained using the same procedure, but substituting D-galactose (315 mg, 1.72 mmol), D-maltose hydrate (620 mg, 1.72 mmol), D-cellobiose (588 mg, 1.72 mmol) and α-D-lactose hydrate (620 mg, 1.72 mmol), respectively, for α-D-glucose.

5.3.2 Amidation

To make the corresponding amides, diphenylphosphorylazide (110 μL, 0.92 mmol), triethylamine (128 μL, 0.92 mmol) and the amines from TABLE 2, infra (0.92 mmol), were added to the glycosylated Amadori rearrangement products (crude DMF solution) from Section 5.3.1, supra (2 μL, ca. 100 mg, 0.1 mmol). The solutions were stirred at room temperature and monitored by LCMS. After 4 hr, the products were precipitated with 50 μL of cold diethyl ether. After centrifugation and removal of the ether, the products were dissolved in 40 mL water and lyophilized to give yellow powders. The compound numbers (Cmpds.), amine reactants and reducing carbohydrates used to synthesize the compounds are noted in TABLE 2, infra. The structures of the compounds synthesized are also provided in the Detailed Description of the Invention, supra.

5.4 One-Pot Synthesis of AmB Amide Derivatives of Formula (I)

Certain amide derivatives according to formula (III) were synthesized according to the "one-pot" method illustrated in Scheme (E), supra, using either PyBroP or HBTU as the coupling reagent. Each method is illustrated below with Compound 114. The other compounds synthesized according to each method follow the reaction details.

5.4.1 PyBroP One-Pot Synthesis

To a suspension of AmB (500 mg; 0.514 mmol) in 8 mL of DMF was added D-galactose (107 mg; 0.595 mmol). The reaction mixture was stirred for 72 hr at 50° C. The mixture was cooled to 0° C., DIEA (0.377 mL; 2.164 mmol) and PyBroP (504 mg; 1.082 mmol) were added and the resultant mixture was stirred for 10 min. 1-(2-Amino ethyl)piperidine (0.231 mL; 1.623 mmol) was added, the mixture warmed to 25° C. and stirred for an additional 1.5 hr. The mixture was then suspended in 50 mL ether, filtered through a fritted funned and the collected precipitate was washed with ether (50 mL×2) and acetonitrile (50 mL×3) and dried under house vacuum for 1 hr to yield 640 mg of Compound 114.

Compounds 103, 104, 107, 110, 114, 133 and 135 were synthesized by the same procedure, substituting the appropriate amounts of reducing carbohydrate and amine.

5.4.2 HBTU One-Pot Synthesis

To a suspension of AmB (500 mg; 0.514 mmol) in 8 mL of DMF was added D-galactose (107 mg; 0.595 mmol). The reaction mixture was stirred for 72 hr at 50° C. The mixture was cooled to 0° C., DIEA (0.377 mL; 2.164 mmol) and HBTU (410 mg; 1.082 mmol) were added and the resultant mixture was stirred for 10 min. 1-(2-Amino ethyl)piperidine (0.231 mL; 1.623 mmol) was added, the mixture warmed to 25° C. and stirred for an additional 1.5 hr. The mixture was then suspended in 50 mL ether, filtered through a fritted funned and the collected precipitate was washed with ether (50 mL×2) and acetonitrile (50 mL×3) and dried under house vacuum for 1 hr to yield 660 mg of Compound 114.

5.5 Alternative Amadori Rearrangement Conditions

The compounds of the invention may also be made using the alternative Amadori rearrangement conditions described below. This route utilizes DMPU solvent and a total of 1.1 equiv reducing carbohydrate added to the reaction mixture in three equal aliguots. It can be used in connection with the two-pot synthesis or the one-pot synthesis.

To a solution of AmB (1 equiv) dissolved in 400 mL of N,N'-dimethylpropylene urea ("DMPU") at a temperature in the range of 30° C. to 55° C., typically about 45° C., is added reducing carbohydrate (0.367 equiv). The mixture is stirred for about 1–3 hr, typically about 1.35 hr, and another aliquot of reducing carbohydrate (0.367 equiv) is added. The mixture is again stirred for 1.35 hr and a final aliquot of reducing carbohydrate (0.367 equiv) added. This resulting mixture is then stirred for an additional 18 hr at 45° C., and the resultant Amadori rearrangement product isolated as previously described.

5.6 Preparation of Aspartate Salts

A polyene macrolide derivative is mixed with one equivalent of aspartic acid and then water is added to a concentration of 50 mg/mL. If a clear solution does not result then small amounts of dimethylsulfoxide are added to provide a clear yellow solution, which is frozen and lyophilized to obtain a yellow powder. The yellow powder is dissolved in water, frozen and lyophilized again to obtain the aspartate salt.

5.7 Formulation of Polyene Macrolide Derivatives

The polyene macrolide amide derivatives of the invention, and in particular the aspartic acid salts thereof, posses good water solubility. Most of the compounds of the invention, particularly the aspartate salts, can be dissolved in 5% aq. mannitol (e.g., OSMITROL, Baxter Healthcare, Deerfield, Ill.) to produce yellow, isotonic solutions. Compounds that do not readily dissolve in OSMITROL may be dissolved first in a 0.1% aq. lactic acid solution at pH of about 2.0. For intraperitoneal injections, propylene glycol can be added in small quantities, up to about 10% (v/v), if the polyene macrolide derivative does not dissolve in the lactic acid. A 4.9% aq. mannitol solution (buffered with acetic acid to pH of 5.0) is then added to form a yellow, isotonic solution.

TABLE 2

| | Amine Used in Amidation | None Cmpd. | α-D-Glucose Cmpd. | D-Galactose Cmpd. | D-Maltose Cmpd. | D-Cellobiose Cmpd. | α-D-Lactose Cmpd. |
|---|---|---|---|---|---|---|---|
| A | 1-amino-4-methylpiperazine | | 100 | 108 | 138 | | |
| B | 2-(2-Amino ethyl) pyridine | | 101 | 109 | 116 | | |
| C | 3-amino-5-methylisoxazole | | 102 | 132 | 139 | | |
| D | 1-amino-1-deoxy-D-sorbitol | 126 | 103 | 110 | 117 | 141 | |
| E | 4-(3-aminopropyl) morpholine | | 104 | 111 | 118 | 144 | |
| F | 3-amino-1,2-propanediol | | 105 | 112 | 119 | | |
| G | 1-methylpiperazine | | 106 | 113 | 140 | 143 | 146 |
| H | 1-(2-Amino ethyl) piperidine | | 107 | 114 | 120 | 142 | |
| I | 2-(thiophen-2-yl) ethylamine | | | 115 | 121 | | |

TABLE 2-continued

| | | Sugar Used in Amadori Rearrangement | | | | |
|---|---|---|---|---|---|---|
| Amine Used in Amidation | | None Cmpd. | α-D-Glucose Cmpd. | D-Galactose Cmpd. | D-Maltose Cmpd. | D-Cellobiose Cmpd. | α-D-Lactose Cmpd. |
| J | 1-(3-aminopropyl)-2-pyrrolidinone | | | | 122 | | |
| K | triethylenetetramine | | | | | | 145 |
| L | 1-ethyl-piperazine | | 127 | 133 | | | |
| M | 1-benzyl-piperazine | | 128 | 134 | | | |
| N | 1-(ethan-2-ol)-piperazine | | 129 | 135 | | 147 | |
| O | 1-phenyl piperazine | | 130 | 136 | | | |
| P | morpholine | | 131 | 137 | | | |
| Q | D-glucoseamine·HCl | 123 | | | | | |
| R | D-galactoseamine·HCl | 124 | | | | | |

TABLE 2-continued

| | Sugar Used in Amadori Rearrangement | | | | | |
|---|---|---|---|---|---|---|
| Amine Used in Amidation | None Cmpd. | α-D-Glucose Cmpd. | D-Galactose Cmpd. | D-Maltose Cmpd. | D-Cellobiose Cmpd. | α-D-Lactose Cmpd. |
| 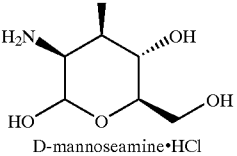 D-mannoseamine•HCl | 125 | | | | | |

6. EXAMPLE

In Vitro Data

For each compound synthesized, Minimum Inhibitory Concentrations (MICs) against *C. albicans* were determined as described in Reference Method for Broth Dilution Antifungal Susceptibility Testing of Yeasts, Approved Standard, NCCLS document M27-A (ISBN 1-56238-328-0), NCCLS, 940 West Valley Road, Suite 1400, Wayne, Pa. 19087, 1997. The MICs (in 1 μg/mL) of the various compounds are provided in TABLE 3, infra). All compounds tested exhibited MICs of 8 μg/nL or less, and many exhibited MIC comparable to AmB (0.125–0.25 μg/mL) and AME (0.75 μg/mL on average).

7. EXAMPLE

In Vivo Data

A variety of the compounds synthesized as described in Section 5, supra, were tested in various in vivo assays, as described below. The results of the various assays are provided in TABLE 3, presented at the end of this section. In all of the in vivo assays described, the test compounds, in the form of the aspartate salts, were formulated in an aqueous vehicle (5% mannitol in sterile water; OSMITROL, Baxter Healthcare, Deerfield, Ill.), followed by appropriate dilutions. The formulations were prepared fresh before dosing.

AmB and AME were also tested for comparison. For AmB, the commercially available FUNGIZONE (Bristol-Meyers Squibb Co.) was used. Reported values are based upon the weight of the AmB active ingredient, not on the basis of the weight of the FUNGIZONE powder. AME was formulated in OSMITROL as described for the test compounds.

7.1 Determination of Maximum Non-Lethal Dose

Maximum non-lethal dose (NLD) data were obtained for selected compounds. A single intravenous dose was administered to each of four mice (Swiss-Webster male mice; Simonsen Laboratories, Gilroy, Calif.) in several groups. The doses selected were based upon the NLDs of compounds of similar structures. After review of findings, higher or lower doses were administered and a NLD was determined. The results are tabulated in TABLE 3, below (NLD Acute Mice). The values for AmB and AME are provided for comparison Each compound evaluated in mice by the intravenous route of administration had a lower order of acute toxicity than AmB.

7.2 Determination of $ED_{50}$: 5 Day Kidney Bioburden Evaluation In Immunocompetent Mice Challenged with *C. Albicans*

Various polyene macrolide amide derivatives of the invention were evaluated for their protective effect when administered intraperitoneally once daily for 5 days to immunocompetent mice challenged with live *C. albicans*.

*C. albicans* was grown on Sabouraud dextrose agar (SDA) plates for 48 hr. Colonies were harvested and washed twice by centrifugation in phosphate-buffered saline (PBS). The washed pellets were resuspended in PBS and diluted to achieve the desired number of fungi per milliliter. A portion of the inoculum was plated on SDA plates to determine the colony-forming units (CFU) per milliliter.

Swiss-Webster mice (Simonsen Laboratories, Gilroy, Calif.) were administered by intravenous injection a single inoculum (0.2 mL) containing as estimated $2.0 \times 10^5$ CFU of *C. albicans*. The day of inoculation was designated as study day 0. Beginning three days after injection, mice were treated intraperitoneally with vehicle alone or formulated test compound once daily for 5 consecutive days.

The mice were observed daily from study day 0 through study day 10 (3 days after the last dose). Mice found dead or euthanized in extremis were removed from the study without further processing. Surviving mice were euthanized by inhalation of $CO_2$ on study day 10 and both kidneys from each mouse were removed. Each pair of removed kidneys was homogenized in 3 mL of ice-cold PBS containing 10% glycerol. A portion of each homogenate was used to determine $\log_{10}$ CFU per kidney using SDA plates (48 hours of incubation at 30° C.). Kidney $\log_{10}$ CFU data were analyzed using a t-test. The criterion for a statistically significant response was set at $p < 0.01$.

The results are tabulated in TABLE 3 ($ED_{50}$ mice 5 day). For comparison, the results for AmB and AME are also provided. Efficacy was defined for individual animals as a greater than 2 $\log_{10}$ reduction in kidney CFU relative to the mean vehicle control value. The $ED_{50}$ for the test compound was determined as the dosage at which 50% of the animals exhibited a 2 $\log_{10}$ reduction in kidney CFU relative to the mean vehicle control value.

When administered intraperitoneally at a dose of 2, 4, 8 or 16 mg/kg/day, AmB was effective in 20%, 60%, 100% and 78% of mice, respectively. The $ED_{50}$ for mice treated with AmB intraperitoneally in this model was calculated to be 3 mg/kg/day. Many of the compounds tested exhibited $ED_{50}$s comparable to AmB in this assay.

7.3 Determination of $ED_{50}$: 7 Day Kidney Bioburden Evaluation In Neutropenic Mice Challenged with C. Albicans Various polyene macrolide amide derivatives of the invention were evaluated for their protective effect when administered intraperitoneally once daily for 7 days to neutropenic mice challenged with live *C. albicans*.

Swiss-Webster mice (Simonsen Laboratories, Gilroy, Calif.) were made neutropenic by intravenous administration of 5-fluorouracil (150 mg/kg) on study day −1. On study day 0, all mice received by intravenous injection a single inoculum (0.2 mL) containing as estimated $5.0 \times 10^4$ CFU of *C. albicans*. The day of inoculation was designated as study day 0. Beginning the day after infection (on study day 1), mice were treated intraperitoneally with vehicle alone or formulated test compound, once daily for 7 consecutive days.

The mice were observed daily from study day 1 through study day 8 (1 day after the last dose). Mice found dead or euthanized in extremis were removed from the study without further processing. Surviving mice were euthanized by inhalation of $CO_2$ on study day 8 and both kidneys from each mouse were removed. Each pair of removed kidneys was homogenized in 3 mL of ice-cold PBS containing 10% glycerol. A portion of each homogenate was used to determine $\log_{10}$ CFU per kidney using SDA plates (48 hours of incubation at 30° C.). Kidney $\log_{10}$ CFU data were analyzed using a t-test. The criterion for a statistically significant response was set at p<0.01.

The results are tabulated in TABLE 3 ($ED_{50}$ mice 7 day). For comparison, the results for AmB and AME are also provided. Efficacy was defined for individual animals as a greater than 2 $\log_{10}$ reduction in kidney CFU relative to the mean vehicle control value. The $ED_{50}$ for the test compound was determined as the dosage at which 50% of the animals exhibited a 2 $\log_{10}$ reduction in kidney CFU relative to the mean vehicle control value.

7.4 Two Week Range-Finding Toxicity Study in Mice

Various polyene macrolide amide derivatives of the invention were evaluated to characterize their potential toxicity when administered subchronically by intravenous injection.

CD-1® mice (Charles River Laboratories, Portage, Mich.) were acclimated to laboratory conditions for at least 5 days before the start of dosing. During the acclimation period, the general condition of the mice was evaluated, and those considered healthy were used. The mice were randomly assigned to treatment groups using a stratified body weight regimen. Each treatment group consisted of 3 male and 3 female mice. The mice were housed in a room with a controlled environment and provided rodent chow and water ad libitum.

On the first day of dosing, the mice were approximately 7 to 9 weeks old and weighed 22 to 30 g. Doses were administered by intravenous injection once daily on study days 1 to 5 and 8 to 12. Dosages were selected based upon data from efficacy and toxicology studies, and ranged from 1.25 to 30 mg/kg/day. Clinical observations were recorded 0.5 hr after dosing on days 1, 3, 5, 8, 10, 12 and 15, and on any day a change was observed. Body weights were recorded prior to dosing and on study days 8 and 12, and on study day 15 at the completion of the in-life phase of the study.

Animals that were found in a moribund/deteriorating clinical state were euthanized (animal designated killed in extremis) by inhalation of $CO_2$. The day of death for any animal found dead or killed in extremis was recorded. Any animal that died prematurely was removed from the study without further processing.

One day after completion of dosing (study day 16), all surviving mice were euthanized by inhalation of $CO_2$. Their kidneys were preserved for histopathologic examination. The maximum no-observed-adverse-effect level (NOAEL) was determined on the basis of clinical and histopathologic findings. Results are tabulated in TABLE 3. The values for AmB and AME are provided for comparison.

7.5 Ascending Single-Dose Nephrotoxicity Study in Rabbits

Various polyene macrolide amide derivatives of the invention were evaluated to determine the intravenous dose of administered compound that produces nephrotoxicity in rabbits. Nephrotoxicity was monitored by measuring urine volume and blood urine nitrogen (BUN) and creatinine.

Female New Zealand white rabbits (Hra: (NZW) SPF; Covance, Richmond, Calif.) were acclimated to laboratory conditions for 9 days before the start of dosing. During the acclimation period, the rabbits were acclimated to restrainers on four separate days. The duration of restraint on the first day of acclimation did not exceed 5 min. The duration of restraint on the last day of acclimation was 50 min. During the study, the animals were restrained for no more than 60 min per day.

The rabbits were housed in a room with a controlled environment and placed on a restricted diet of 125 g rabbit chow per day. Water was provided ad libitum.

Ascending single doses were administered by intravenous infusion into an ear vein at a rate of 0.6 mL/min. Each ascending dose was followed by a non-dosing observation period of at least two days. The clinical condition of each rabbit was observed daily for general condition and availability of food and water. Body weights were recorded before each dose, as well as 2 days after the last dose. Blood samples were collected from the rabbits two days prior to the first dose (study day −2) and approximately 24 hr after each dose and analyzed for BUN and creatinine. Urine was collected for two 24-hour periods prior to the initiation of dosing and for the 24-hour period following each treatment. Necropsy was not performed.

Body weight, urine output, BUN and creatinine data were evaluated statistically using a one-tailed Mann-Whitney test. The criterion for statistical significance was set at p≦0.05. The maximum no-observed-adverse-effect level (NOAEL) of nephrotoxicity was determined on the basis of the above measurements. Results are tabulated in TABLE 3. The values for AmB and AME are provided for comparison.

7.6 Determination of $ED_{50}$ in a Mouse Survival Model

Swiss-Webster mice (Simonsen Laboratories, Gilroy, Calif.) are made neutropenic by intravenous administration of 5-fluorouracil (150 mg/kg) on study day −1. On study day 0, all mice receive by intravenous injection a single inoculum (0.5 mL) containing as estimated $5.0 \times 10^4$ CFU of *C. albicans*. The day of inoculation is designated as study day 0. At approximately 4 hr post-injection, mice are treated intraperitoneally with test compound once daily for 7 consecutive days.

The mice are observed daily from study day 0 through study day 28. Mice found dead or euthanized due to moribund condition are removed from the study. Surviving mice are euthanized by inhalation of $CO_2$ on study day 28 and removed from the study. Moribund mice are recorded as dead the day after euthanasia.

The $ED_{50}$ for the test compound was determined as the dosage at which 50% of the animals survived.

7.7 Kidney Bioburden Evaluation in Immunosupressed Mice Challenged with *Candida Glabrata*

*C. glabrata* is grown in 20 mL SBA broth (250 mL Ehrlenmeyer) for 24 hr at 37° C. in a stationary incubator. The suspension is washed twice by centrifugation in PBS. The washed pellets are resuspended in PBS and diluted to achieve the desired number of fungi per milliliter. A portion of the inoculum is plated on SDA plates to determine the colony-forming units (CFU) per milliliter.

Black female C57 mice were are immunosupressed by administration intraperitoneally of cyclophosphamide (100 mg/kg) on study days −3, 0, 3, 6 and 9. On study day 0, all mice receive by intravenous injection a single inoculum (0.2 mL) containing as estimated $1.5 \times 10^8$ CFU of *C. glabrata*. Beginning 4 days after inoculation, mice are treated intraperitoneally with either vehicle control or test compound formulation once daily for 5 consecutive days.

The mice are observed daily through study day 11 (3 days after the last dose). Mice found dead or euthanized in extremis are removed from the study without further processing. Surviving mice are euthanized by inhalation of $CO_2$ on study day 11 and both kidneys from each mouse are removed. Each pair of removed kidneys is homogenized in 3 mL of ice-cold PBS containing 10% glycerol. A portion of each homogenate was used to determine $\log_{10}$ CFU per kidney using SDA plates (48 hours of incubation at 37° C.). Kidney $\log_{10}$ CFU data are analyzed using a t-test. The criterion for a statistically significant response was set at $p<0.01$.

Efficacy is defined for individual animals as a greater than 2 $\log_{10}$ reduction in kidney CFU relative to the mean vehicle control value. The $ED_{50}$ for test compounds is determined as the dosage at which 50% of the animals exhibit a 2 $\log_{10}$ reduction in kidney CFU relative to the mean vehicle control value.

TABLE 3

| Compound No. | MIC (μg/mL) | NLD (mg/kg) acute mice | $ED_{50}$ (mg/kg) mice 5 day | $ED_{50}$ (mg/kg) mice 7 day | NOAEL (mg/kg) 2 week mice histological | NOAEL (mg/kg) 2 week mice clinical | NOAEL (mg/kg) acute rabbit |
|---|---|---|---|---|---|---|---|
| AMB | 0.125–0.25 | 1.5 | 3 | 0.3 | 0.85 | 0.5 | 0.375 |
| AME | 0.75 | 60 | 13.1 | 8.3 | >32 | >32 | 7.5 |
| 123 | 5.3 | 32 | | | | | |
| 124 | 1.0 | 16 | | | | | |
| 125 | 1.0 | 8 | | | | | |
| 100 | 2.0 | | | | | | |
| 101 | 4.0 | | | | | | |
| 102 | 2.7 | | | | | | |
| 103 | 1.1 | 10 | 15 | | | | |
| 104 | 2.0 | 20 | 9 | 3.1 | <10 | 10 | 7.5 |
| 105 | 2.0 | | | | | | |
| 106 | 2.0 | <15 | 3 | | 6 | 3 | |
| 107 | 2.0 | >40 | 28 | | | | |
| 110 | 1.0 | 10 | 15 | | | | |
| 108 | 4.0 | | | | | | |
| 113 | 3.3 | 7.5 | 2 | | 1.25 | >5 | |
| 109 | 2.0 | | | | | | |
| 111 | 2.7 | 20 | 7 | | 7 | <7 | |
| 132 | | | | | | | |
| 112 | | | | | | | |
| 114 | 4.0 | 40 | 9 | 6.1 | 9 | 9 | 7.5 |
| 115 | | | | | | | |
| 116 | 8.0 | | | | | | |
| 139 | | | | | | | |
| 117 | 8.0 | | | | | | |
| 118 | 5.3 | | | | | | |
| 119 | 8.0 | | | | | | |
| 120 | 8.0 | | | | | | |
| 121 | 8.0 | | | | | | |
| 122 | 8.0 | | | | | | |
| 140 | | | | | | | |
| 141 | | | | | | | |
| 142 | | | | | | | |
| 143 | | | | | | | |
| 144 | | | | | | | |
| 138 | | | | | | | |
| 127 | | | | | | | |
| 128 | | | | | | | |
| 129 | | | | | | | |
| 130 | | | | | | | |
| 133 | | 15 | 4.1 | | NA | <5 | |
| 134 | 1.0 | 30 | >30 | | | | |
| 135 | 6.3 | 10 | 1.6 | | >5 | 1.25 | |
| 136 | 0.4 | >15 | 40.2 | | | | |
| 146 | 2.0 | <7.5 | | | | | |
| 147 | 2.0 | <7.5 | | | | | |
| 131 | 4.0 | 5 | | | | | |
| 137 | 2.0 | 5 | | | | | |

TABLE 3-continued

| Compound No. | MIC (µg/mL) | NLD (mg/kg) acute mice | $ED_{50}$ (mg/kg) mice 5 day | $ED_{50}$ (mg/kg) mice 7 day | NOAEL (mg/kg) 2 week mice histological | NOAEL (mg/kg) 2 week mice clinical | NOAEL (mg/kg) acute rabbit |
|---|---|---|---|---|---|---|---|
| 145 | 1.0 | 20 | | 3 | | | |
| 123 | 5.3 | 32 | | | | | |
| 124 | 1.0 | 16 | | | | | |
| 125 | 1.0 | 8 | | | | | |
| 126 | 3.0 | | | | | | |

Having been described, the present invention is not to be limited in scope by the exemplified embodiments, which are intended as illustrations of single aspects of the invention, and any compositions and methods which are functionally equivalent are within the scope of the invention. Indeed, various modifications of the invention in addition to those described above will become apparent to those skilled in the art from the foregoing description and accompanying drawings. Such modifications are intended to fall within the scope of the appended claims.

We claim:

1. A compound according to structural formula (I):

(I)

including pharmaceutically acceptable salts thereof, wherein:

N—$R^1$—C(O) is a polyene macrolide backbone;

$CH_2$—$R^2$ is a carbohydrate residue, wherein the illustrated $CH_2$ is derived from the anomeric carbon of a terminal carbohydrate saccharide and $R^2$ represents the remainder of the carbohydrate;

either (i) $R^6$ is selected from the group consisting of hydrogen, —$(CH_2)_n$—$NR^{15}R^{16}$, —$NR^{15}R^{16}$, —$(CH_2)_n$—$R^{17}$, polyhydroxylated alkyl, ($C_1$-$C_6$) alkyl substituted with one or more of the same or different $R^{10}$ group and ($C_1$-$C_6$) heteroalkyl substituted with one or more of the same or different polar substituent, and $R^7$ is selected from the group consisting of —$(CH_2)_n$—$NR^{15}R^{16}$, —$NR^{15}R^{16}$, —$(CH_2)_n$—$R^{17}$, polyhydroxylated alkyl, ($C_1$-$C_6$) alkyl substituted with one or more of the same or different $R^{10}$ group, and ($C_1$-$C_6$) heteroalkyl substituted with one or more of the same or different polar substituent; or (ii) $R^6$ and $R^7$, taken together with the nitrogen atom to which they are bonded, form 5- or 6-membered saturated or unsaturated ring which optionally includes one or more of the same or different additional heteroatoms selected from the group consisting of O, N, NH, and S and which is optionally substituted at one or more ring carbon or heteroatoms with the same or different substituents selected from the group consisting of a polar substituent, ($C_1$-$C_6$) alkyl, ($C_1$-$C_6$) alkoxy, —$(CH_2)_n$—(polar substituent), ($C_5$-$C_6$) aryl, phenyl, 6- to 9-membered arylalkyl and benzyl;

each $R^{10}$ is independently selected from the group consisting of =O (oxo), =NH (imino), —C(=NH)—$NH_2$ (amidino), and —NH—C(=NH)—$NH_2$ (guanidino);

$R^{14}$ is hydrogen or alkyl;

$R^{15}$ and $R^{16}$ taken together with the nitrogen atom to which they are bonded, form a 5- or 6-membered saturated or unsaturated ring which optionally includes one or more of the same or different additional heteroatoms selected from the group consisting of O, N, NH, and S and which is optionally substituted at one or more ring carbon or heteroatoms with the same or different substituents selected from the group consisting of a polar substituent, ($C_1$-$C_6$) alkyl, ($C_1$-$C_6$) alkoxy, —$(CH_2)_n$—(polar substituent), ($C_5$-$C_6$) aryl, phenyl, 6- to 9-membered arylalkyl and benzyl;

$R^{17}$ is a 5- or 6-membered saturated or unsaturated ring including one or more of the same or different heteroatoms selected from the group consisting of O, N, NH and S and which is optionally substituted at one or more ring carbon or heteroatoms with the same or different substituents selected from the group consisting of polar substituent, ($C_1$-$C_6$) alkyl, ($C_1$-$C_6$) alkoxy, —$(CH_2)_n$—(polar substituent), ($C_5$-$C_6$) aryl, phenyl, 6- to 9-membered arylalkyl and benzyl;

each polar substituent is independently selected from the group consisting of —OH, —SH, =O, =S, —$NH_2$, =NH, —$N_3$, —CN, —C(=NH)—$NH_2$, and —NH—C(=NH)—$NH_2$; and each n is independently an integer from 1 to 6.

2. The compound of claim 1 in which polyene macrolide backbone N—$R^1$—C(O) is derived from amphotericin B or nystatin.

3. The compound of claim 1 in which $R^{14}$ is hydrogen.

4. The compound of claim 1 wherein $R^6$ and $R^7$ are defined according to alternative (i).

5. The compound of claim 1 wherein $R^6$ and $R^7$ are defined according to alternative (ii).

6. The compound of claim 1 which has one or more features selected from the group consisting of:

N—$R^1$—C(O) is a polyene backbone derived from AmB or nystatin;

$CH_2$—$R^2$ is a mono-, di- or oligosaccharide;

$R^6$ is hydrogen; and $R^{14}$ is hydrogen.

7. The compound of claim 1 wherein:

$R^6$ is hydrogen;

$R^7$ is selected from the group consisting of —$(CH_2)_n$—$NR^{15}R^{16}$, —$(CH_2)_n$—$R^{17}$ and polyhydroxylated alkyl; and $R^{15}$, $R^{16}$, and $R^{17}$ are as defined in claim 1.

8. The compound of claim 1 wherein:
either: (i) $R^6$ and $R^7$, taken together with the nitrogen atom to which they are bonded, form a 5- to 6-membered cycloheteroalkyl ring which is optionally substituted with one or more substituent selected from the group consisting of ($C_1$–$C_6$) alkyl, ($C_1$–$C_6$) alkoxy, —$(CH_2)_n$—(polar substituent), ($C_5$–$C_6$) aryl, phenyl, 6- to 9-membered arylalkyl and benzyl, wherein the heteroatoms are O or N; or (ii) $R^6$ and $R^7$, taken together with the nitrogen atom to which they are bonded, form a 5- to 6-membered cycloheteroalkyl ring which is substituted with one or more substituent selected from the group consisting of ($C_1$–$C_6$) alkyl, ($C_1$–$C_6$) alkoxy, —$(CH_2)_n$(polar substituent), ($C_5$–$C_6$) aryl, phenyl, 6- to 9-membered arylalkyl and benzyl; and each polar substituent is independently an amino or hydroxy.

9. The compound of claim 1 in which —$CH_2$—$R^2$ is a mono-, di- or oligosaccharide.

10. The compound of claim 9 in which —$CH_2$—$R^2$ is an Amadori rearrangement product of a reducing carbohydrate selected from the group consisting of glucose, galactose, maltose, cellobiose and lactose.

11. The compound of claim 1 or 10 in which substituent $NR^6R^7$ is contributed by any of the amines selected from the group consisting of 1-amino-4-methylpiperazine, 2-(2-aminoethyl) pyridine, 3-amino-5-methylisoxazole, 1-amino-1-1 deoxy-D-sorbitol, 4-(3-aminopropyl) morpholine, 3-amino-1,2-propanediol, 1-methylpiperazine, 1-(2-aminoethyl) piperidine, 2-(thiophen-2-yl) ethylamine, 1-(3-aminopropyl)-2-pyrrolidinone, triethylenetetramine, 1-ethyl-piperazine, 1-benzyl-piperazine, 1-(ethan-2-ol)-piperazine, 1-phenyl piperazine, morpholine, D-glucoseamine (HCl) D-galactoseamine(HCl), and D-mannoseamine(HCl).

12. A compound according to structural formula (II):

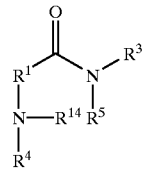

(II)

including the pharmaceutically acceptable salts thereof wherein:
N—$R^1$—C(O) is a polyene macrolide backbone;
$R^{14}$ is hydrogen, or alkyl;
$R^3$ is hydrogen, a non-polar substituent or a water-solubility increasing substituent;
$R^4$ is hydrogen or alkyl; and
$R^5$ is a water-solubility increasing substituent selected from the group consisting of polyhydroxylated alkyl, monosaccharide, disaccharide and oligosaccharide.

13. The compound of claim 12 in which polyene macrolide backbone N—$R^1$—C(O) is derived from amphotericin B or nystatin.

14. The compound of claim 12 in which $R^4$ is hydrogen.

15. The compound of claim 12 in which R3 is a water-solubility increasing substituent selected from the group consisting of polyhydroxylated alkyl, monosaccharide, disaccharide and oligosaccharide.

16. The compound of claim 12 in which $R^3$ is hydrogen or lower alkyl.

17. The compound of claim 12 in which $R^5$ is selected from the group consisting of glucosyl, galactosyl and mannosyl.

18. The compound of claim 12 which is selected from the group consisting of:

(123)

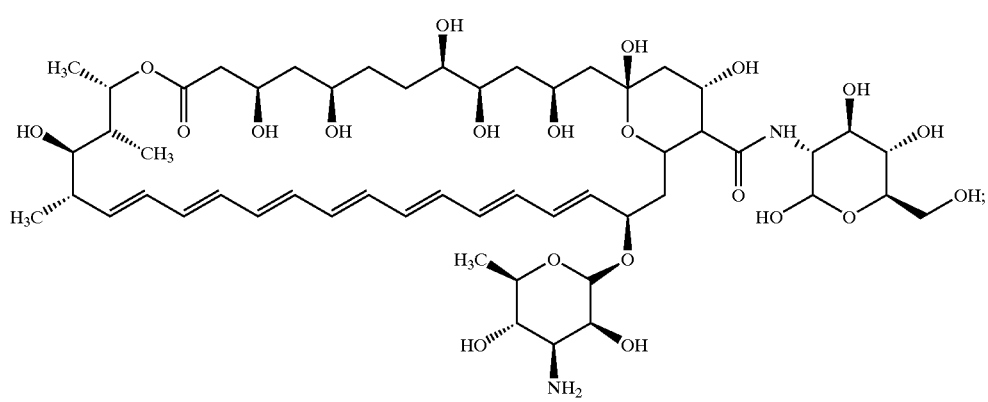

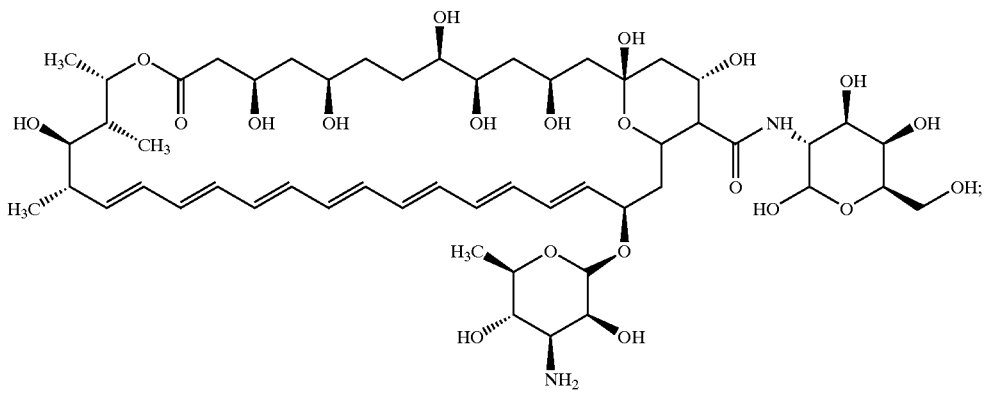

(124)

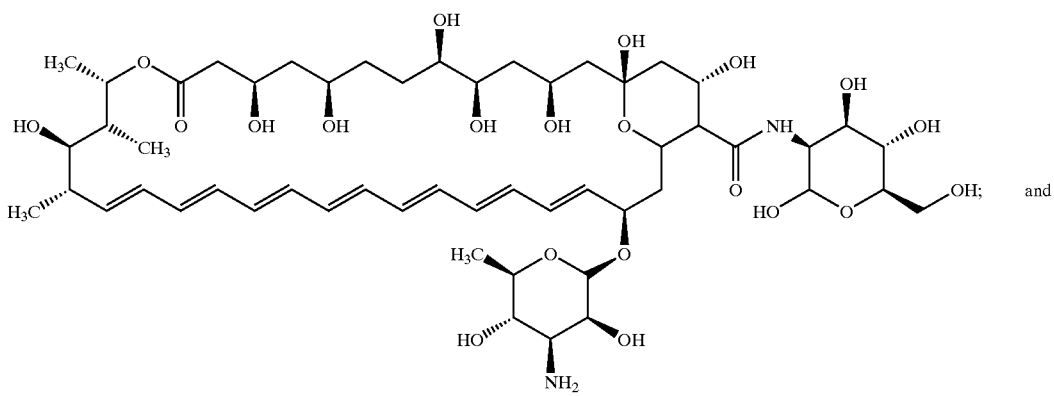

(125) and

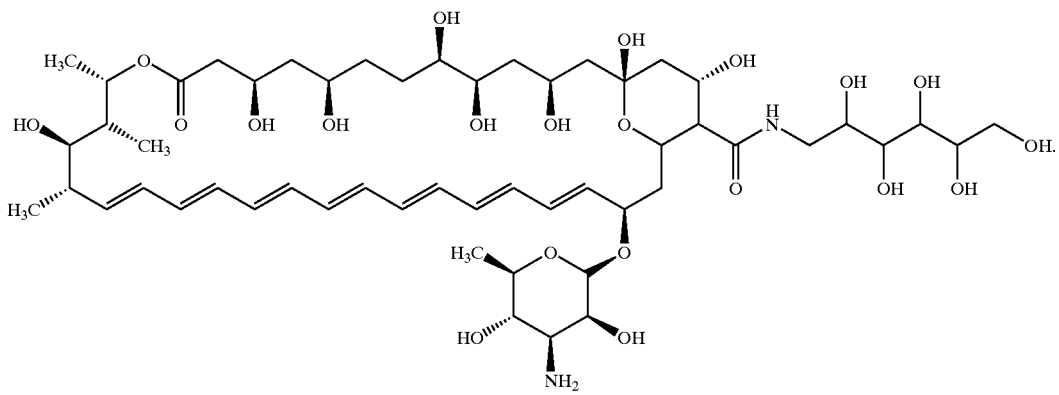

(126)

19. A pharmaceutical composition comprising a compound according to claim 1 or claim 12 and a pharmaceutically-acceptable carrier, excipient or diluent.

20. A method of inhibiting the growth of a fungus comprising contacting the fungus with an amount of a compound according to claim 1 or claim 12 effective to inhibit the growth of the fungus.

21. A method of treating or preventing a fungal infection in a subject comprising administering to a subject an amount of a compound according to claim 1 or claim 12 effective to treat or prevent the fungal infection.

22. The method of claim 21 in which the subject is a human, an animal or a plant.

23. The method of claim 21 in which the infection is a topical infection.

24. The method of claim 21 in which the infection is a systemic infection.

25. A method of making a polyene macrolide amide derivative, comprising the steps of:

reacting a parent polyene macrolide with a reducing carbohydrate under Amadori rearrangement conditions to yield an Amadori rearrangement product; and amidating the Amadori rearrangement product with an amine reagent of the formula $HNR^6R^7$, where $R^6$ and $R^7$ are as defined in claim 1, to yield the polyene amide macrolide derivative.

26. The method of claim 25, further comprising the step of N-alkylating the parent polyene macrolide, the Amadori rearrangement product or the resultant polyene macrolide amide derivative.

27. A method of making a polyene macrolide amide derivative, comprising the steps of:
  amidating a parent polyene macrolide with an amine reagent of the formula $HNR^6R^7$, where $R^6$ and $R^7$ are as defined in claim 1, to yield an amidated polyene macrolide; and
  reacting the amidated polyene macrolide with a reducing carbohydrate under Amadori rearrangement conditions to yield the polyene macrolide amide derivative.

28. The method of claim 27, further comprising the step of N-alkylating the parent polyene macrolide, the amidated polyene macrolide or the resultant polyene macrolide amide derivative.

29. The method according to any one of claims 25 or 26 wherein the amidation step is effected with an uranium salt or phosphonium salt coupling reagent.

30. The method of claim 25 which is carried out in a single pot.

31. A method of making a polyene macrolide amide derivative according to structural formula (I):

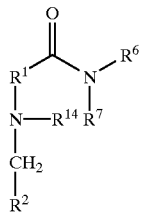

(I)

wherein $N$—$R^1$—$C(O)$, $CH_2$—$R^2$, $R^6$, $R^7$ and $R^{14}$ are as defined in claim 1, comprising the steps of:
  reacting a polyene macrolide according to structure (III):

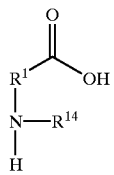

(III)

with a reducing carbohydrate under Amadori rearrangement conditions to yield an Amadori rearrangement product; and
  amidating the Amadori rearrangement product with an amine reagent of the formula $HNR^6R^7$ to yield the polyene macrolide amide derivative of formula (I).

32. A method of making a polyene macrolide amide derivative as defined in claim 12, comprising the steps of:
  amidating a parent polyene macrolide with an amine reagent of the formula $HNR^3R^5$, wherein $R^3$ and $R^5$ are as defined, in claim 12, to yield the polyene macrolide amide derivative.

33. The method of claim 31 which further includes the step of N-mono or dialkylating the parent polyene macrolide or the resultant polyene macrolide amide derivative.

34. The method of claim 31 in which the amidation step is effective with an uronium salt or phosphonium salt coupling reagent.

35. A method of making a polyene macrolide amide derivative according to structural formula (II):

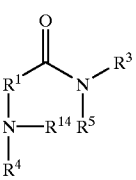

(II)

wherein $N$—$R^1$—$C(O)$, $R^3$, $R^4$, $R^5$ and $R^{14}$ are as defined in claim 14, comprising the steps of:
  reacting a polyene macrolide according to structure (IV):

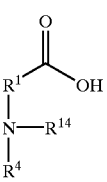

(IV)

with an amine reagent of the formula $HNR^3R^5$, where $R^3$ and $R^5$ are as defined in claim 14, to yield the polyene macrolide amide derivative according to structural formula (II).

36. The method of claim 35 wherein the amidation step is effective with an uronium salt or phosphonium salt coupling reagent.

37. The polyene, macrolide amide derivative produced by the method of any one of claims 25, 27, 31, or 35.

38. The compound of claim 1 selected from the group consisting of

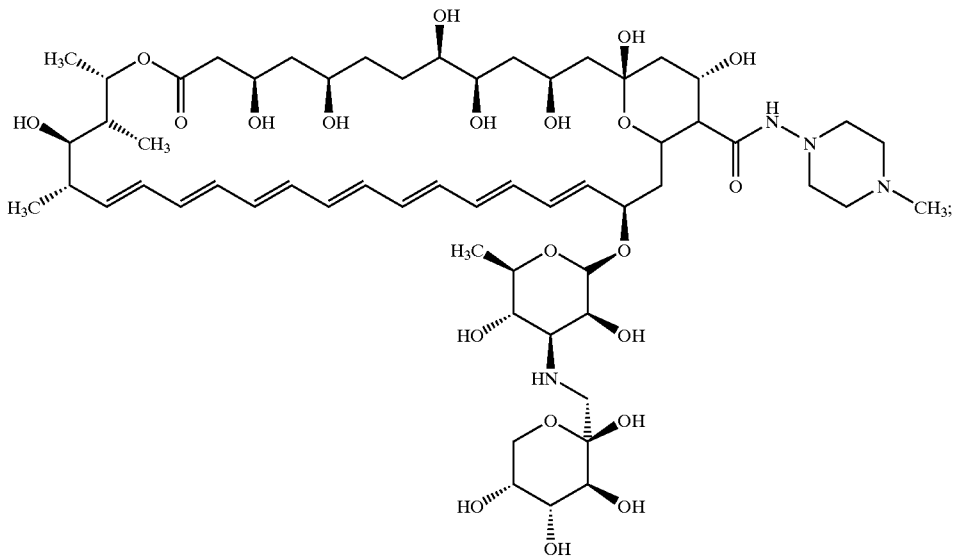
(100)
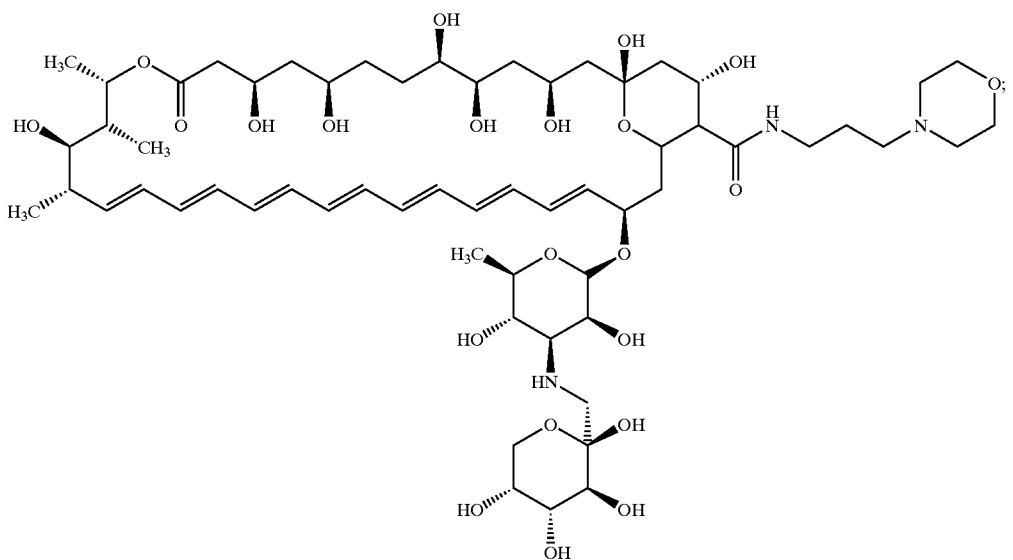
(104)
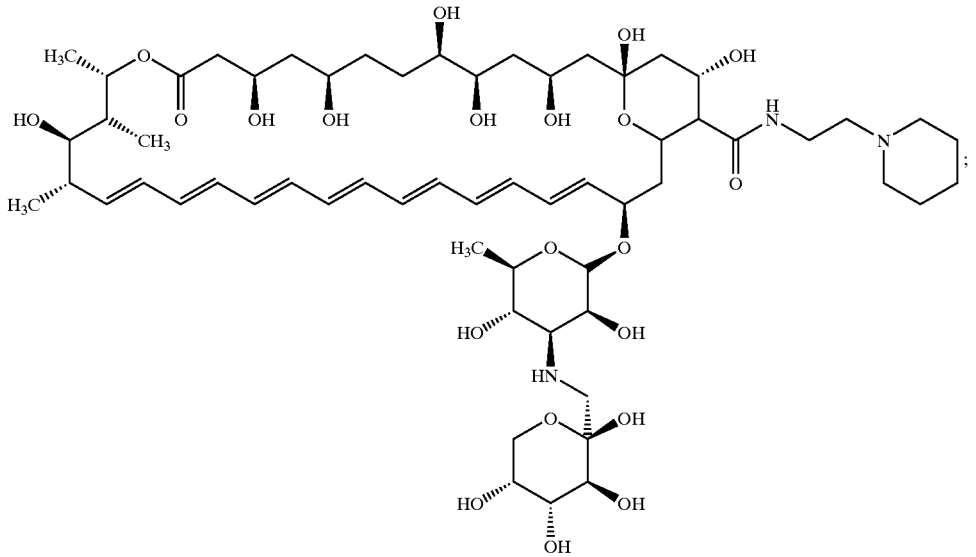
(107)

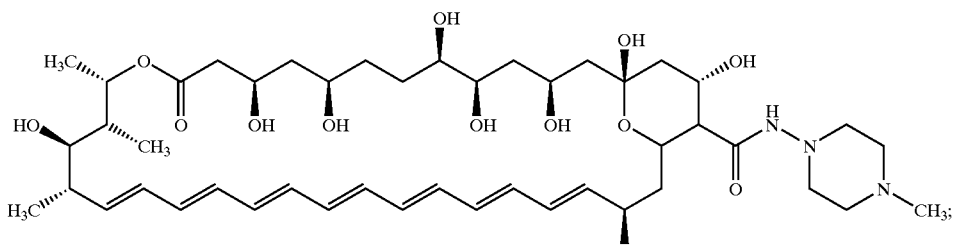
(108)
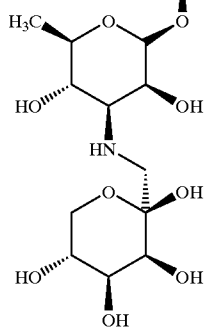
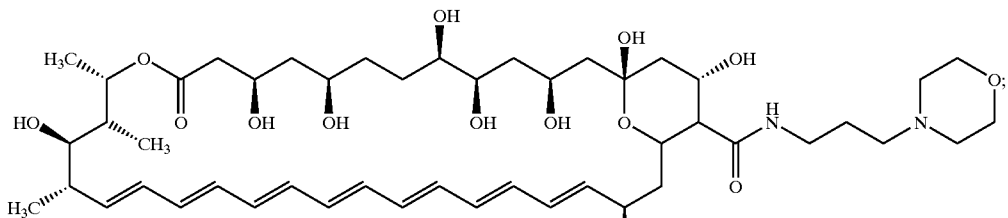
(111)
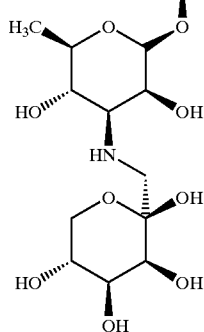
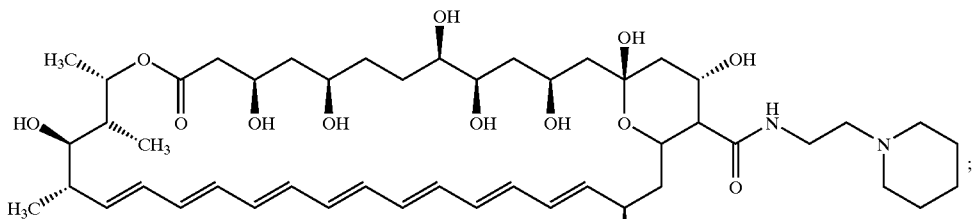
(114)
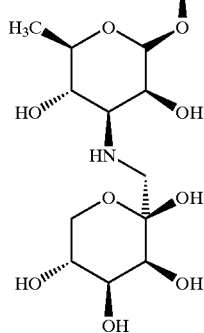

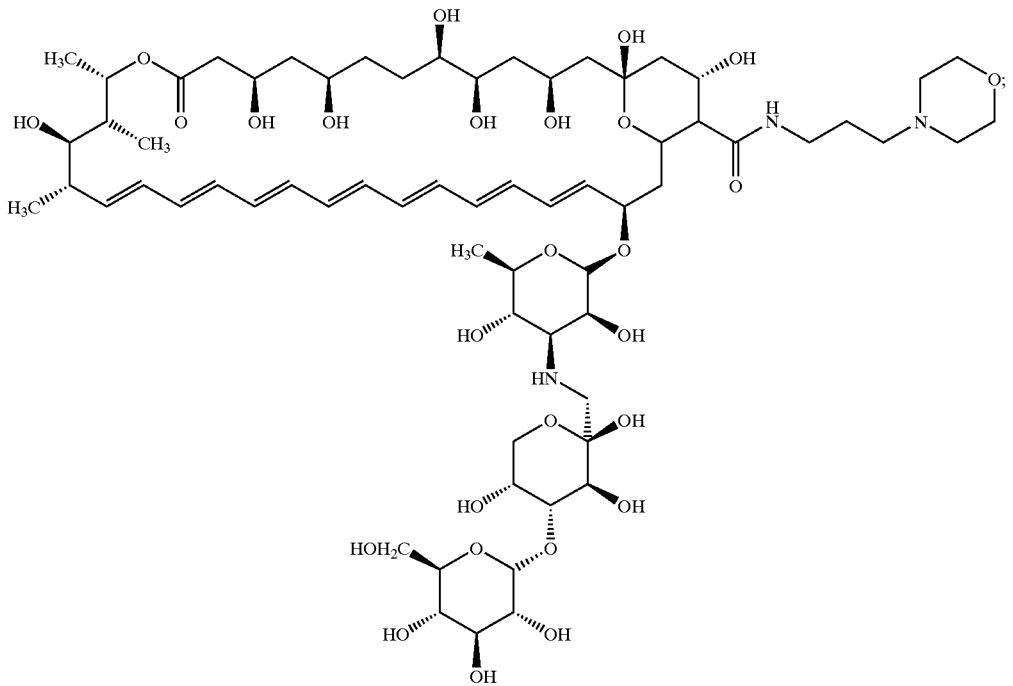
(118)
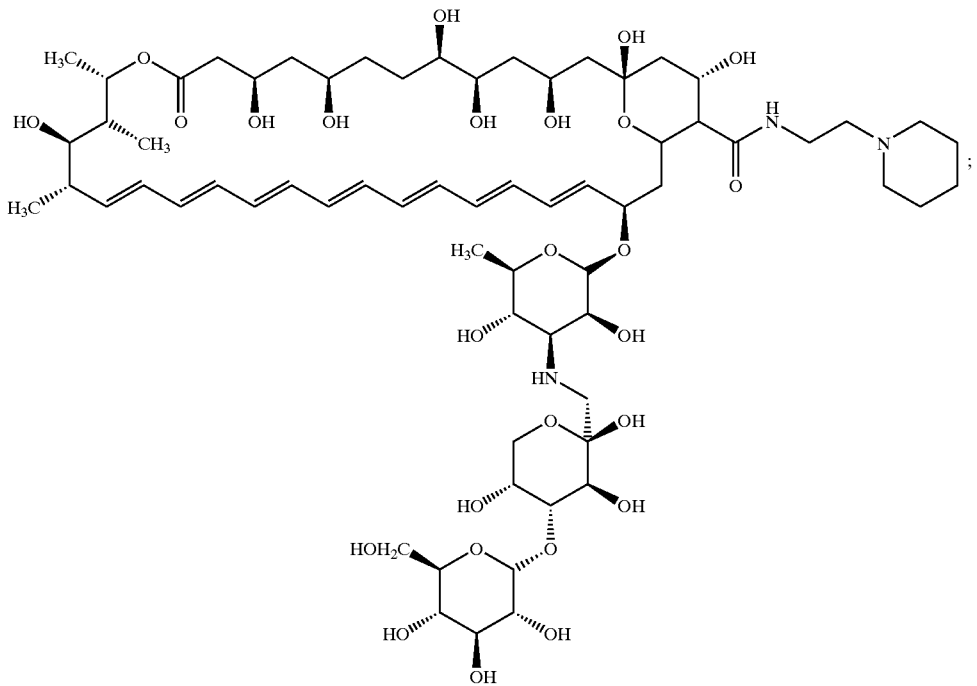
(120)

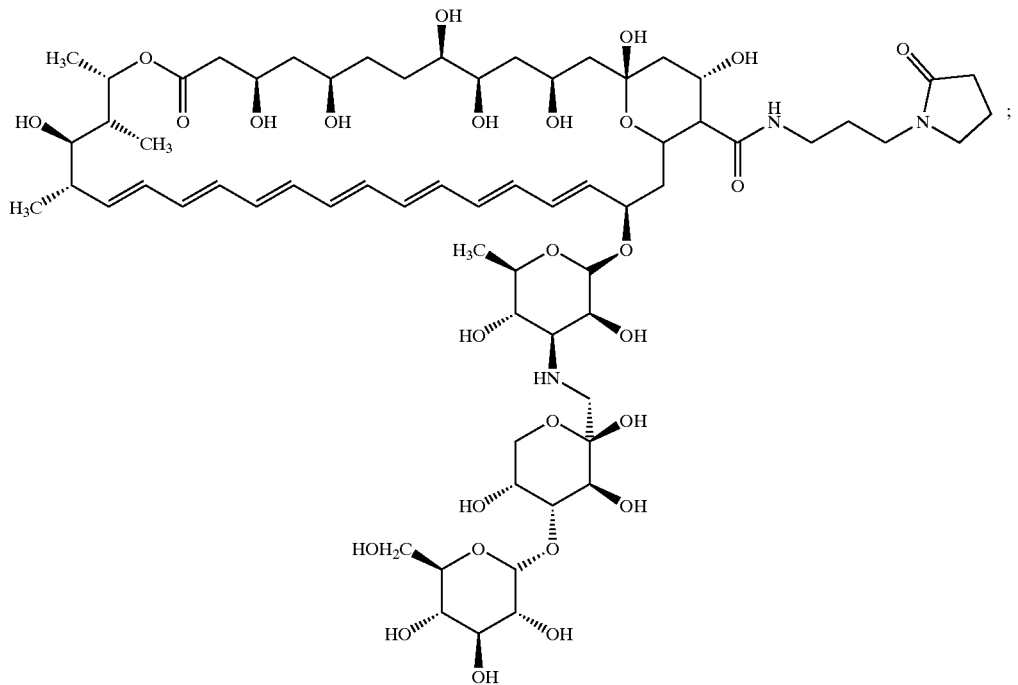
(122)
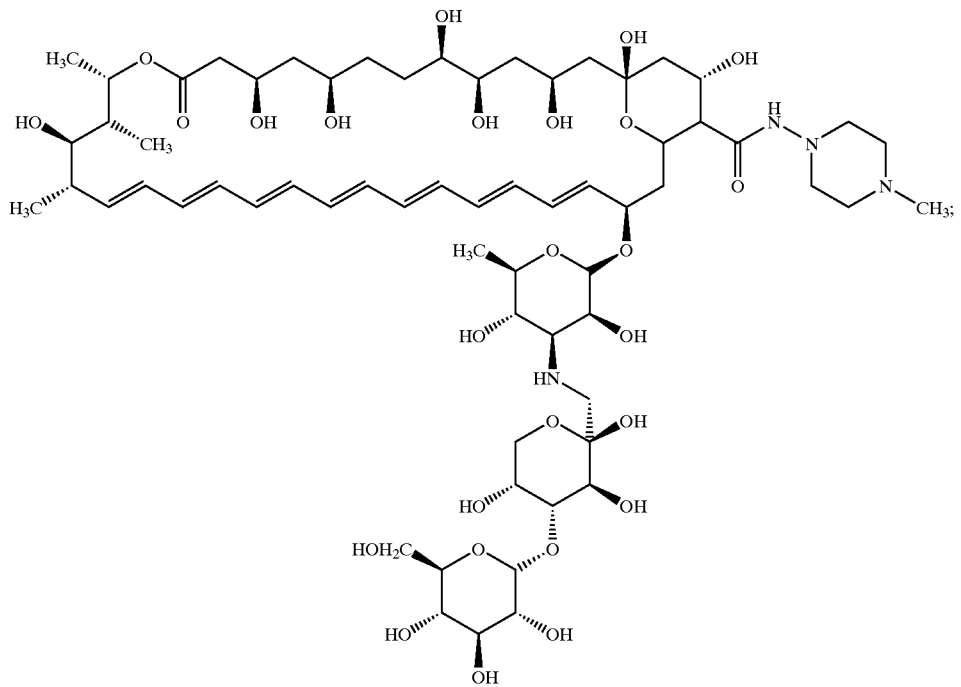
(138)

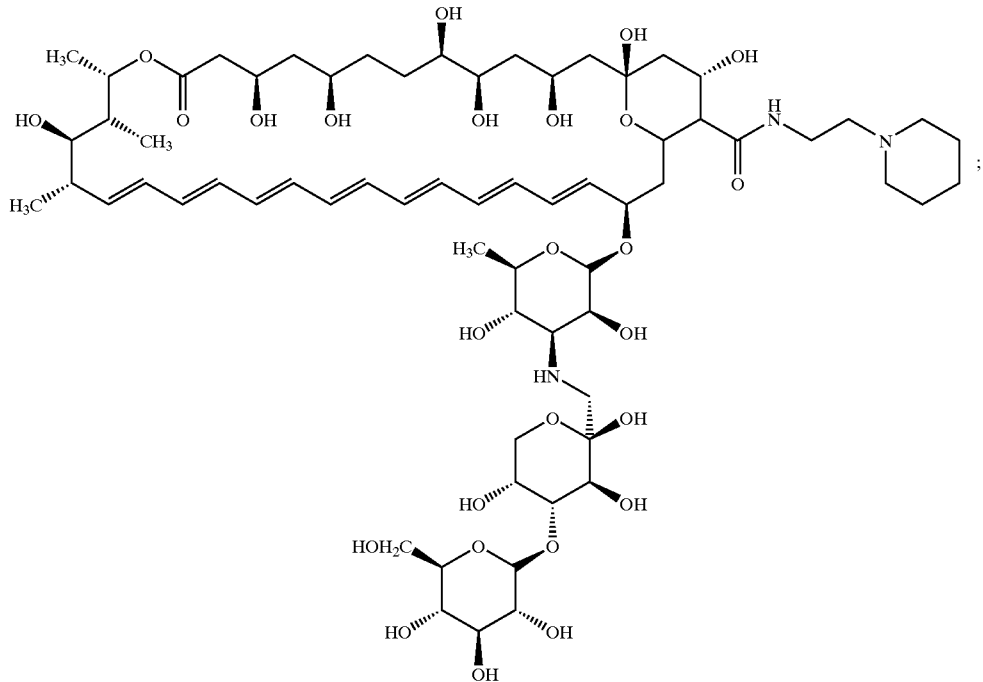
(142)
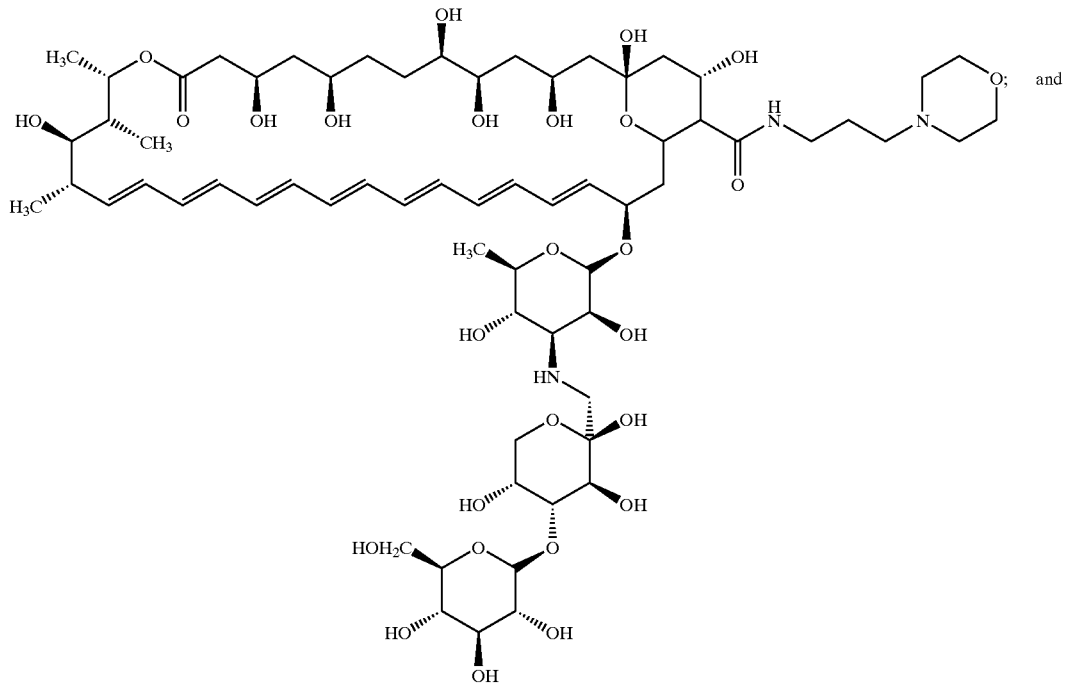
(144)
and

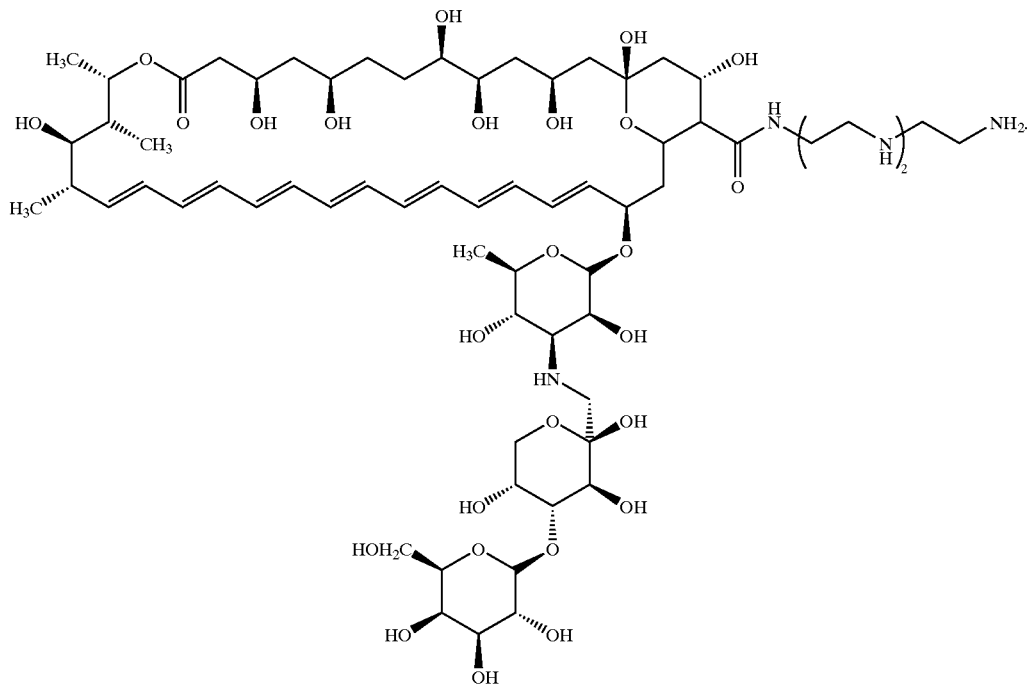
(145)
39. The compound of claim 1 selected from the group consisting of
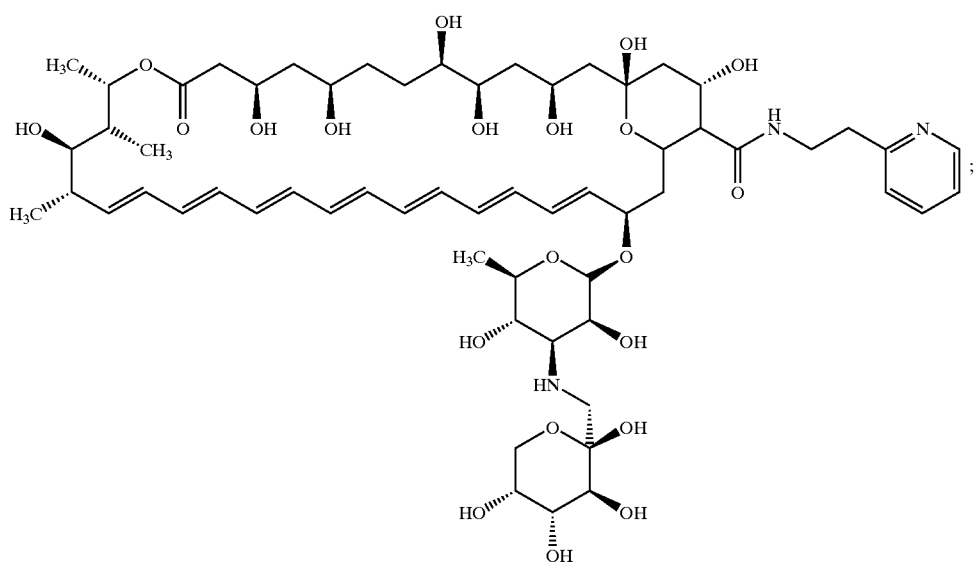
(101)

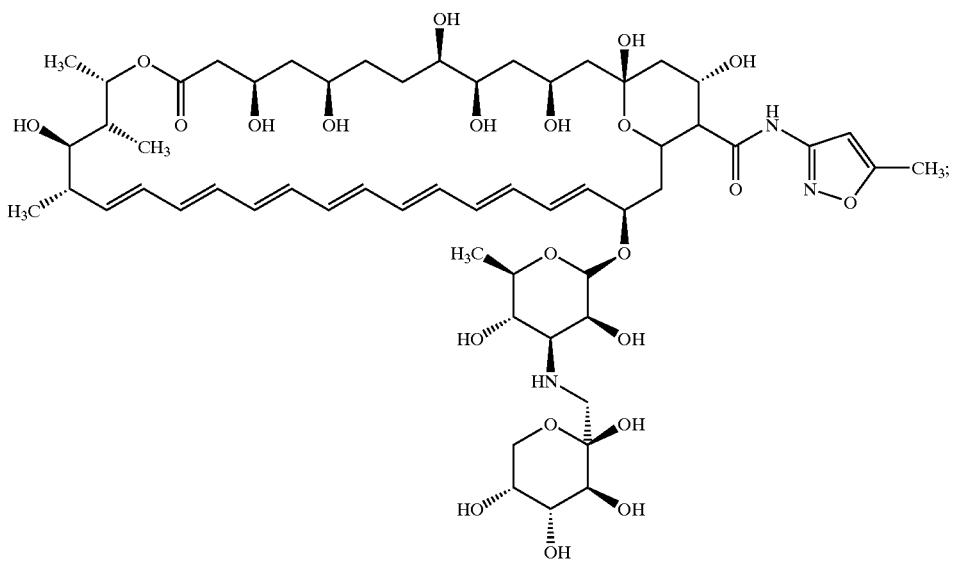
(102)
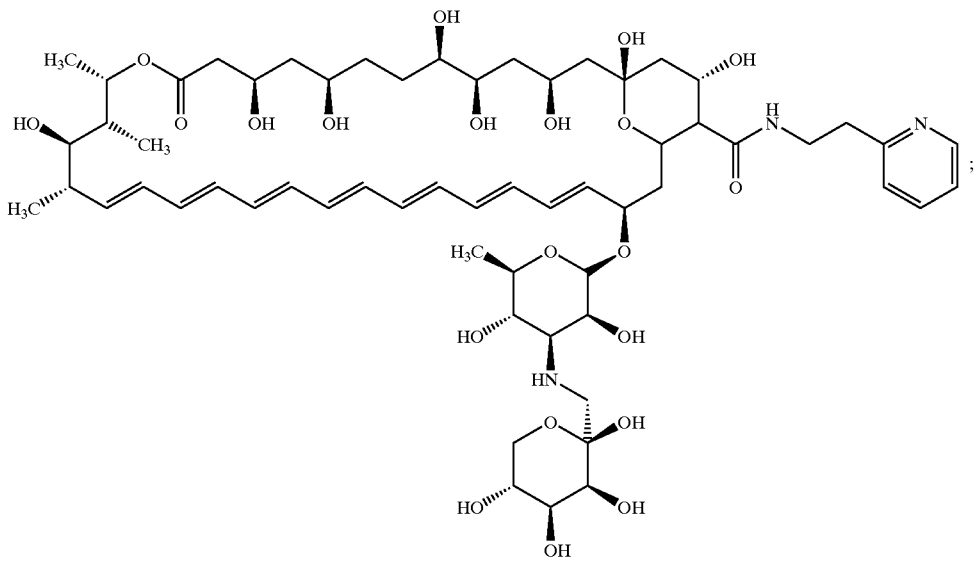
(109)
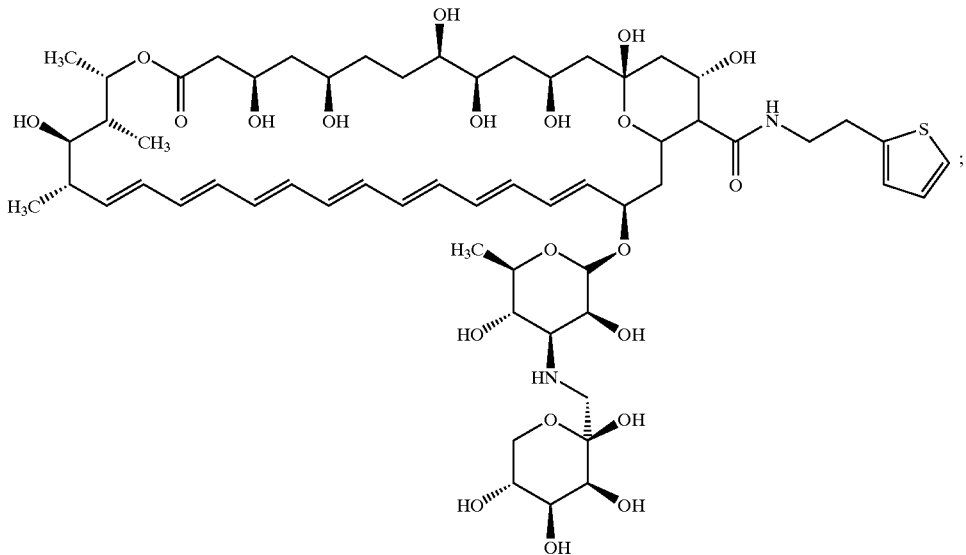
(115)

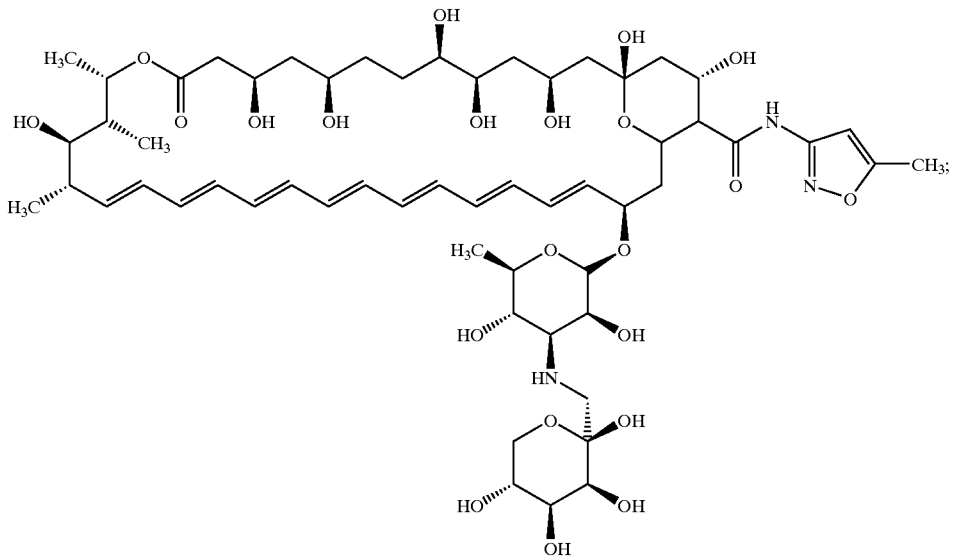
(132)
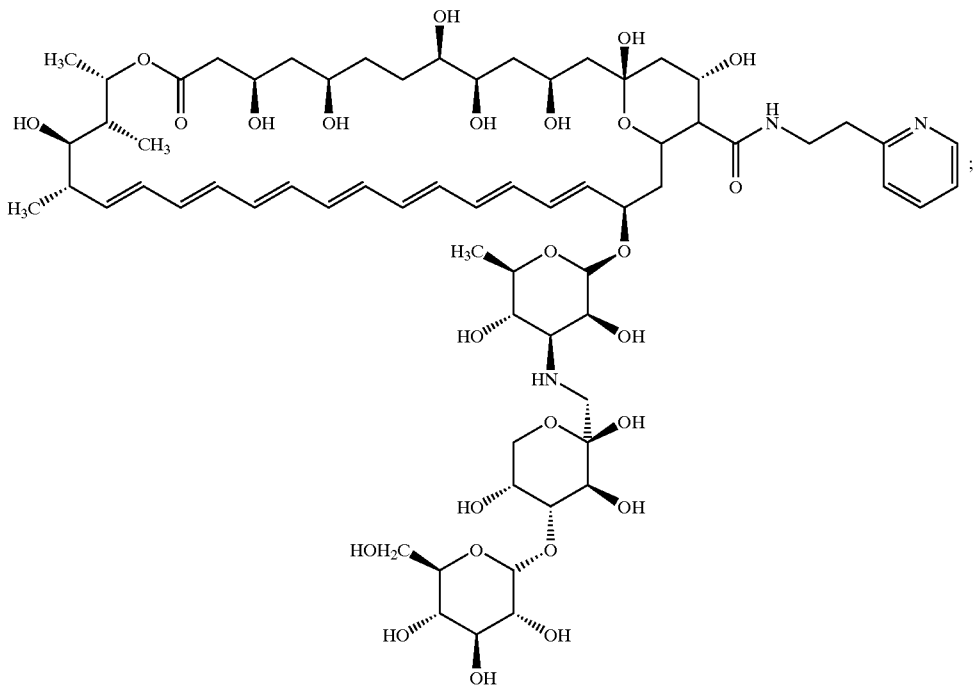
(116)

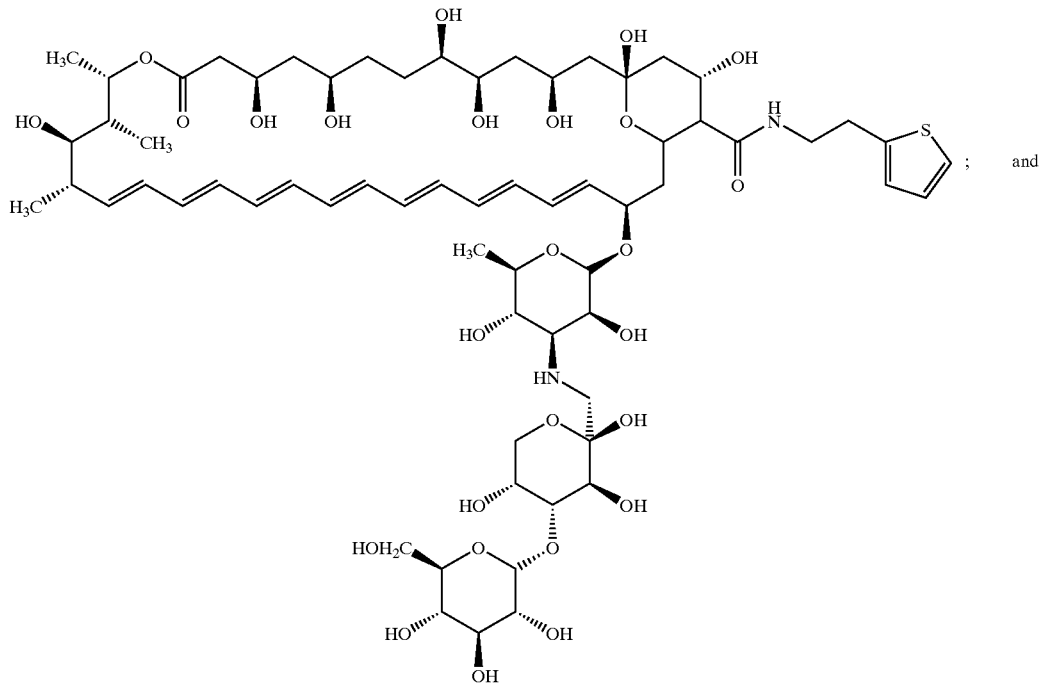
(121)
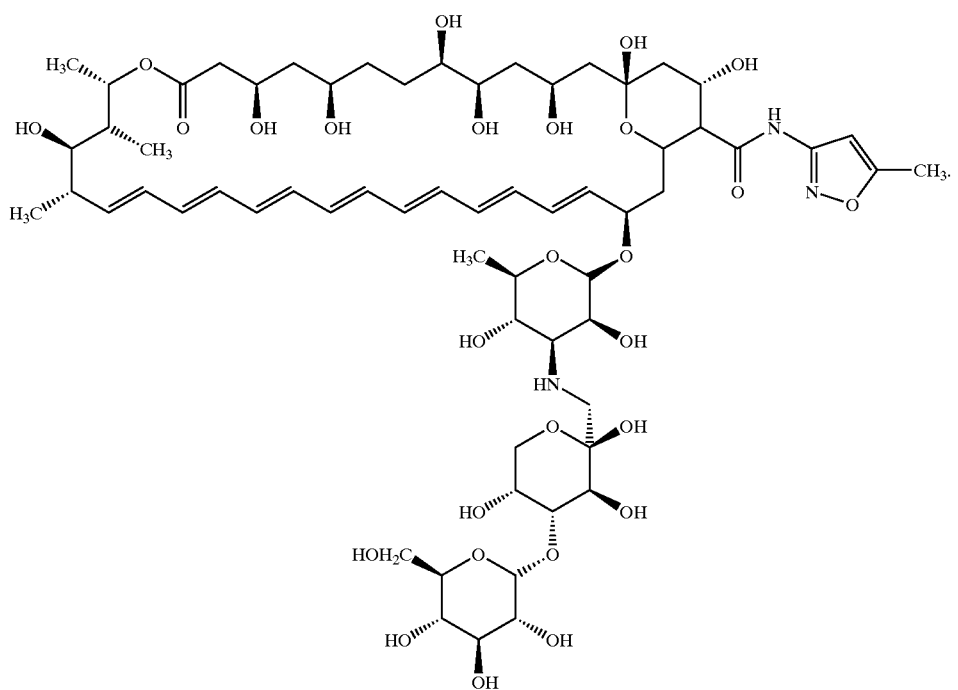
(139)

40. The compound of claim 1 selected from the group consisting of:
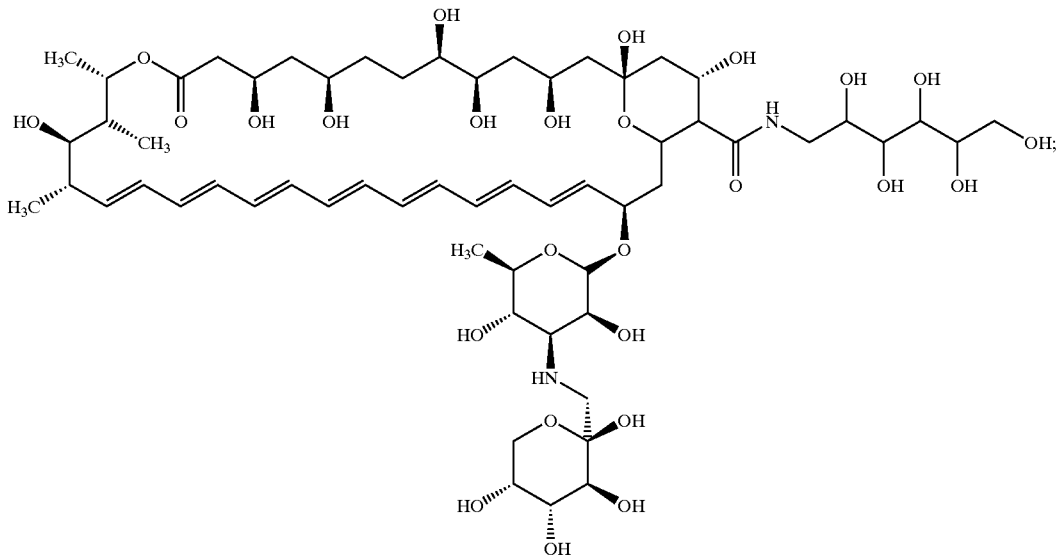
(103)
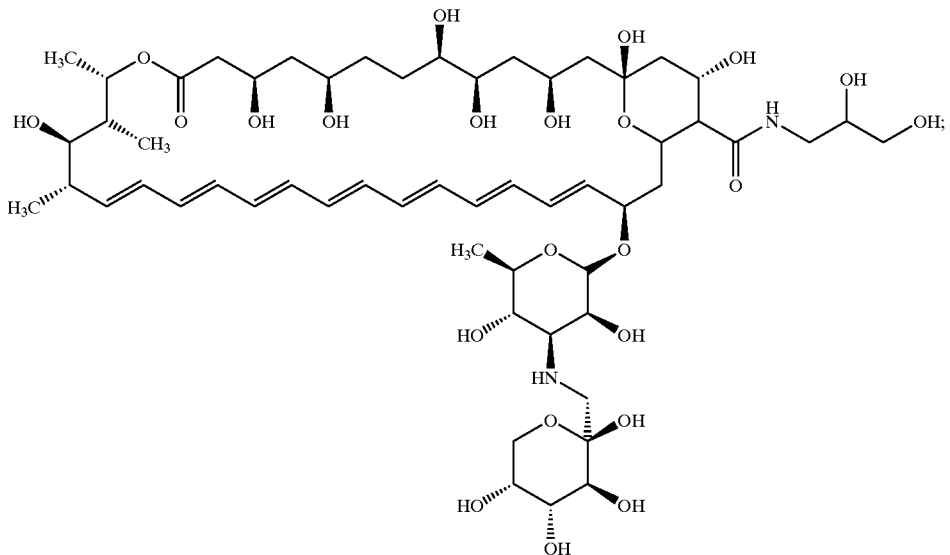
(105)

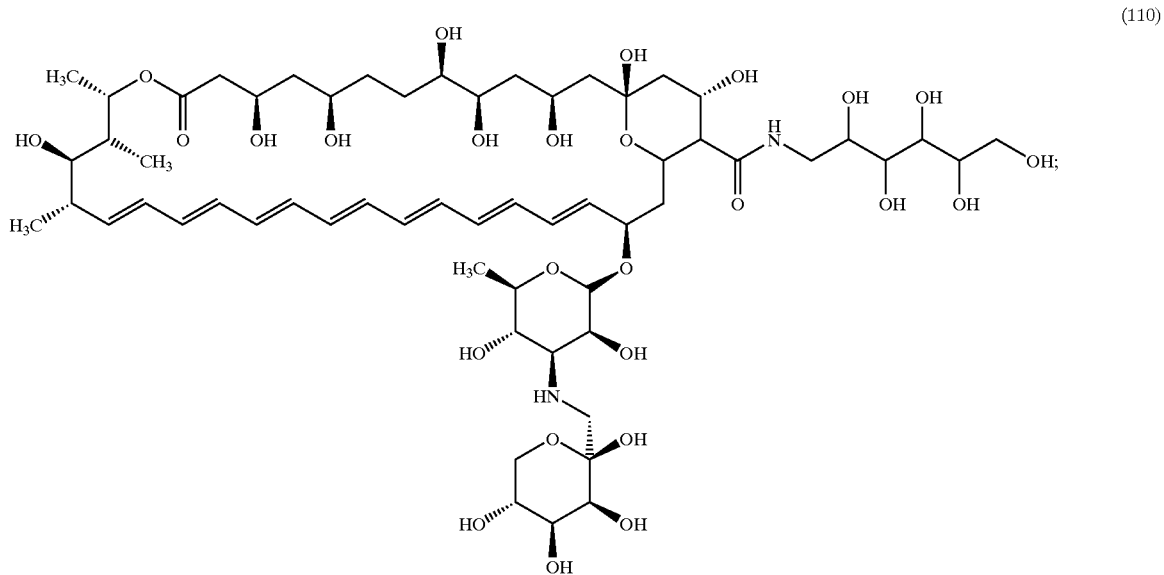
(110)
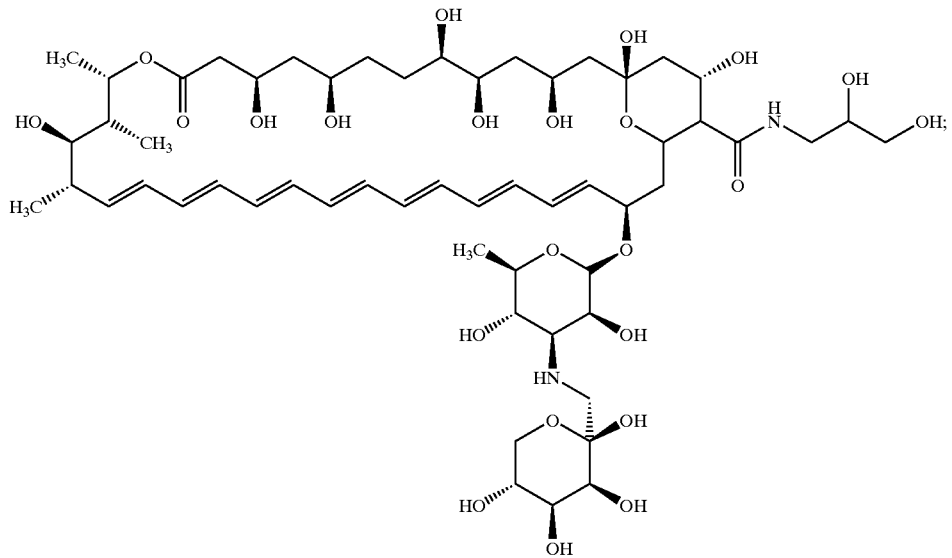
(112)

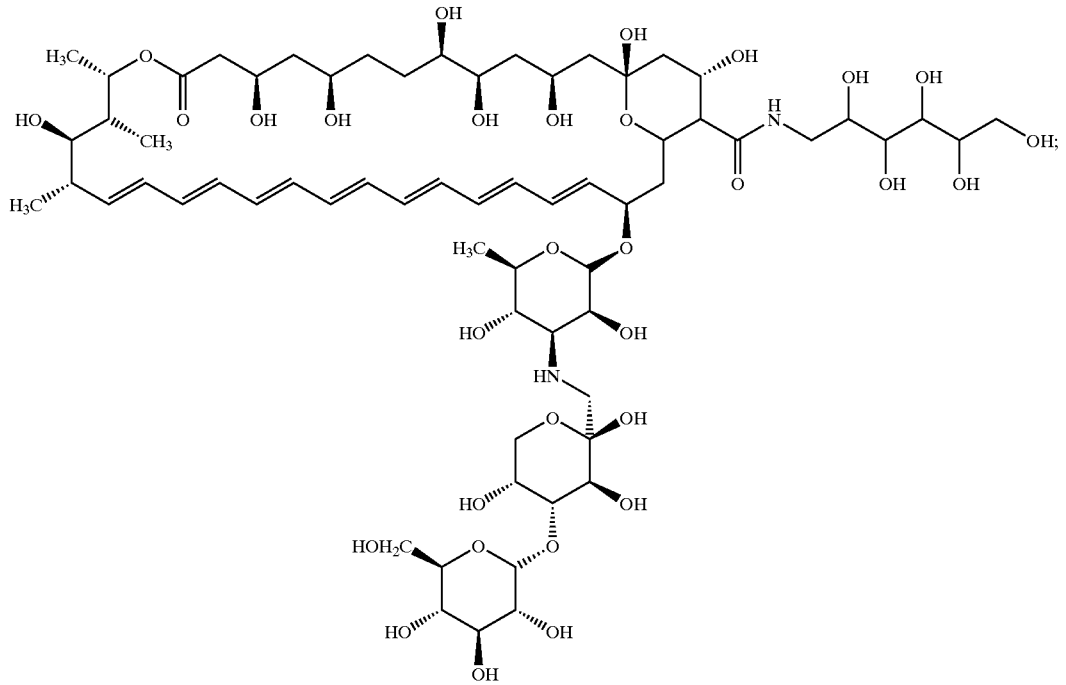
(117)
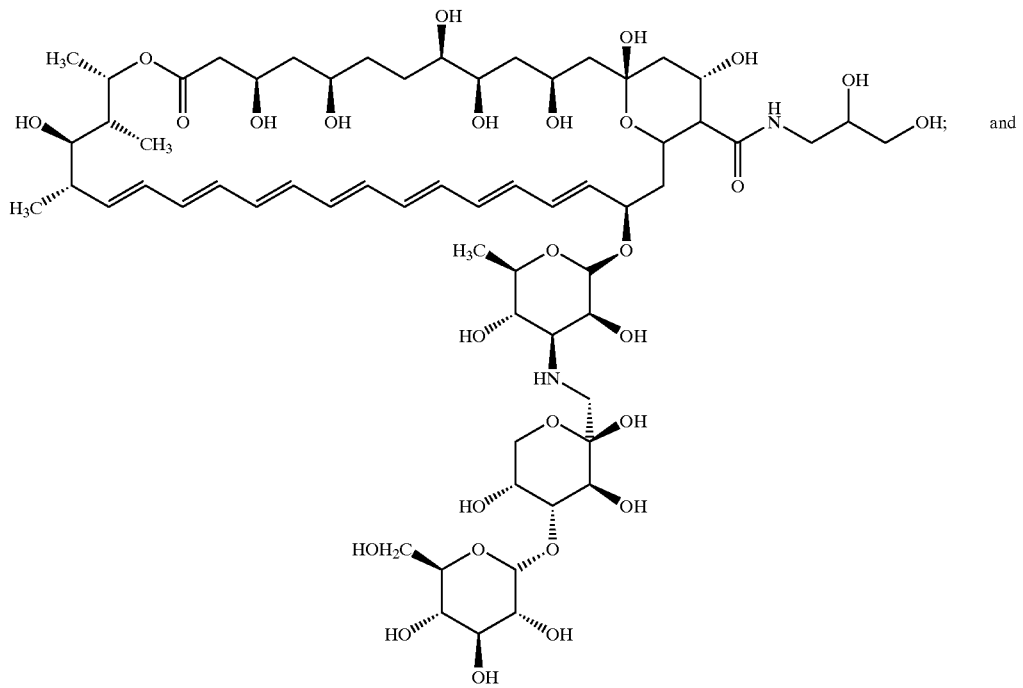
(119)
and

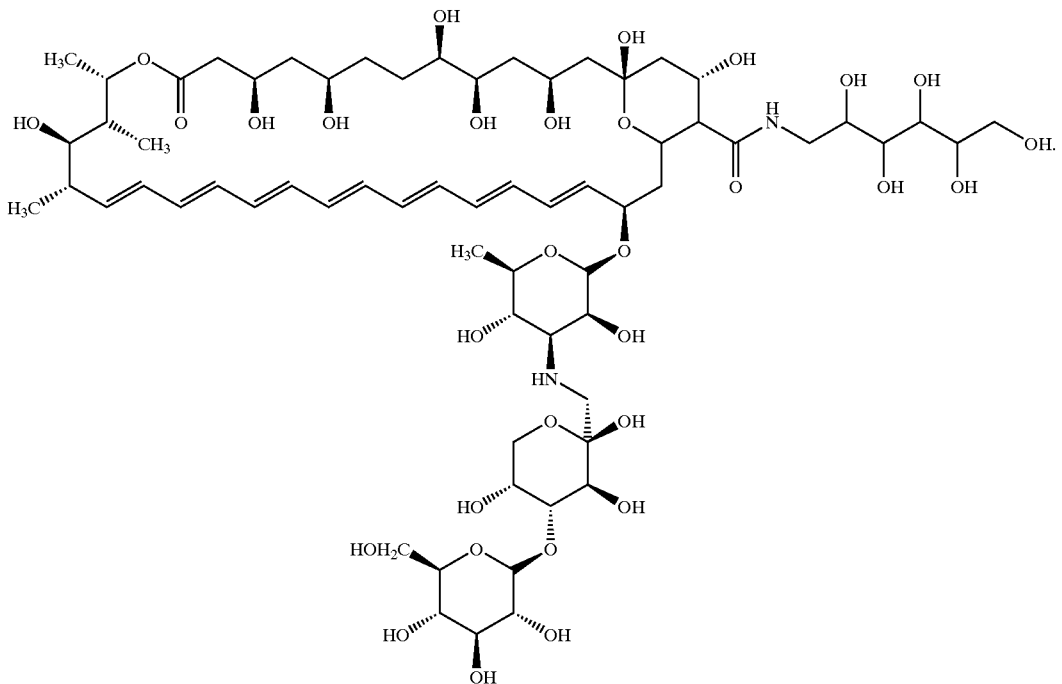
(141)
41. The compound of claim 1 selected from the group consisting of:
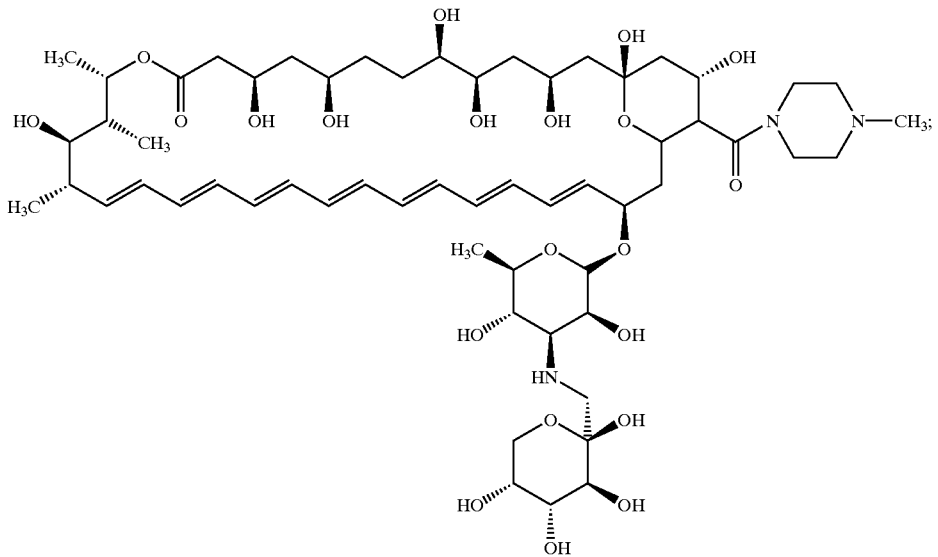
(106)

-continued
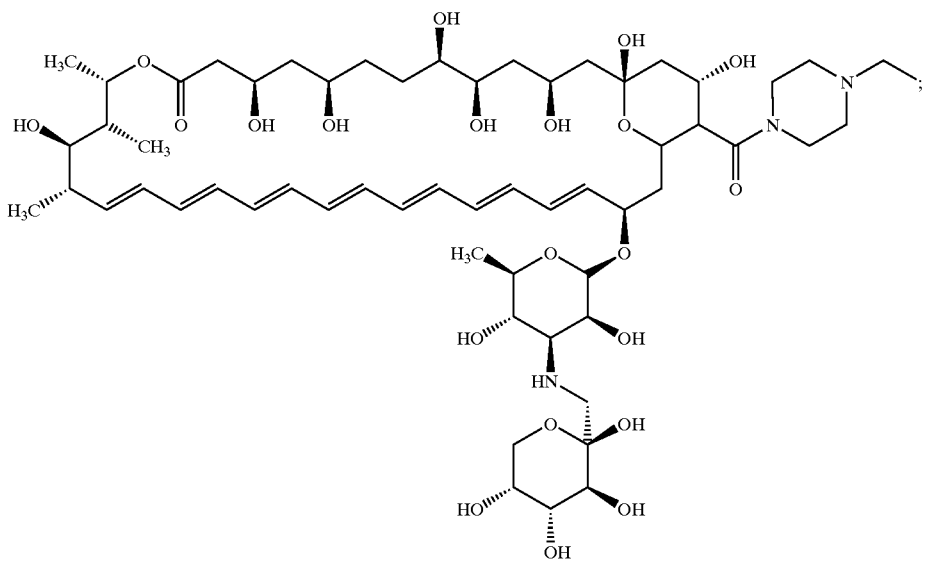
(127)
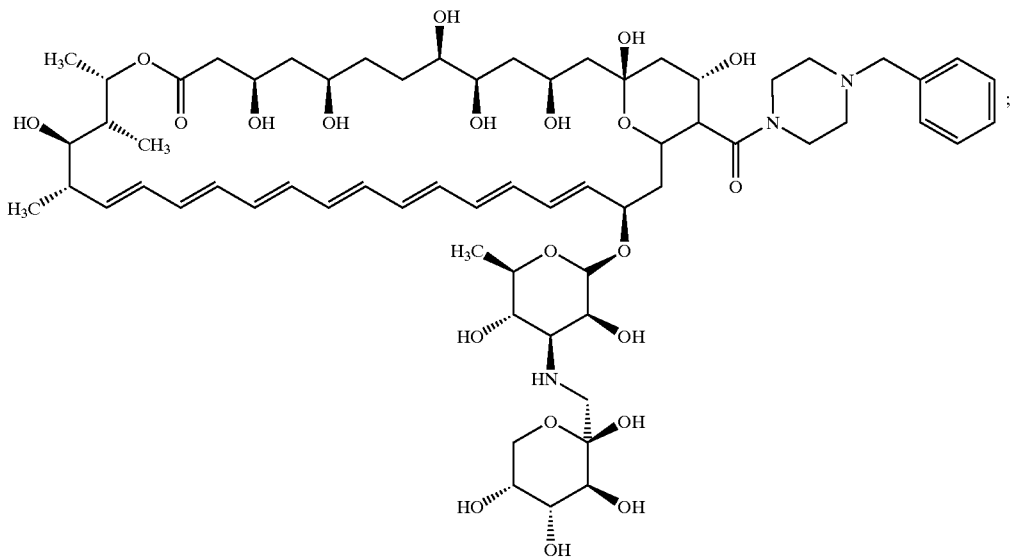
(128)
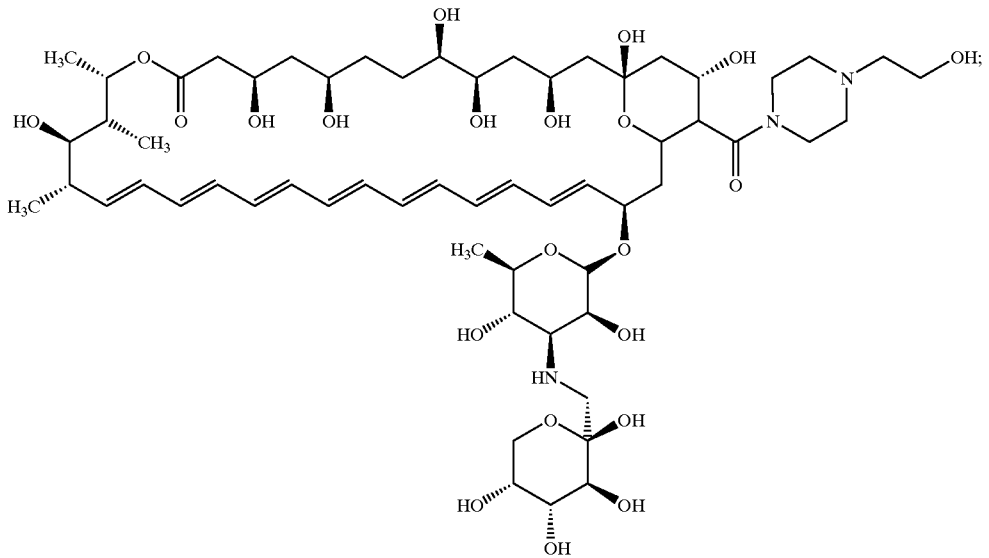
(129)

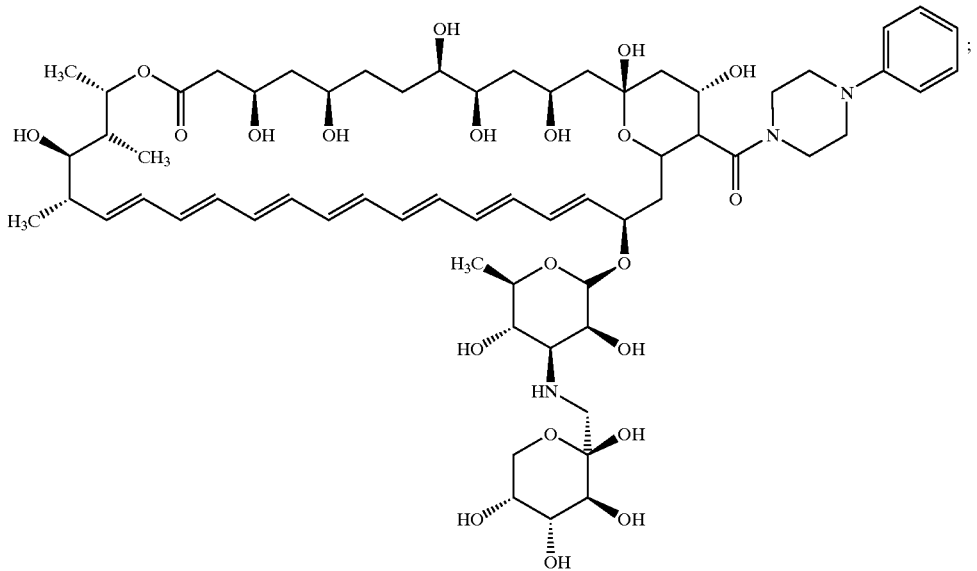
(130)
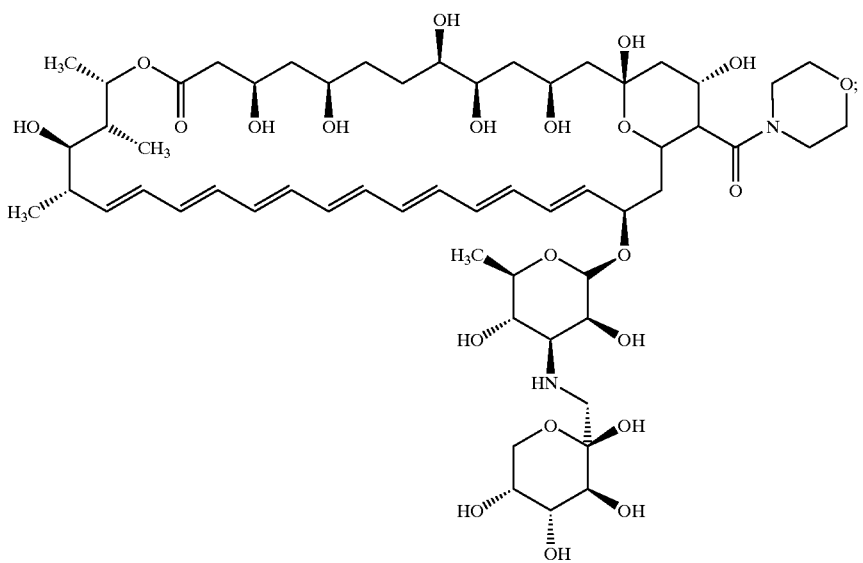
(131)

-continued
(113)
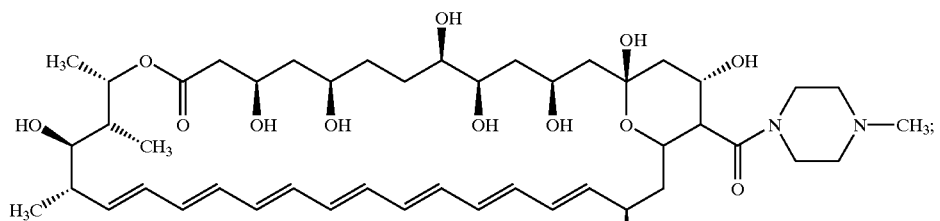
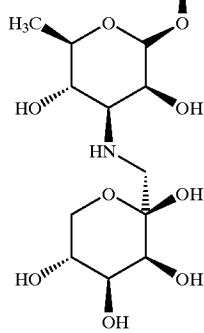
(133)
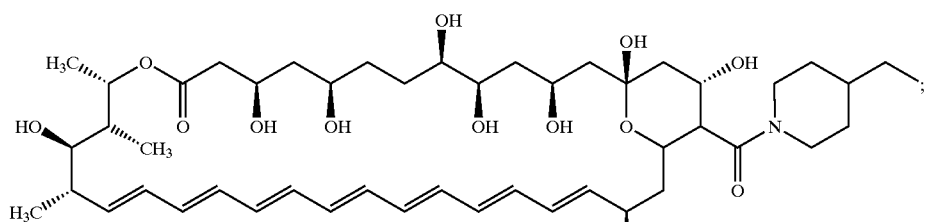
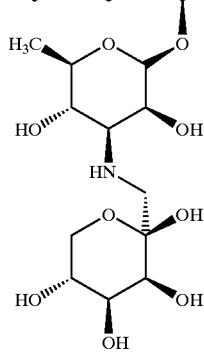
(135)
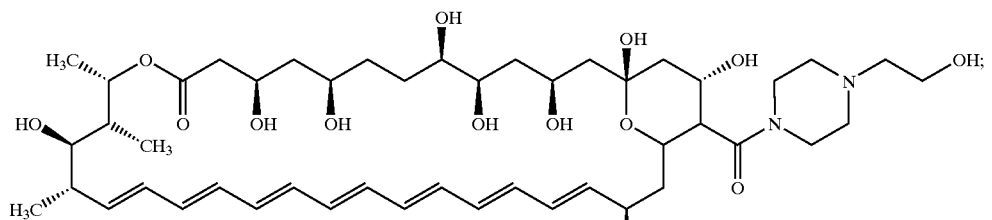
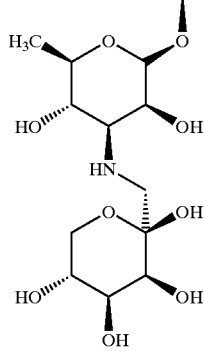

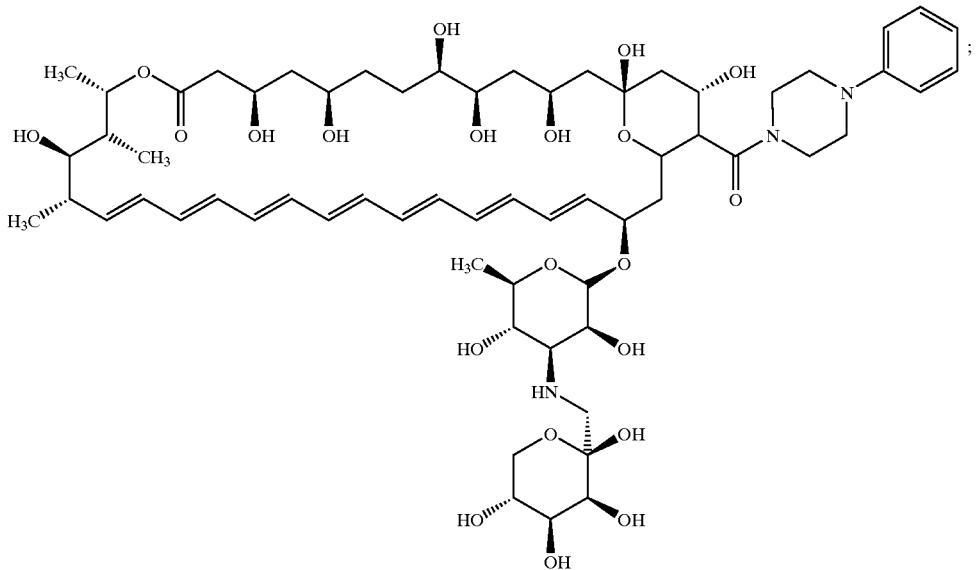
(136)
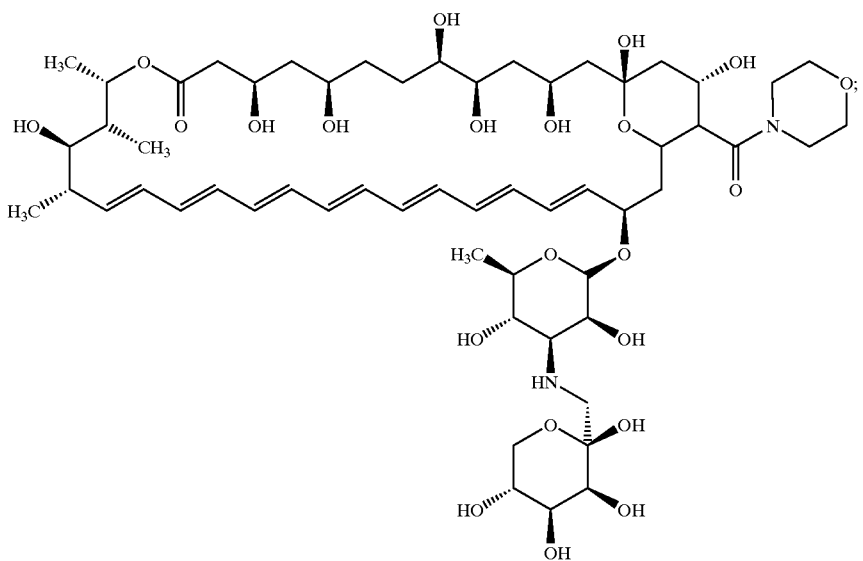
(137)

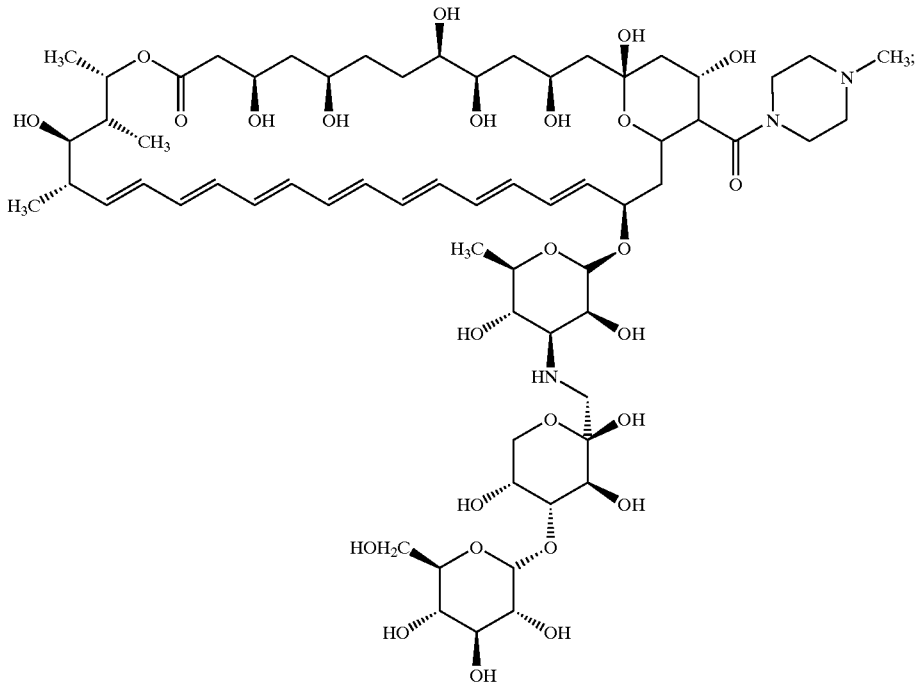
(140)
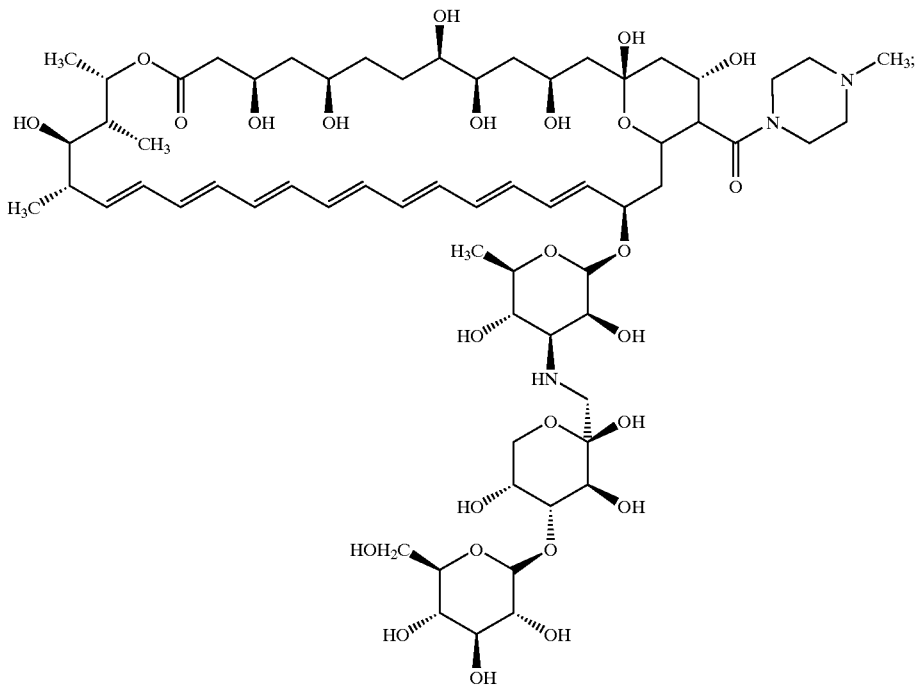
(143)

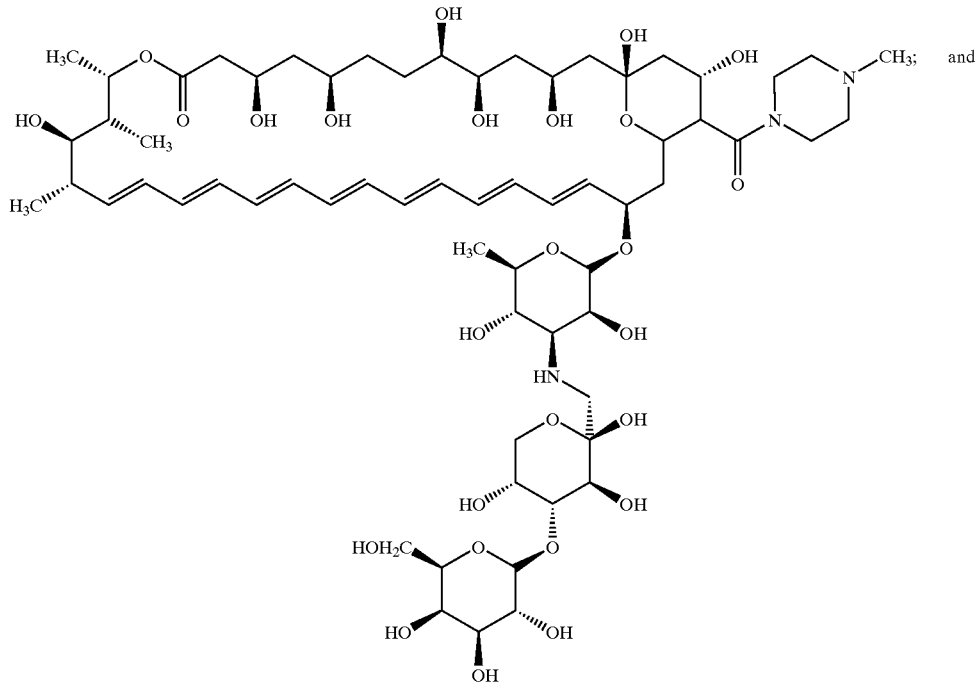
(146)
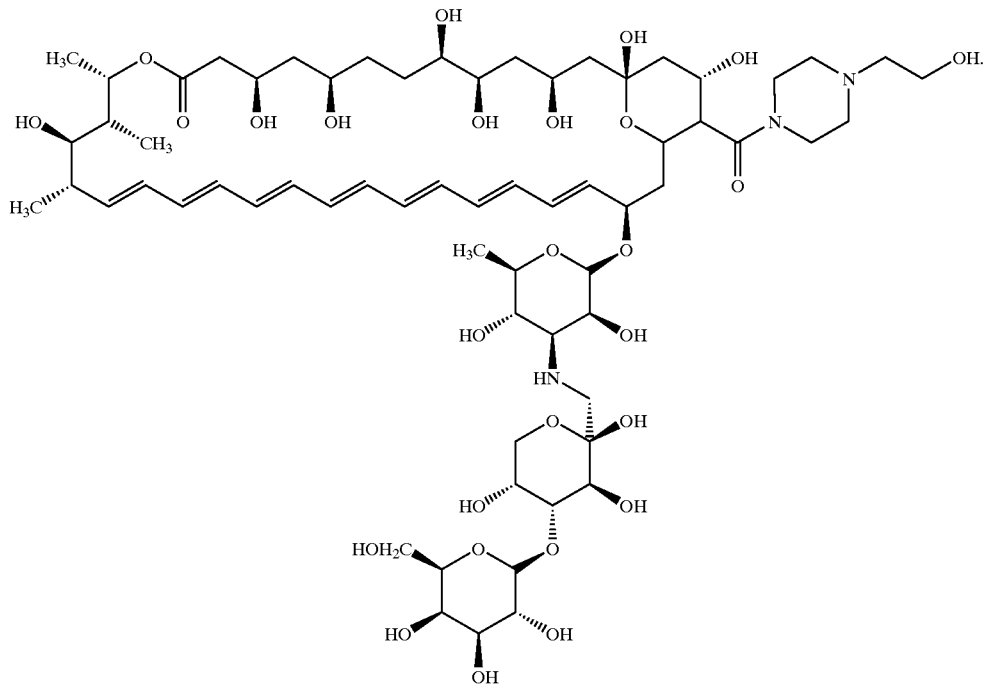
(147)
* * * * *

UNITED STATES PATENT AND TRADEMARK OFFICE
CERTIFICATE OF CORRECTION

PATENT NO. : 6,664,241 B2
DATED : December 16, 2003
INVENTOR(S) : Conway C. Chang et al.

It is certified that error appears in the above-identified patent and that said Letters Patent is hereby corrected as shown below:

Column 93,
Line 57, "form 5- or" should read as -- form a 5- or --.

Column 99,
Line 15, "uranium" should read as -- uronium --.

Column 100,
Line 32 and 49, "claim 14," should read as -- claim 12, --.
Line 56, "claims 25,27,31 or 35." should read as -- claims 25, 27, 31, 32, or 35. --.

Signed and Sealed this

Twenty-fifth Day of May, 2004

JON W. DUDAS
*Acting Director of the United States Patent and Trademark Office*